(12) United States Patent
Kanai et al.

(10) Patent No.: US 8,298,143 B2
(45) Date of Patent: Oct. 30, 2012

(54) ULTRASONOGRAPH THAT DETERMINES TISSUE PROPERTIES UTILIZING A REFERENCE WAVEFORM

(75) Inventors: Hiroshi Kanai, Miyagi (JP); Hideyuki Hasegawa, Miyagi (JP); Hisashi Hagiwara, Kanagawa (JP)

(73) Assignee: Panasonic Corporation, Osaka (JP)

( * ) Notice: Subject to any disclaimer, the term of this patent is extended or adjusted under 35 U.S.C. 154(b) by 697 days.

(21) Appl. No.: 11/915,884

(22) PCT Filed: May 25, 2006

(86) PCT No.: PCT/JP2006/310431
§ 371 (c)(1),
(2), (4) Date: Sep. 4, 2009

(87) PCT Pub. No.: WO2006/129545
PCT Pub. Date: Dec. 7, 2006

(65) Prior Publication Data
US 2009/0318806 A1    Dec. 24, 2009

(30) Foreign Application Priority Data

| May 30, 2005 | (JP) | 2005-157957 |
| May 30, 2005 | (JP) | 2005-157958 |
| Jun. 17, 2005 | (JP) | 2005-178361 |
| Jun. 22, 2005 | (JP) | 2005-181470 |
| Jun. 22, 2005 | (JP) | 2005-181477 |
| Jul. 25, 2005 | (JP) | 2005-214349 |

(51) Int. Cl.
*A61B 8/00* (2006.01)
(52) U.S. Cl. .......... 600/437; 600/443; 600/449
(58) Field of Classification Search .......... None
See application file for complete search history.

(56) References Cited

U.S. PATENT DOCUMENTS

| 4,630,612 | A * | 12/1986 | Uchida et al. | 600/441 |
| 5,183,048 | A * | 2/1993 | Eberle | 600/463 |
| 5,724,974 | A * | 3/1998 | Goodsell et al. | 600/453 |
| 5,785,654 | A | 7/1998 | Iinuma et al. | |
| 6,508,768 | B1 | 1/2003 | Hall et al. | |
| 6,673,020 | B2 | 1/2004 | Okada et al. | |

(Continued)

FOREIGN PATENT DOCUMENTS

JP    09-201361    8/1997

(Continued)

OTHER PUBLICATIONS

English translation of JP2003126090.*

(Continued)

*Primary Examiner* — Long V. Le
*Assistant Examiner* — Bradley Impink
(74) *Attorney, Agent, or Firm* — Renner, Otto, Boisselle & Sklar, LLP

(57) ABSTRACT

An ultrasonic diagnostic apparatus includes a transmitting section that generates a drive signal to drive a probe in order to transmit an ultrasonic wave toward a subject to be deformed periodically under stress. A receiving section receives an echo, produced when the ultrasonic wave is reflected from the subject, at the probe to generate a received echo signal. A computing section determines a thickness change waveform, representing a variation in distance between two arbitrary measuring points on the subject, based on the received echo signal. A reference waveform generating section outputs a reference waveform. The apparatus obtains a subject's internal information by comparing the thickness change waveform and the reference waveform to each other.

15 Claims, 26 Drawing Sheets

U.S. PATENT DOCUMENTS

2001/0016686 A1* 8/2001 Okada et al. ............... 600/454
2007/0055149 A1* 3/2007 Suzuki et al. ............... 600/437

FOREIGN PATENT DOCUMENTS

| | | |
|---|---|---|
| JP | 10-005226 | 1/1998 |
| JP | 2000-229078 | 8/2000 |
| JP | 2001-218768 | 8/2001 |
| JP | 2003-126090 | 5/2003 |
| WO | WO 2004103185 A1 * | 12/2004 |

OTHER PUBLICATIONS

Hideyuki Hasegawa et al., "Modified Phased Tracking Method for Measurement of Change in Thickness of Arterial Wall", JPN. J. Appl. Phys, vol. 41, No. 5b, May 2002, pp. 3563-3571.

Roch L. Maurice et al., "Non-invasive high-frequency vascular ultrasound elastography", Phys. Med. Biol., vol. 50, No. 7, Apr. 2005, pp. 1611-1628.

Roch L. Maurice et al., "On the potential of the Lagrangian speckle model estimator to characterize atherosclerotic plaques in endovascular elastography: In vitro experiments using an excised human carotid artery" Ultrasound in Medicine and Biology, vol. 31, No. 1, Jan. 2005, pp. 85-91.

Hideyuki Hasegawa et al., "Detection of Lumen-Intima Interface of Posterior Wall for Measurement of Elasticity of the Human Carotid Artery", IEEE Transactions on Ultrasonics, Ferroelectrics, and Frequency Control, vol. 51, No. 1, Jan. 2004, pp. 93-108.

Roch L. Maurice et al., "Lagrangian Speckle Model and Tissue-Motion Estimation-Theory", IEEE Transactions on Medical Imaging, vol. 18, No. 7, Jul. 1999, whole document.

Hideyuki Hasegawa et al., "Evaluating the regional elastic modulus of a cylindrical shell with nonuniform wall thickness", J Med Ultrasonics, vol. 31, No. 2, Jun. 2004, pp. 81-90.

European Search Report for corresponding application No. EP 06756581 mailed Nov. 12, 2009.

International Search Report for corresponding Application No. PCT/JP2006/310431 dated Aug. 29, 2006.

H. Hasegawa et al.; "Evaluation of Regional Elastic Modulus of Cylindrical Shell with Non-Uniform Wall Thickness"; J Med Ultrasonics; vol. 28, No. 1; 2001; pp. 1-35 (cited in [0008], p. 3 of the description).

PCT/ISA/237 and partial English translation.

* cited by examiner

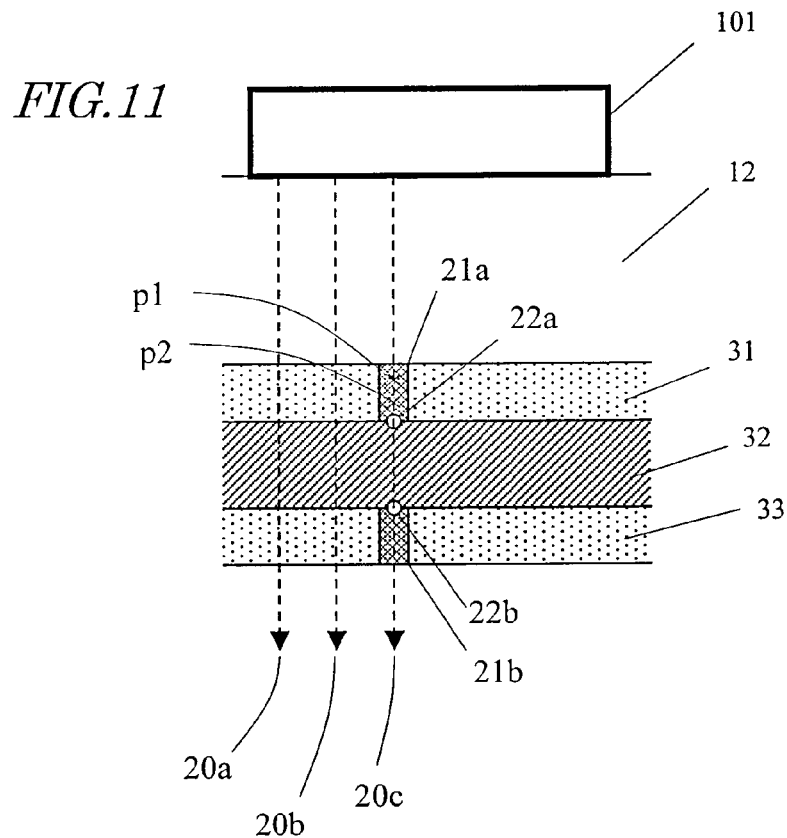
FIG.11
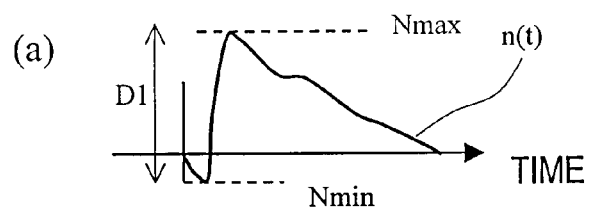
FIG.12
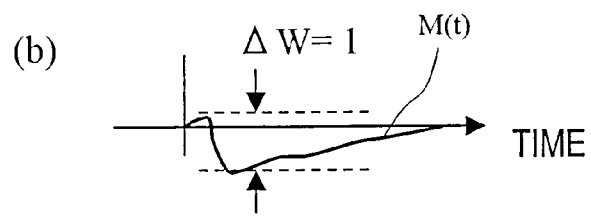
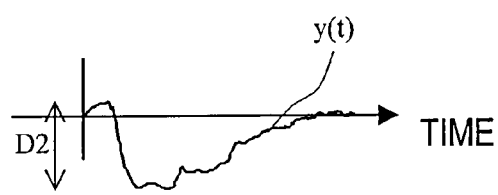
FIG.13

ULTRASONOGRAPH THAT DETERMINES TISSUE PROPERTIES UTILIZING A REFERENCE WAVEFORM

TECHNICAL FIELD

The present invention relates to an ultrasonic diagnostic apparatus and more particularly relates to an ultrasonic diagnostic apparatus for estimating the attribute property values of a subject's tissue.

BACKGROUND ART

An ultrasonic diagnostic apparatus is used to make a non-invasive checkup on a subject by irradiating him or her with an ultrasonic wave and analyzing the information contained in its echo signal. For example, a conventional ultrasonic diagnostic apparatus that has been used extensively converts the intensity of an echo signal into its associated pixel luminance, thereby presenting the subject's structure as a tomographic image. In this manner, the internal structure of the subject can be known. Meanwhile, an ultrasonic diagnostic apparatus for presenting subject's motion information such as blood flow information as an image by detecting Doppler shift in an echo signal has also been used.

Meanwhile, some people are attempting recently to track the motion of a subject's tissue more precisely and evaluate the strain and the modulus of elasticity, coefficient of viscosity or any other physical (attribute) property of the tissue mainly by analyzing the phase of the echo signal.

Patent Document No. 1 discloses a method for tracking a subject's tissue highly precisely and sensing very small vibrations of a cardiac tissue beating by determining the instantaneous location of the subject based on the amplitude and phase of the detected output signal of an echo signal. According to this method, a number of ultrasonic pulses are transmitted in the same direction toward a subject at regular intervals $\Delta T$ and the ultrasonic waves reflected from the subject are received. As shown in FIG. 32, the received echo signals are identified by $y(t)$, $y(t+\Delta T)$ and $y(t+2\Delta T)$, respectively. Supposing the pulse transmission time t is 0, the receiving time t1 of an echo signal produced at a certain depth x1 is given by $t1=x1/(C/2)$, where C is the sonic velocity. In this case, if the phase shift between $y(t1)$ and $y(t1+\Delta T)$ is $\Delta\theta$ and the center frequency of the ultrasonic wave around t1 is f, the magnitude of displacement $\Delta x$ of x1 during this period $\Delta T$ is calculated by the following Equation (1).

$$\Delta x = -C \cdot \Delta\theta / 4\pi f \quad (1)$$

The location x1' of x1 in $\Delta T$ seconds can be figured out by adding the magnitude of displacement $\Delta x$ to x1 as in the following Equation (2).

$$x1' = x1 + \Delta x \quad (2)$$

By repeatedly performing this calculation, the same location x1 of the subject can be tracked. This method is called a "phased tracking method".

Patent Document No. 2 further develops the method of Patent Document No. 1 into a method of calculating the modulus of elasticity of a subject's tissue (e.g., an arterial wall, in particular). According to this method, first, an ultrasonic wave is transmitted from a probe 101 toward a blood vessel wall 16 as shown in FIG. 33. And the echo signals, reflected from measuring points A and B on the blood vessel wall 16, are analyzed by the method of Patent Document No. 1, thereby tracking the motions of the measuring points A and B. FIG. 34 shows the tracking waveforms TA and TB of the measuring points A and B along with an electrocardiographic complex ECG.

As shown in FIG. 34, the tracking waveforms TA and TB have the same periodicity as the electrocardiographic complex ECG, which shows that the artery dilates and shrinks in sync with the cardiac cycle of the heart. More specifically, when the electrocardiographic complex ECG has outstanding peaks called "R waves", the heart starts to shrink, thus pouring blood flow into the artery and raising the blood pressure. As a result, the blood vessel wall is dilated rapidly. That is why soon after the R wave has appeared on the electrocardiographic complex ECG, the artery dilates rapidly and the tracking waveforms TA and TB rise steeply, too. After that, however, as the heart dilates slowly, the artery shrinks gently and the tracking waveforms TA and TB gradually fall to their original levels. The artery repeats such a motion cyclically.

The difference between the tracking waveforms TA and TB is represented as a waveform W showing a variation in thickness between the measuring points A and B. The thickness change waveform W may also be regarded as a waveform representing strain between A and B. The greatest thickness change $\Delta W$ can be calculated as a difference between the maximum and minimum values Wmax and Wmin of the thickness change waveform W:

$$\Delta W = W\text{max} - W\text{min} \quad (3)$$

Supposing the reference thickness between the measuring points A and B during initialization is Ws, the magnitude of maximum strain $\epsilon$ between the measuring points A and B is calculated by the following Equation (4).

$$\epsilon = \Delta W / Ws \quad (4)$$

Also, in this case, the highest and lowest blood pressures Pmax and Pmin of the subject are measured with a blood pressure manometer, for example. The blood pressure difference $\Delta P$ is given by the following Equation (5).

$$\Delta P = P\text{max} - P\text{min} \quad (5)$$

The magnitude of maximum strain $\epsilon$ should be caused by the blood pressure difference $\Delta P$. As the modulus of elasticity Er is defined as a value obtained by dividing the stress by the strain, the modulus of elasticity Er between the measuring points A and B is given by the following Equation (6).

$$Er = \Delta P / \epsilon = \Delta P \cdot Ws / \Delta W \quad (6)$$
$$= \Delta P \cdot Ws / (W\text{max} - W\text{min})$$

Non-Patent Document No. 1 discloses a method for calculating the modulus of elasticity of each portion based on the magnitude of maximum strain $\epsilon$ and the blood pressure difference $\Delta P$ in a situation where the blood vessel has non-uniform thicknesses.

Therefore, by making these calculations on multiple spots on a tomographic image, an image representing the distribution of elasticities Er can be obtained. If an atheroma 11 has been created in the blood vessel wall 16 as shown in FIG. 33, the atheroma and its surrounding blood vessel wall tissue have different elasticities. That is why if an image representing the distribution of elasticities is obtained, it can be determined how and where the atheroma has been produced.

Patent Document No. 1: Japanese Patent Application Laid-Open Publication No. 10-5226
Patent Document No. 2: Japanese Patent Application Laid-Open Publication No. 2000-229078

Non-Patent Document No. 1: Hasegawa et al., Evaluation of Regional Elastic Modulus of Cylindrical Shell with Non-Uniform Wall Thickness, J Med Ultrasonics, Vol. 28, No. 1 (2001)

DISCLOSURE OF INVENTION

Problems to be Solved by the Invention

According to the conventional method of measuring a modulus of elasticity, however, the modulus of elasticity is calculated based on the maximum and minimum values Wmax and Wmin of the thickness change waveform W, and therefore, the noise resistance is low. For example, if the thickness change waveform W shown in FIG. 35 is obtained, the modulus of elasticity is calculated using values at times t1 and t2 as the maximum and minimum values Wmax and Wmin, respectively. However, as shown in FIG. 35, the value of the thickness change waveform W at the time t2 includes noise, and is not a proper value.

In addition, even if an erroneous modulus of elasticity is obtained due to the influence of noise as described above, it is difficult to determine, based on other pieces of information, whether that value is improper or not. For example, even if an atheroma 11 has been produced in the vessel wall 16 as shown in FIG. 33, the atheroma 11 could not be detected on a tomographic image that has been generated with an ultrasonic wave. That is why if the modulus of elasticity of a normal portion of the vessel wall 16 were calculated approximately equal to that of the atheroma 11 due to the influence of noise, that normal portion could be diagnosed as an atheroma by mistake.

Besides, in making a diagnosis, it is important whether or not a region with a unique modulus of elasticity is located within the organ being inspected. A B-mode tomographic image, however, cannot show the subject such that every organ within the region of interest is recognizable. That is why the location and range of the target organ cannot be determined in some cases on a tomographic image. Furthermore, there is not always one-to-one correspondence between a modulus of elasticity and a tissue, and therefore, the location and range of the target organ may not be determined in some cases even with a tomographic image representing moduli of elasticity. Consequently, even if the modulus of elasticity has been calculated accurately, it could still be difficult to determine the status of the subject specifically.

In order to overcome at least one of the problems of the prior art described above, the present invention has an object of providing an ultrasonic diagnostic apparatus that can reduce the influence of noise, can estimate an attribute property highly accurately or can obtain a result of analysis on a subject based on its attribute property.

Means for Solving the Problems

An ultrasonic diagnostic apparatus according to the present invention includes: a transmitting section that generates a drive signal to drive a probe in order to transmit an ultrasonic wave toward a subject to be deformed periodically under stress; a receiving section for receiving an echo, produced when the ultrasonic wave is reflected from the subject, at the probe to generate a received echo signal; a computing section for figuring out a thickness change waveform, representing a variation in distance between two arbitrary measuring points on the subject, based on the received echo signal; and a reference waveform generating section for outputting a reference waveform. The apparatus obtains subject's internal information by comparing the thickness change waveform and the reference waveform to each other.

In one preferred embodiment, the ultrasonic diagnostic apparatus further includes a thickness change estimating section for calculating the greatest variation in the thickness change waveform by comparing the thickness change waveform and the reference waveform to each other.

In this particular preferred embodiment, the thickness change estimating section calculates a coefficient to be multiplied by either the thickness change waveform or the reference waveform so as to minimize a matching error between the thickness change waveform and the reference waveform and calculates the greatest thickness change in the thickness change waveform based on the coefficient and the amplitude of the reference waveform.

In another preferred embodiment, the reference waveform generating section includes a storage section that stores data about the reference waveform.

In this particular preferred embodiment, the reference waveform is generated by calculating the average of thickness change waveforms that have been collected in advance from a plurality of subjects.

In a specific preferred embodiment, the ultrasonic diagnostic apparatus further includes a period adjusting section for adjusting the period of the reference waveform to one deformation period of the subject. The thickness change estimating section calculates the greatest variation in the thickness change waveform based on the reference waveform, of which the period has been adjusted, and the thickness change waveform.

In another preferred embodiment, the ultrasonic diagnostic apparatus further includes a period adjusting section for adjusting the period of the thickness change waveform to one deformation period of the subject. The thickness change estimating section calculates the greatest thickness change in the thickness change waveform based on the thickness change waveform, of which the period has been adjusted, and the reference waveform.

In still another preferred embodiment, the ultrasonic diagnostic apparatus further includes an averaging section for averaging the thickness change waveform, of which the period has been adjusted, over multiple periods. The greatest variation in the thickness change waveform is calculated based on the averaged thickness change waveform and the reference waveform.

In yet another preferred embodiment, the ultrasonic diagnostic apparatus further includes a period adjusting section. If the thickness change waveform has inconstant periods, the period adjusting section makes those periods of the thickness change waveform constant by extracting data about the respective periods at an interval that corresponds to the shortest one of the periods of the thickness change waveform.

In yet another preferred embodiment, the computing section includes a displacement waveform calculating section for figuring out a displacement waveform representing displacements of a plurality of measuring points on the subject based on the received echo signal, and a calculating section for figuring out the thickness change waveform between the two measuring points based on the displacement waveform.

In this particular preferred embodiment, the reference waveform generating section generates the reference waveform based on the displacement waveform.

In another preferred embodiment, the ultrasonic diagnostic apparatus further includes a vascular diameter calculating section for figuring out a waveform representing a variation in the vascular caliber of the subject based on the displacement waveform. The reference waveform generating section generates the reference waveform based on the vascular caliber variation waveform.

In still another preferred embodiment, the reference waveform generating section generates the reference waveform based on a waveform representing a variation in the blood pressure of the subject.

In yet another preferred embodiment, the ultrasonic diagnostic apparatus further includes a modulus of elasticity calculating section for getting information about a difference in the stress that has been caused during a deformation period of the subject and for calculating a modulus of elasticity based on the greatest variation.

In yet another preferred embodiment, the ultrasonic diagnostic apparatus further includes a thickness change estimating section for calculating the greatest thickness change and an index indicating a degree of matching between the thickness change waveform and the reference waveform by comparing the reference waveform and the thickness change waveform to each other, and a reliability determining section for determining the reliability of the greatest thickness change based on the index.

In this particular preferred embodiment, the thickness change estimating section calculates the coefficient and a difference to be caused by the use of the coefficient so as to minimize the difference between one of the thickness change and reference waveforms and a waveform obtained by multiplying the other waveform by the coefficient. The thickness change estimating section also calculates the greatest thickness change in the thickness change waveform based on the coefficient and the amplitude of the reference waveform, thereby outputting the difference as the index.

In another preferred embodiment, the reference waveform generating section includes a storage section that stores data about the reference waveform.

In this particular preferred embodiment, the reference waveform is generated by calculating the average of thickness change waveforms that have been collected in advance from a plurality of subjects.

In a specific preferred embodiment, the ultrasonic diagnostic apparatus further includes a period adjusting section for adjusting the period of the thickness change waveform to one deformation period of the subject. The thickness change estimating section calculates the greatest thickness change in the thickness change waveform based on the thickness change waveform, of which the period has been adjusted, and the reference waveform.

In this particular preferred embodiment, the ultrasonic diagnostic apparatus further includes an averaging section for averaging the thickness change waveform, of which the period has been adjusted, over multiple periods. The thickness change estimating section calculates the coefficient, the difference and the greatest thickness change based on the averaged thickness change waveform.

In a specific preferred embodiment, the averaging section calculates the variance of the thickness change waveform based on the average, and the reliability determining section rates the reliability of the greatest thickness change based on the variance and the difference.

In a more specific preferred embodiment, the reliability determining section rates the reliability of the greatest thickness change based on the variance, the coefficient and the difference.

In one preferred embodiment, the ultrasonic diagnostic apparatus further includes: a period adjusting section for adjusting the period of the thickness change waveform to one deformation period of the subject; an averaging section for calculating the average and the variance of the thickness change waveform, of which the period has been adjusted, over multiple periods; a reference waveform generating section for outputting a reference waveform; a thickness change estimating section for calculating the greatest thickness change by comparing the reference waveform and the averaged thickness change waveform to each other; and a reliability determining section for determining the reliability of the greatest thickness change based on the variance.

In this particular preferred embodiment, the thickness change estimating section calculates the coefficient so as to minimize a difference between one of the averaged thickness change and reference waveforms and a waveform obtained by multiplying the other waveform by the coefficient. The thickness change estimating section also calculates the greatest thickness change in the thickness change waveform based on the coefficient and the amplitude of the reference waveform.

In a specific preferred embodiment, the reliability determining section rates the reliability of the greatest thickness change based on the variance and the coefficient.

In another preferred embodiment, the ultrasonic diagnostic apparatus further includes: a modulus of elasticity calculating section for getting information about a difference in the stress that has been caused during a deformation period of the subject and for calculating a modulus of elasticity based on the greatest thickness change; and a display section for displaying the modulus of elasticity according to the degree of reliability that has been determined by the reliability determining section.

In still another preferred embodiment, the subject includes multiple different tissues and the reference waveform generating section outputs multiple reference waveforms. The ultrasonic diagnostic apparatus further includes a thickness change estimating section for calculating an index indicating the degree of matching between the thickness change waveform and each said reference waveform by comparing the reference waveform and the thickness change waveform to each other, and a tissue identifying section for determining, based on the indices, to which of the multiple tissues the tissue that has been located between the two measuring points and produced the thickness change waveform corresponds.

In this particular preferred embodiment, the thickness change estimating section calculates the coefficient and a difference to be caused by the use of the coefficient so as to minimize the difference between one of the thickness change and reference waveforms and a waveform obtained by multiplying the other waveform by the coefficient. The thickness change estimating section also calculates the greatest thickness change in the thickness change waveform for use of each said reference waveform based on the coefficient and the amplitude of the reference waveform, thereby outputting the greatest thickness changes to the tissue identifying section.

In a specific preferred embodiment, the thickness change estimating section outputs each said difference as the index to the tissue identifying section. The tissue identifying section identifies a tissue associated with one of the reference waveforms that has caused the smallest difference as the tissue that has produced the thickness change waveform between the two measuring points and outputs the greatest thickness change that has been calculated based on the reference waveform.

In a more specific preferred embodiment, the ultrasonic diagnostic apparatus further includes a modulus of elasticity calculating section for calculating a modulus of elasticity based on information about a difference in the stress that has been caused during a deformation period of the subject and on the greatest thickness change that has been output by the tissue identifying section.

In another preferred embodiment, the reference waveform generating section includes a storage section that stores data about the reference waveforms.

In this particular preferred embodiment, the reference waveform is generated by calculating the average of thickness change waveforms that have been collected in advance from multiple tissues of a plurality of subjects.

In another preferred embodiment, the ultrasonic diagnostic apparatus further includes an image processing section for generating image data representing the modulus of elasticity based on a result obtained by the tissue identifying section.

In still another preferred embodiment, if each said difference is greater than a predetermined value, the tissue identifying section identifies the tissue that has produced the thickness change waveform between the two measuring points as none of the tissues.

In yet another preferred embodiment, the reference waveform generating section outputs a plurality of viscosity property reference waveforms. The ultrasonic diagnostic apparatus further includes a comparing section for calculating a viscosity property index, indicating the degree of matching between the thickness change waveform and each said viscosity property reference waveform, by comparing the viscosity property reference waveform and the thickness change waveform to each other, and a viscosity coefficient determining section for determining the viscosity coefficient by the viscosity property index.

In this particular preferred embodiment, the viscosity property reference waveform is a strain waveform of the subject that has been obtained based on information about a variation in the stress of the subject who is supposed to have a predetermined viscosity coefficient. The viscosity coefficient determining section outputs the viscosity coefficient associated with the viscosity property reference waveform in which the smallest one of the viscosity property indices is obtained.

In a specific preferred embodiment, the comparing section outputs, as the viscosity property index, a difference in a situation where the coefficient is determined so as to minimize the difference between a waveform obtained by multiplying one of the thickness change and each said viscosity property reference waveforms by a first coefficient and the other waveform.

In a more specific preferred embodiment, the information about the subject's stress variation is a waveform representing the blood pressure of the subject.

In another preferred embodiment, the computing section includes a displacement waveform calculating section for figuring out a displacement waveform representing displacements of a plurality of measuring points on the subject based on the received echo signal, and a thickness change waveform calculating section for figuring out the thickness change waveform between the two measuring points based on the displacement waveform.

In this particular preferred embodiment, the ultrasonic diagnostic apparatus further includes a vascular diameter calculating section for figuring out a waveform representing a variation in the vascular caliber of the subject based on the displacement waveform. The information about the subject's stress variation is obtained by correcting the vascular caliber waveform with the highest and lowest blood pressure values of the subject.

In another preferred embodiment, the reference waveform generating section receives a waveform representing a variation in the thickness of the subject's blood vessel wall in the vicinity of his or her vascular lumen from the computing section, corrects the waveform representing the thickness change near the vascular lumen with the highest and lowest blood pressure values of the subject, and uses the corrected waveform as the information about the subject's stress variation.

In still another preferred embodiment, the reference waveform generating section further generates an elastic property reference waveform, and the comparing section calculates the greatest thickness change in the thickness change waveform by comparing the elastic property reference waveform and the thickness change waveform to each other.

In this particular preferred embodiment, the comparing section determines a second coefficient so as to minimize a difference between a waveform obtained by multiplying one of the thickness change and elastic property reference waveforms by the second coefficient and the other waveform, and calculates the greatest thickness change based on the second coefficient and the amplitude of the elastic property reference waveform.

In a specific preferred embodiment, the ultrasonic diagnostic apparatus further includes a modulus of elasticity calculating section for getting information about a difference in the stress that has been caused during a deformation period of the subject and for calculating a modulus of elasticity based on the greatest variation.

In another preferred embodiment, the reference waveform generating section generates the elastic property reference waveform based on a waveform representing a variation in the blood pressure of the subject.

A control method according to the present invention is a method for controlling an ultrasonic diagnostic apparatus using a control section of the apparatus itself. The method includes the steps of: driving a probe to transmit an ultrasonic wave; receiving an echo, produced when the ultrasonic wave is reflected from a subject to be deformed periodically under stress, at the probe; figuring out a thickness change waveform, representing a variation in distance between two arbitrary measuring points on the subject, based on the received echo signal; generating a reference waveform; and obtaining subject's internal information by comparing the thickness change waveform and the reference waveform to each other.

Another control method according to the present invention is a method for controlling an ultrasonic diagnostic apparatus using a control section of the apparatus itself. The method includes the steps of: (A) driving a probe to transmit an ultrasonic wave; (B) receiving an echo, produced when the ultrasonic wave is reflected from a subject to be deformed periodically under stress, at the probe; (C) figuring out a thickness change waveform, representing a variation in distance between two arbitrary measuring points on the subject, based on the received echo signal; (D) generating a reference waveform; and (E) calculating the greatest variation in the thickness change waveform by comparing the reference waveform and the thickness change waveform to each other.

In one preferred embodiment, the step (E) includes calculating a coefficient to be multiplied by either the thickness change waveform or the reference waveform so as to minimize a matching error between the thickness change waveform and the reference waveform and calculating the greatest variation in the thickness change waveform based on the coefficient and the amplitude of the reference waveform.

In another preferred embodiment, the reference waveform is generated by calculating the average of thickness change waveforms that have been collected in advance from a plurality of subjects.

In still another preferred embodiment, the control method further includes the step of adjusting the period of the reference waveform to one deformation period of the subject. The step (E) includes calculating the greatest variation in the thickness change waveform based on the reference waveform, of which the period has been adjusted, and the thickness change waveform.

In yet another preferred embodiment, the control method further includes the step of adjusting the period of the thickness change waveform to one deformation period of the subject. The step (E) includes calculating the greatest thickness change in the thickness change waveform based on the thickness change waveform, of which the period has been adjusted, and the reference waveform.

In yet another preferred embodiment, the control method further includes the step of averaging the thickness change waveform, of which the period has been adjusted, over multiple periods. The greatest variation in the thickness change waveform is calculated based on the averaged thickness change waveform and the reference waveform.

In yet another preferred embodiment, the step (C) includes the steps of: figuring out a displacement waveform representing displacements of a plurality of measuring points on the subject based on the received echo signal, and figuring out the thickness change waveform between the two measuring points based on the displacement waveform.

In this particular preferred embodiment, the step (D) includes generating the reference waveform based on the displacement waveform.

In another preferred embodiment, the control method further includes the step of figuring out a waveform representing a variation in the vascular caliber of the subject based on the displacement waveform, and the step (D) includes generating the reference waveform based on the vascular caliber variation waveform.

In still another preferred embodiment, the step (D) includes generating the reference waveform based on a waveform representing a variation in the blood pressure of the subject.

In yet another preferred embodiment, the control method further includes the step of getting information about a difference in the stress that has been caused during a deformation period of the subject and calculating a modulus of elasticity based on the greatest variation.

Still another control method according to the present invention is a method for controlling an ultrasonic diagnostic apparatus using a control section of the apparatus itself. The method includes the steps of: (A) driving a probe to transmit an ultrasonic wave; (B) receiving an echo, produced when the ultrasonic wave is reflected from a subject to be deformed periodically under stress, at the probe; (C) figuring out a thickness change waveform, representing a variation in distance between two arbitrary measuring points on the subject, based on the received echo signal; (D) generating a reference waveform; (E) calculating the greatest thickness change and an index indicating a degree of matching between the thickness change waveform and the reference waveform by comparing the reference waveform and the thickness change waveform to each other; and (F) determining the reliability of the greatest thickness change based on the index.

In one preferred embodiment, the step (E) includes calculating the coefficient and a difference to be caused by the use of the coefficient so as to minimize the difference between one of the thickness change and reference waveforms and a waveform obtained by multiplying the other waveform by the coefficient. The step (E) also includes calculating the greatest thickness change in the thickness change waveform based on the coefficient and the amplitude of the reference waveform, thereby outputting the difference as the index.

In this particular preferred embodiment, the reference waveform is generated by calculating the average of thickness change waveforms that have been collected in advance from a plurality of subjects.

In a specific preferred embodiment, the control method further includes the step (G) of adjusting the period of the thickness change waveform to one deformation period of the subject, and the step (C) includes calculating the greatest thickness change in the thickness change waveform based on the thickness change waveform, of which the period has been adjusted, and the reference waveform.

In a more specific preferred embodiment, the control method further includes the step (H) of averaging the thickness change waveform, of which the period has been adjusted, over multiple periods, and the step (F) includes calculating the coefficient, the difference and the greatest thickness change based on the averaged thickness change waveform using the thickness change estimating section.

In this particular preferred embodiment, the step (H) includes calculating the variance of the thickness change waveform based on the average, and the step (F) includes determining the reliability of the greatest thickness change based on the variance and the difference.

In a specific preferred embodiment, the step (F) includes determining the reliability of the greatest thickness change based on the variance, the coefficient and the difference.

Yet another control method according to the present invention is a method for controlling an ultrasonic diagnostic apparatus using a control section of the apparatus itself. The method includes the steps of: driving a probe to transmit an ultrasonic wave; receiving an echo, produced when the ultrasonic wave is reflected from a subject to be deformed periodically under stress, at the probe; figuring out a thickness change waveform, representing a variation in distance between two arbitrary measuring points on the subject, based on the received echo signal; adjusting the period of the thickness change waveform to one deformation period of the subject; calculating the average and the variance of the thickness change waveform, of which the period has been adjusted, over multiple periods; generating a reference waveform; calculating the greatest thickness change by comparing the reference waveform and the averaged thickness change waveform to each other; and determining the reliability of the greatest thickness change based on the variance.

In one preferred embodiment, the step of calculating the greatest thickness change includes calculating the coefficient so as to minimize a difference between one of the averaged thickness change and reference waveforms and a waveform obtained by multiplying the other waveform by the coefficient, and also includes calculating the greatest thickness change in the thickness change waveform based on the coefficient and the amplitude of the reference waveform.

In this particular preferred embodiment, the step of determining includes determining the reliability of the greatest thickness change based on the variance and the coefficient.

In another preferred embodiment, the control method further includes the steps of: getting information about a difference in the stress that has been caused during a deformation period of the subject and calculating a modulus of elasticity based on the greatest thickness change; and displaying the modulus of elasticity according to the degree of reliability that has been determined.

Yet another control method according to the present invention is a method for controlling an ultrasonic diagnostic apparatus using a control section of the apparatus itself. The method includes the steps of: (A) driving a probe to transmit an ultrasonic wave; (B) receiving an echo, produced when the ultrasonic wave is reflected from a subject that includes multiple different tissues and that is deformed periodically under stress, at the probe; (C) figuring out a thickness change waveform, representing a variation in distance between two arbitrary measuring points on the subject, based on the received echo signal; (D) generating multiple reference waveforms associated with the respective tissues; (E) calculating an index indicating the degree of matching between the thickness change waveform and each said reference waveform by comparing the reference waveform and the thickness change waveform to each other; and (F) determining, based on the indices, to which of the multiple tissues the tissue that has been located between the two measuring points and produced the thickness change waveform corresponds.

In one preferred embodiment, the step (E) includes calculating the coefficient and a difference to be caused by the use of the coefficient so as to minimize the difference between one of the thickness change and reference waveforms and a waveform obtained by multiplying the other waveform by the coefficient, and also includes calculating the greatest thickness change in the thickness change waveform for use of each said reference waveform based on the coefficient and the amplitude of the reference waveform.

In this particular preferred embodiment, the step (E) includes outputting each said difference as the index, and the step (F) includes identifying a tissue associated with one of the reference waveforms that has caused the smallest difference as the tissue that has produced the thickness change waveform between the two measuring points and outputting the greatest thickness change that has been calculated based on the reference waveform.

In a specific preferred embodiment, the control method further includes the step (G) of calculating a modulus of elasticity based on information about a difference in the stress that has been caused during a deformation period of the subject and on the greatest thickness change that has been calculated in the step (F).

In another preferred embodiment, the reference waveform is generated by calculating the average of thickness change waveforms that have been collected in advance from multiple tissues of a plurality of subjects.

In still another preferred embodiment, the control method further includes the step (H) of generating image data representing the modulus of elasticity based on a result obtained in the step (F).

In yet another preferred embodiment, if each said difference is greater than a predetermined value, the step (F) includes identifying the tissue that has produced the thickness change waveform between the two measuring points as none of the tissues.

Yet another control method according to the present invention is a method for controlling an ultrasonic diagnostic apparatus using a control section of the apparatus itself. The method includes the steps of: (A) driving a probe to transmit an ultrasonic wave; (B) receiving an echo, produced when the ultrasonic wave is reflected from a subject to be deformed periodically under stress, at the probe; (C) figuring out a thickness change waveform, representing a variation in distance between two arbitrary measuring points on the subject, based on the received echo signal; (D) generating a plurality of viscosity property reference waveforms; (E) calculating a viscosity property index, indicating the degree of matching between the thickness change waveform and each said viscosity property reference waveform, by comparing the viscosity property reference waveform and the thickness change waveform to each other; and (F) determining the viscosity coefficient by the viscosity property index.

In one preferred embodiment, the viscosity property reference waveform is a strain waveform of the subject that has been obtained based on information about a variation in the stress of the subject who is supposed to have a predetermined viscosity coefficient. The step (F) includes outputting the viscosity coefficient associated with the viscosity property reference waveform in which the smallest one of the viscosity property indices is obtained.

In this particular preferred embodiment, the step (E) includes outputting, as the viscosity property index, a difference in a situation where the coefficient is determined so as to minimize the difference between a waveform obtained by multiplying one of the thickness change and each said viscosity property reference waveforms by a first coefficient and the other waveform.

In a specific preferred embodiment, the information about the subject's stress variation is a waveform representing the blood pressure of the subject.

In another preferred embodiment, the step (C) includes the steps of: figuring out a displacement waveform representing displacements of a plurality of measuring points on the subject based on the received echo signal, and figuring out the thickness change waveform between the two measuring points based on the displacement waveform.

In still another preferred embodiment, the control method further includes the step (H) of figuring out a waveform representing a variation in the vascular caliber of the subject based on the displacement waveform. The information about the subject's stress variation is obtained by correcting the vascular caliber waveform with the highest and lowest blood pressure values of the subject.

In yet another preferred embodiment, the step (C) includes generating a waveform representing a variation in the thickness of the subject's blood vessel wall in the vicinity of his or her vascular lumen, and the step (D) includes correcting the waveform representing the thickness change near the vascular lumen with the highest and lowest blood pressure values of the subject, and using the corrected waveform as the information about the subject's stress variation.

In yet another preferred embodiment, the step (D) includes further generating an elastic property reference waveform, and the step (E) includes calculating the greatest thickness change in the thickness change waveform by comparing the elastic property reference waveform and the thickness change waveform to each other.

In this particular preferred embodiment, the step (E) includes determining a second coefficient so as to minimize a difference between a waveform obtained by multiplying one of the thickness change and elastic property reference waveforms by the second coefficient and the other waveform, and calculating the greatest thickness change based on the second coefficient and the amplitude of the elastic property reference waveform.

In a specific preferred embodiment, the control method further includes the step (I) of getting information about a difference in the stress that has been caused during a deformation period of the subject and calculating a modulus of elasticity based on the greatest variation.

In yet another preferred embodiment, the step (D) includes generating the elastic property reference waveform based on a waveform representing a variation in the blood pressure of the subject.

Effects of the Invention

According to the present invention, information about a subject's internal tissue is obtained by comparing a thickness change waveform to a reference waveform. By comparing these waveforms, even if noise were superposed on the thickness change waveform abruptly, information about the subject's internal tissue, including more accurate greatest thickness change and a modulus of elasticity, should be obtained. Consequently, the ultrasonic diagnostic apparatus of the present invention can evaluate an attribute property such as a modulus of elasticity with high reliability and high precision.

Also, since the modulus of elasticity that has been calculated based on an index indicating the degree of matching between the reference waveform and the thickness change waveform has its reliability determined, a highly reliable modulus of elasticity can be obtained.

Furthermore, since it is determined which tissue has the modulus of elasticity obtained, the tissue on which the modulus of elasticity was measured can be identified, too.

Besides, since the viscosity coefficient is estimated by comparing the thickness change waveform to the reference waveform, the difference in the subject's tissue can be sensed based on the estimated viscosity coefficient. Consequently, even a tissue that has been hard to identify by a modulus of elasticity can now be identified.

Figure 6:
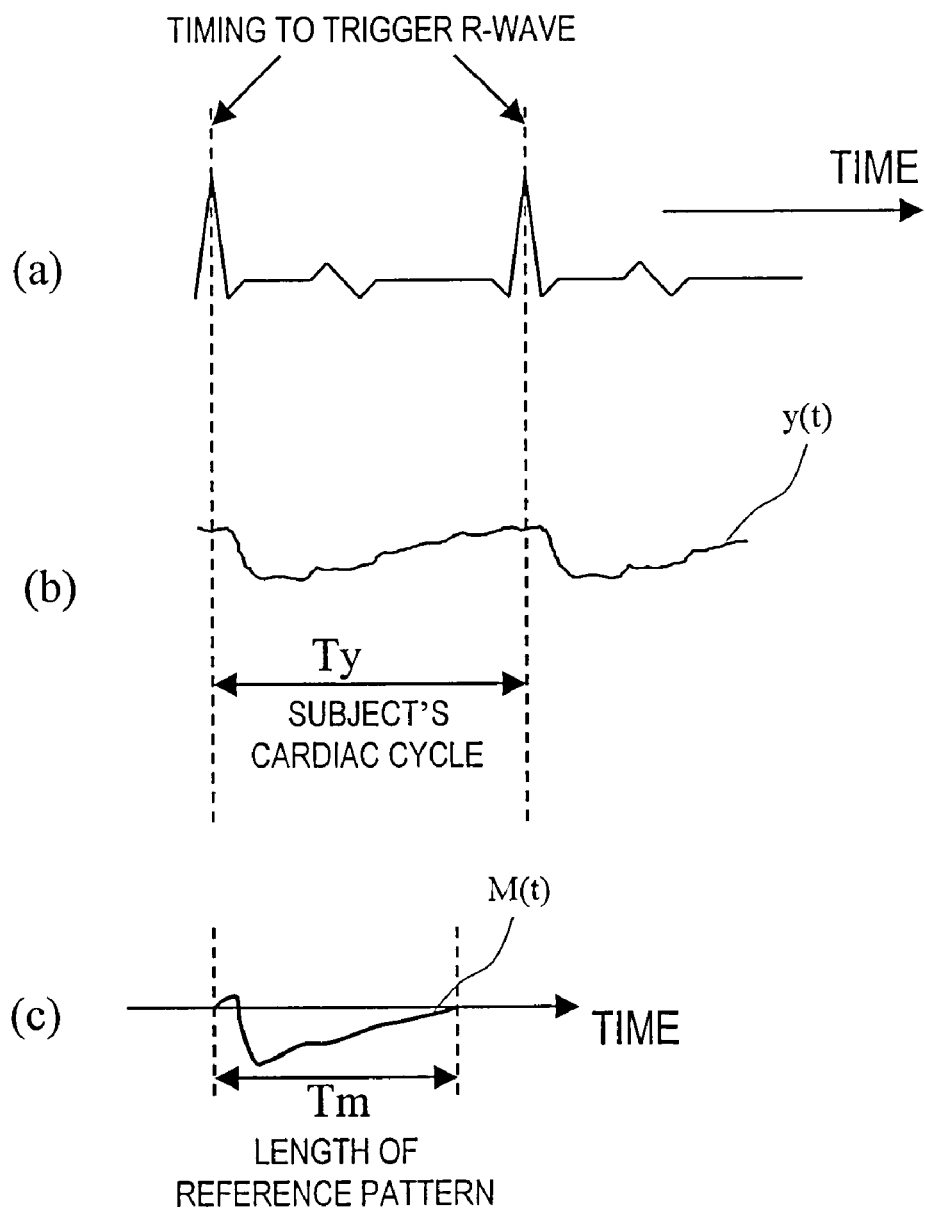

Portions (a), (b) and (c) of FIG. 6 show an electrocardiogram provided by a period detecting section, a thickness change waveform figured out by a thickness change waveform calculating section, and a reference waveform figured out by a reference waveform generating section in the second preferred embodiment.

Figure 7:
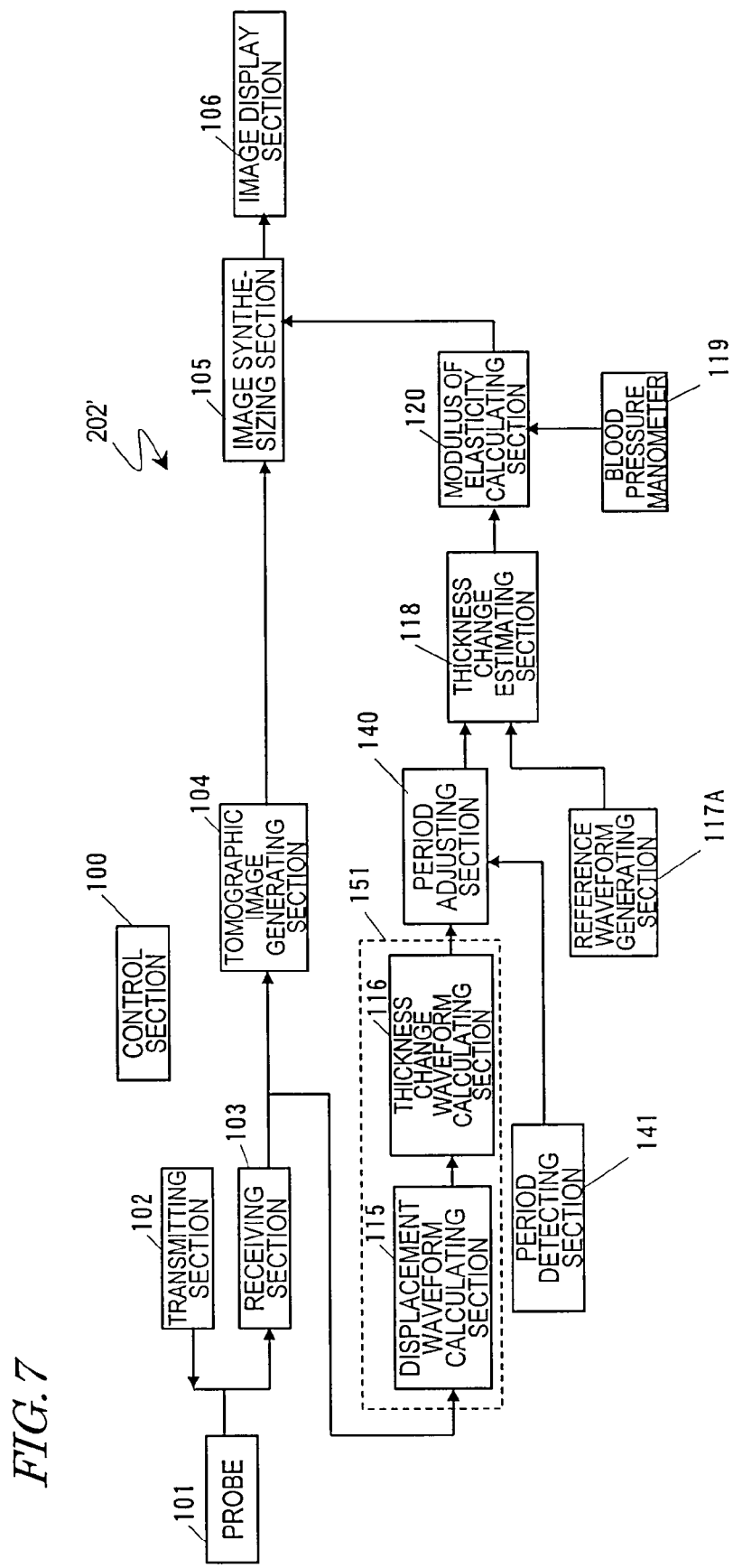

FIG. 7 is a block diagram showing a modified example of the second preferred embodiment of the ultrasonic diagnostic apparatus according to the present invention.

Figure 8:
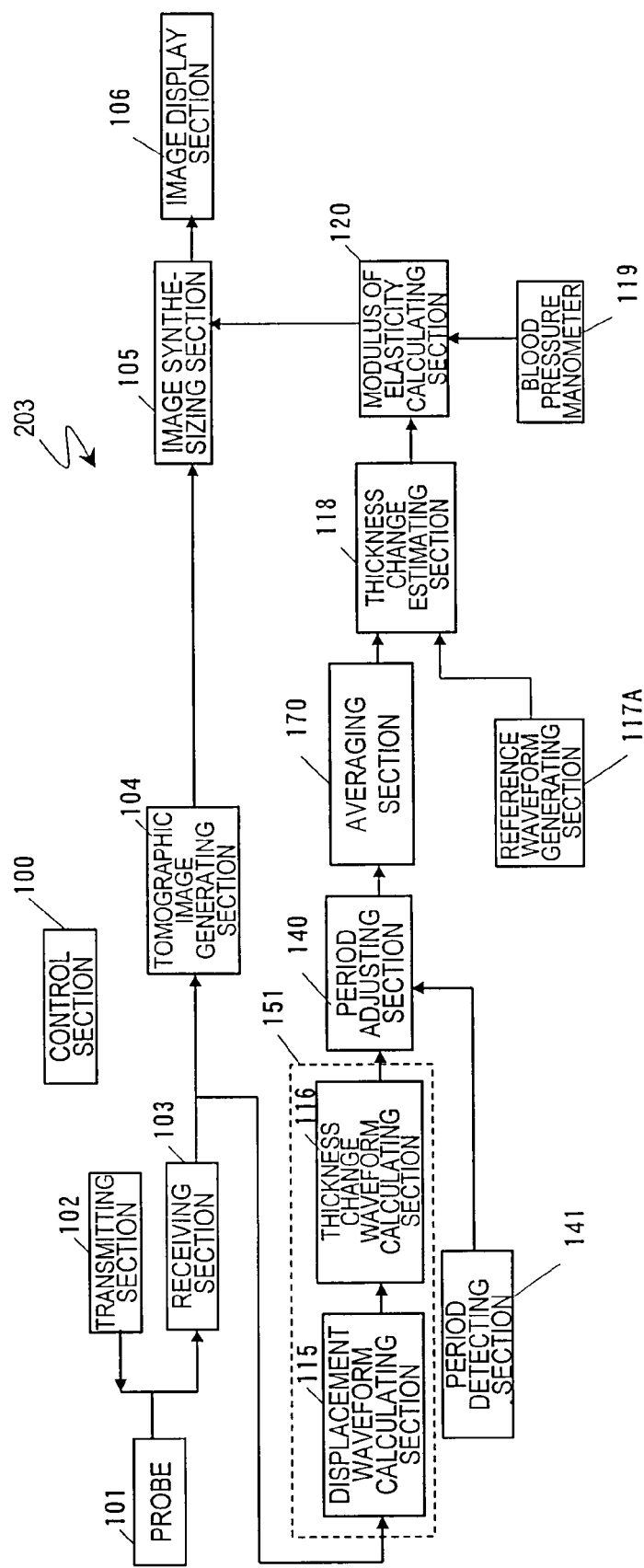

FIG. 8 is a block diagram showing a third preferred embodiment of an ultrasonic diagnostic apparatus according to the present invention.

Figure 9:
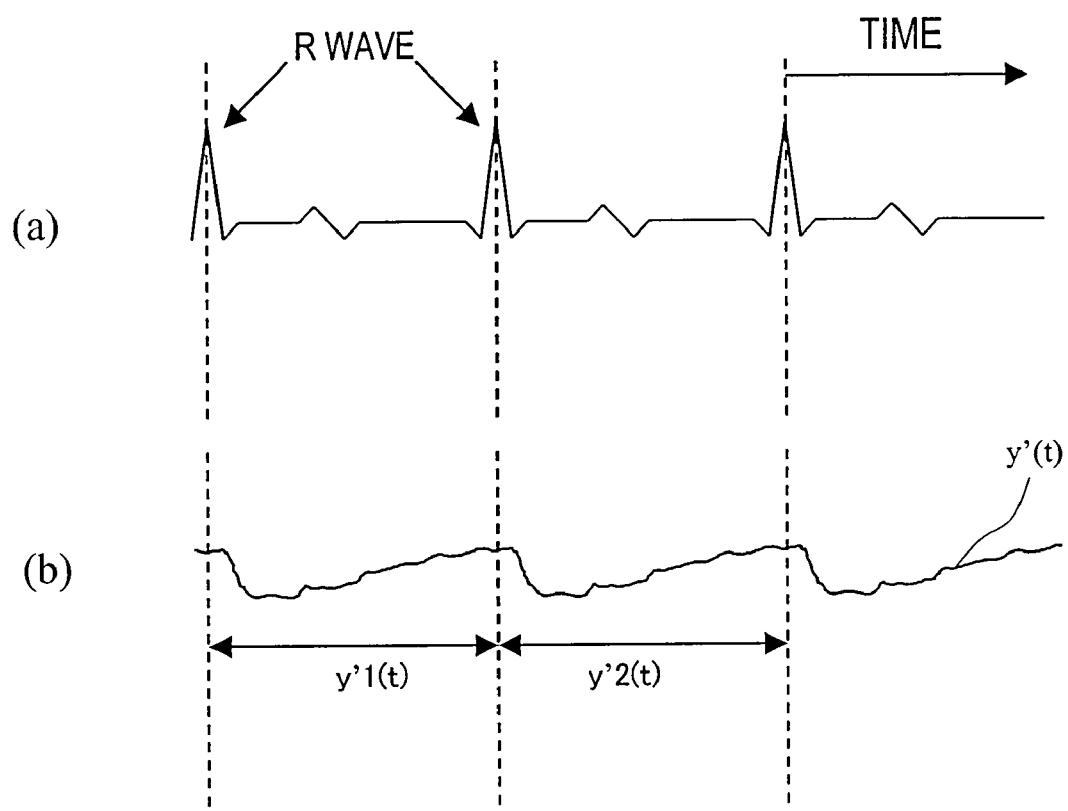

Portions (a) and (b) of FIG. 9 show an electrocardiogram provided by a period detecting section and a thickness change waveform provided by a period adjusting section in the third preferred embodiment.

Figure 10:
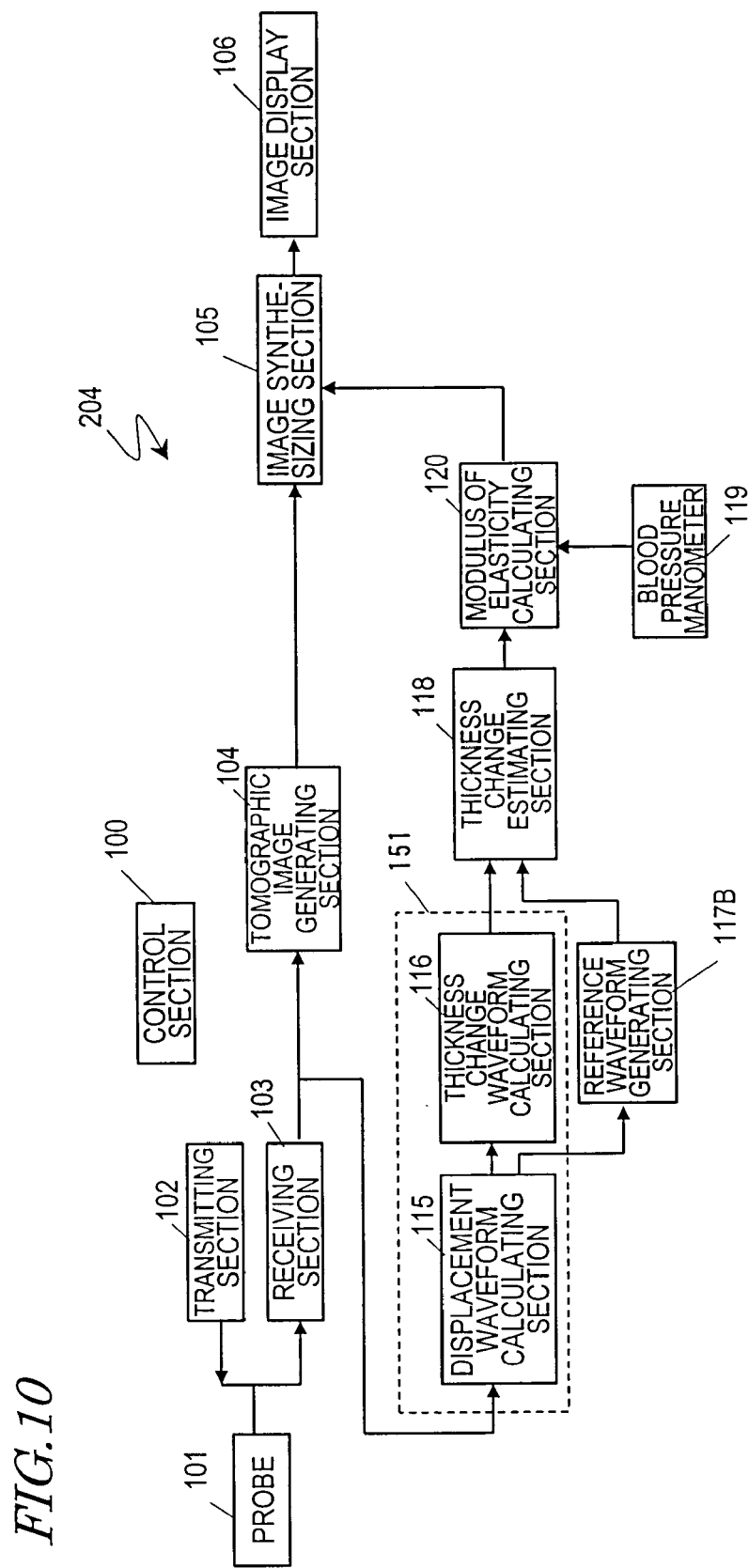

FIG. 10 is a block diagram showing a fourth preferred embodiment of an ultrasonic diagnostic apparatus according to the present invention.

FIG. 11 schematically illustrates a cross section of a subject under measurement with a probe.

FIGS. 12(a) and 12(b) show a displacement waveform input to a reference waveform generating section and a reference waveform generated by the reference waveform generating section, respectively, in the fourth preferred embodiment.

FIG. 13 shows a thickness change waveform output by a thickness change waveform calculating section in the fourth preferred embodiment.

Figure 14:
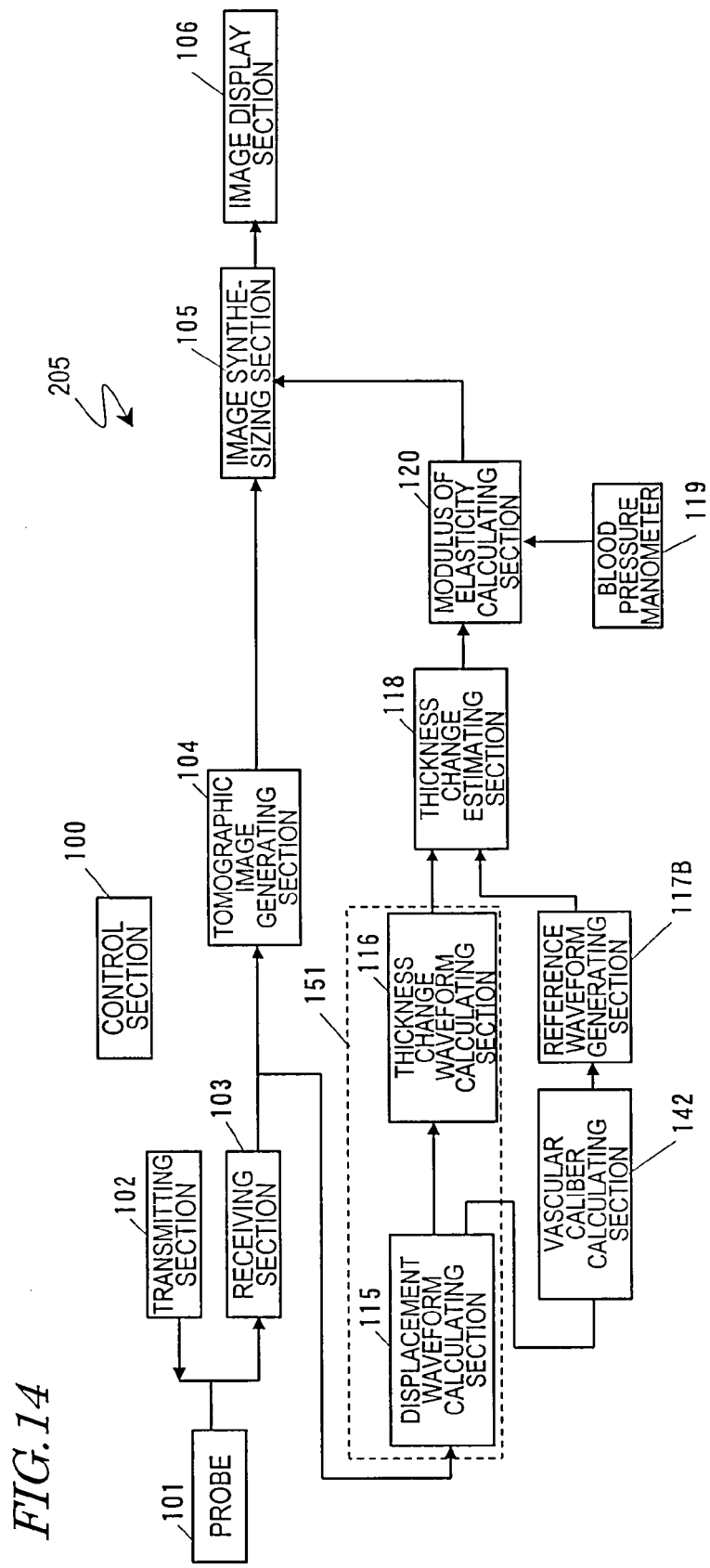

FIG. 14 is a block diagram showing a fifth preferred embodiment of an ultrasonic diagnostic apparatus according to the present invention.

Figure 15:
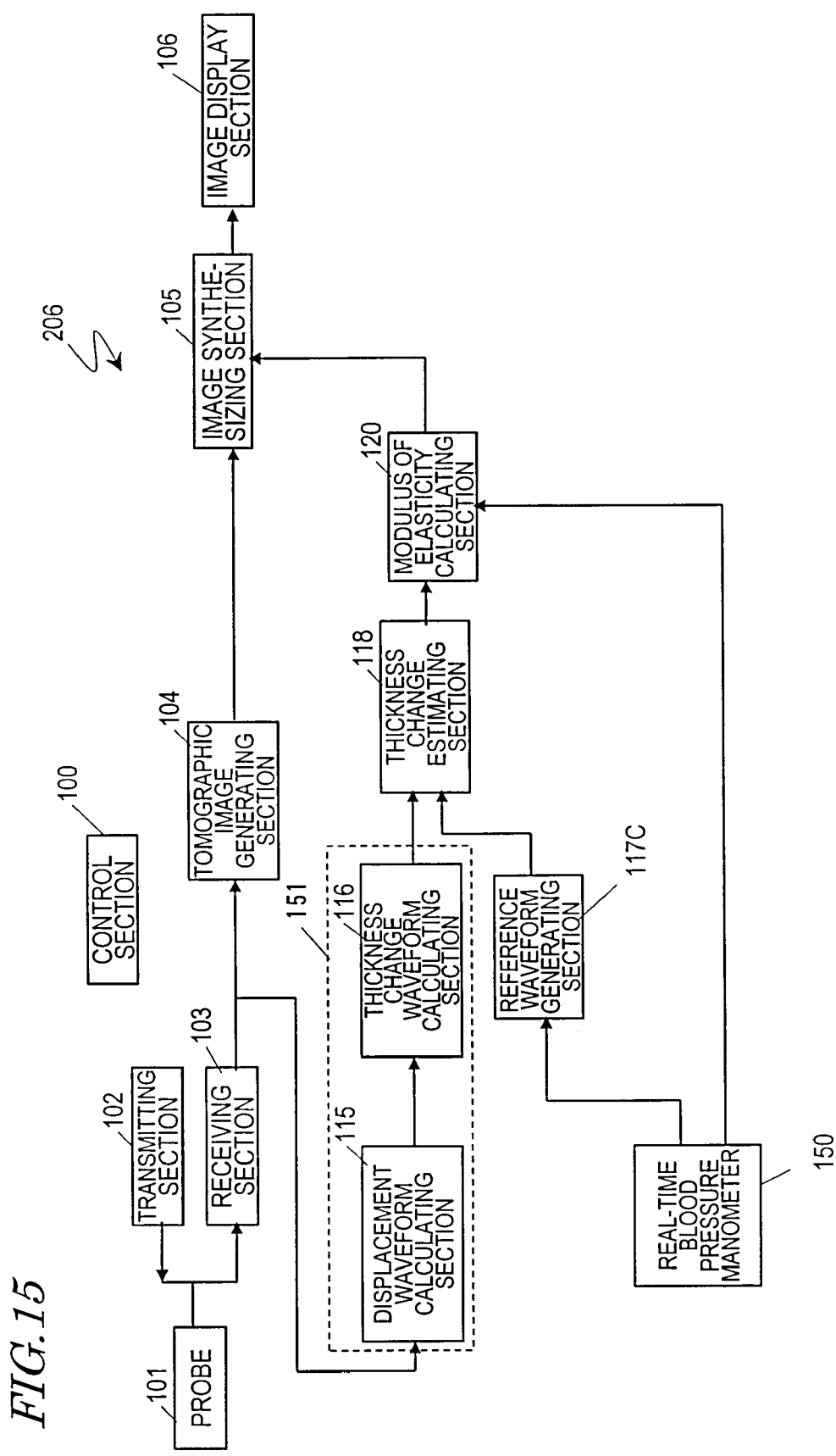

FIG. 15 is a block diagram showing a sixth preferred embodiment of an ultrasonic diagnostic apparatus according to the present invention.

Figure 16:

FIG. 16 shows an example of a blood pressure waveform for use in the sixth preferred embodiment.

Figure 17:
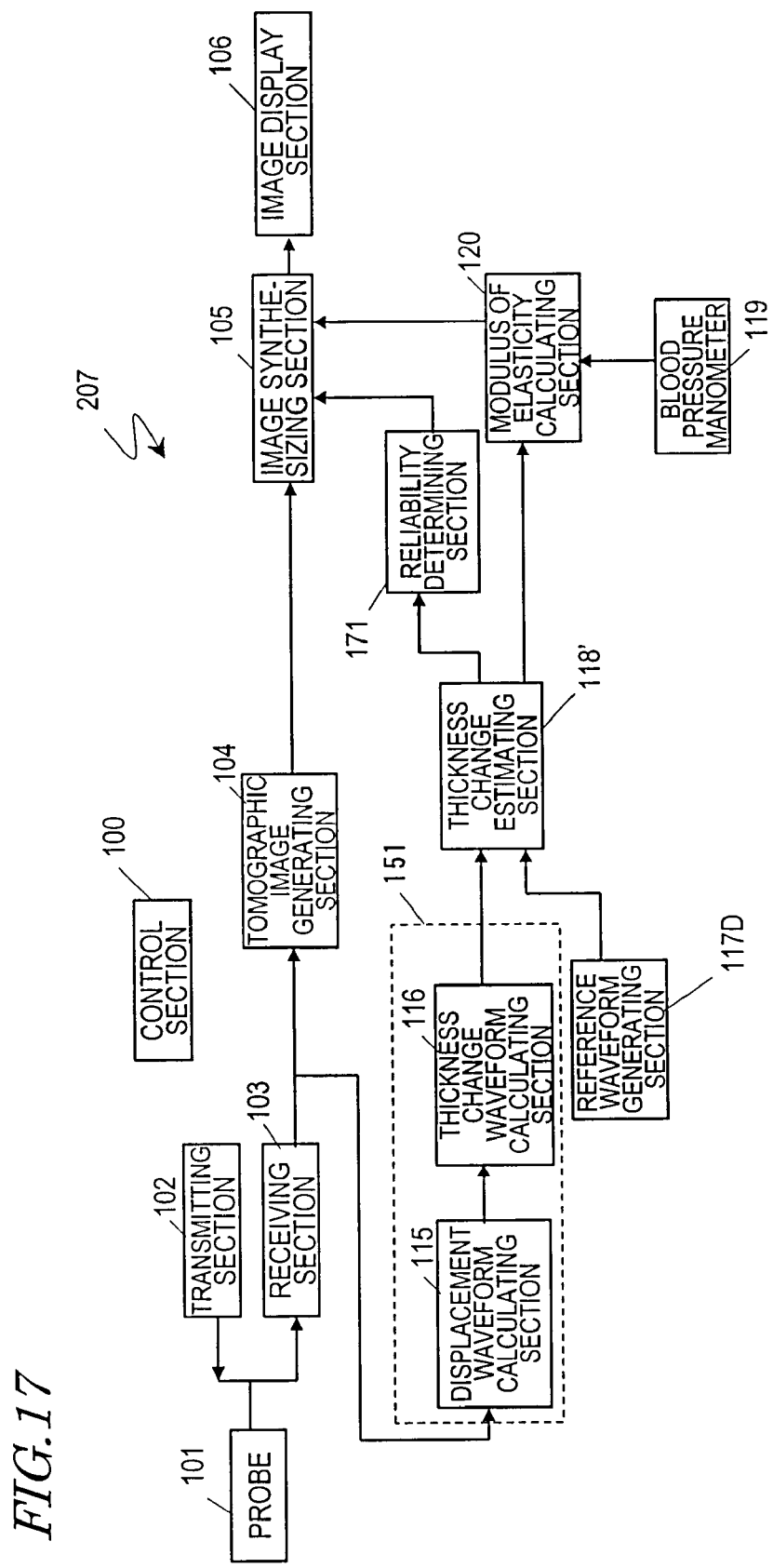

FIG. 17 is a block diagram showing a seventh preferred embodiment of an ultrasonic diagnostic apparatus according to the present invention.

Figure 18:
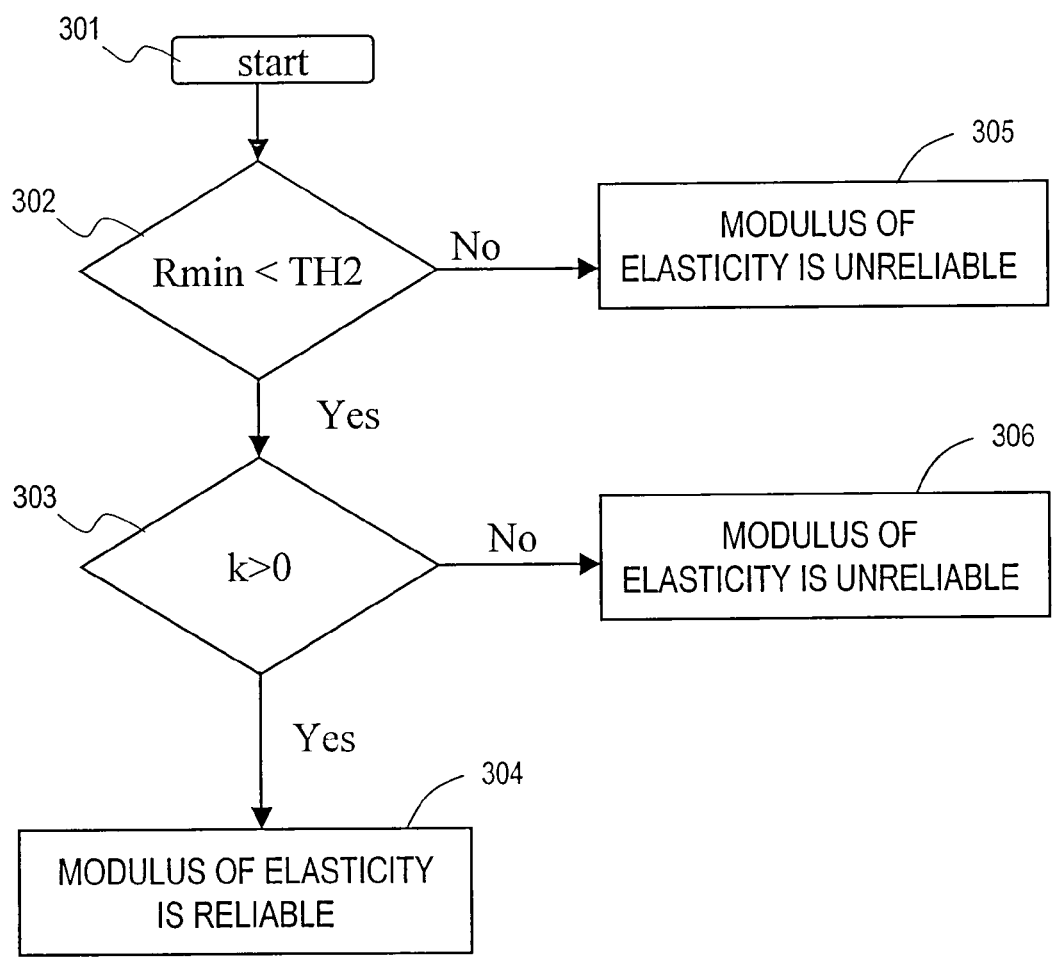

FIG. 18 is a flowchart showing how the reliability determining section of the seventh preferred embodiment operates.

Figure 19:
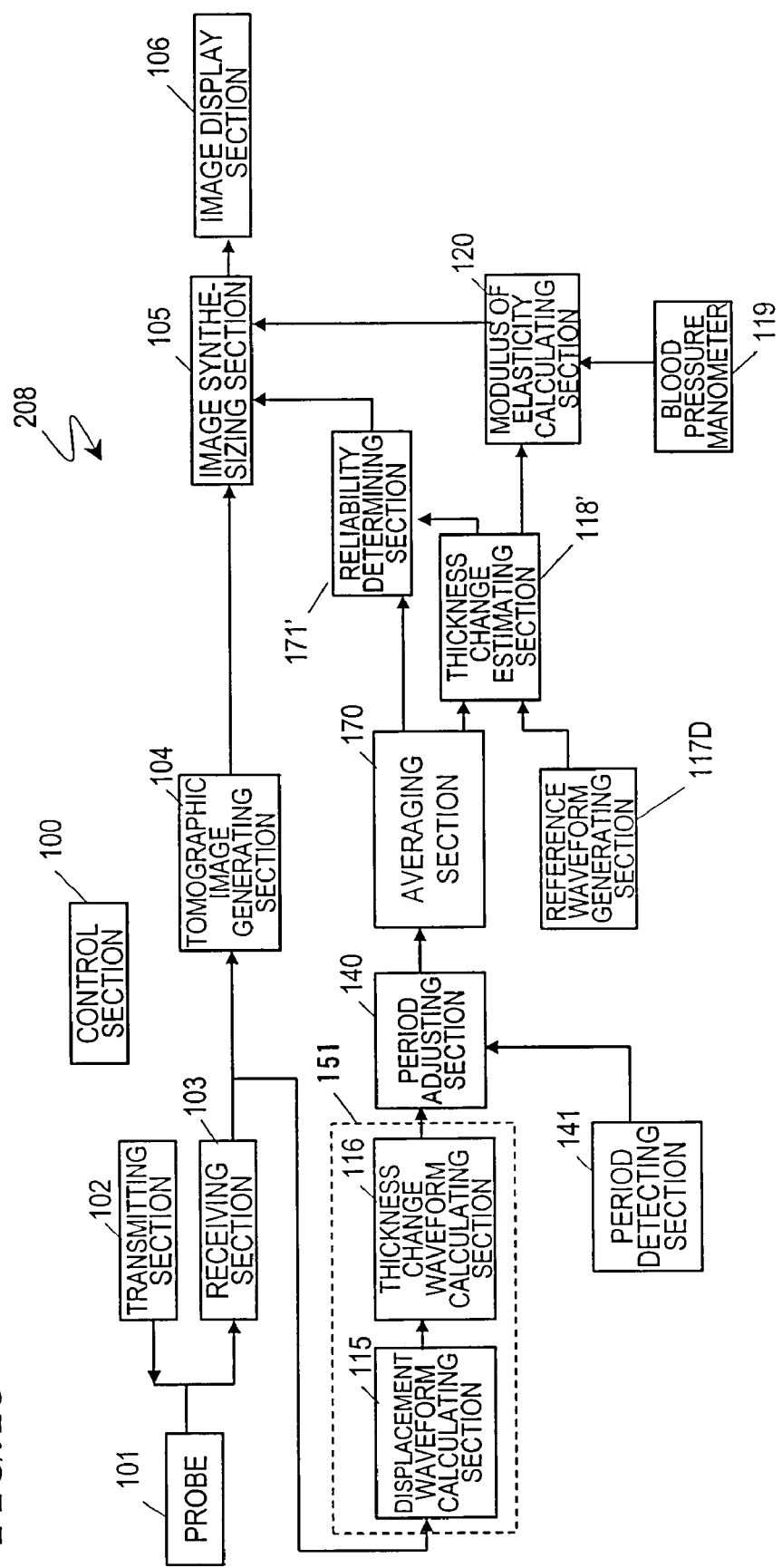

FIG. 19 is a block diagram showing an eighth preferred embodiment of an ultrasonic diagnostic apparatus according to the present invention.

FIGS. 20(a) and 20(b) show how to calculate the average of thickness change waveforms.

Figure 21:
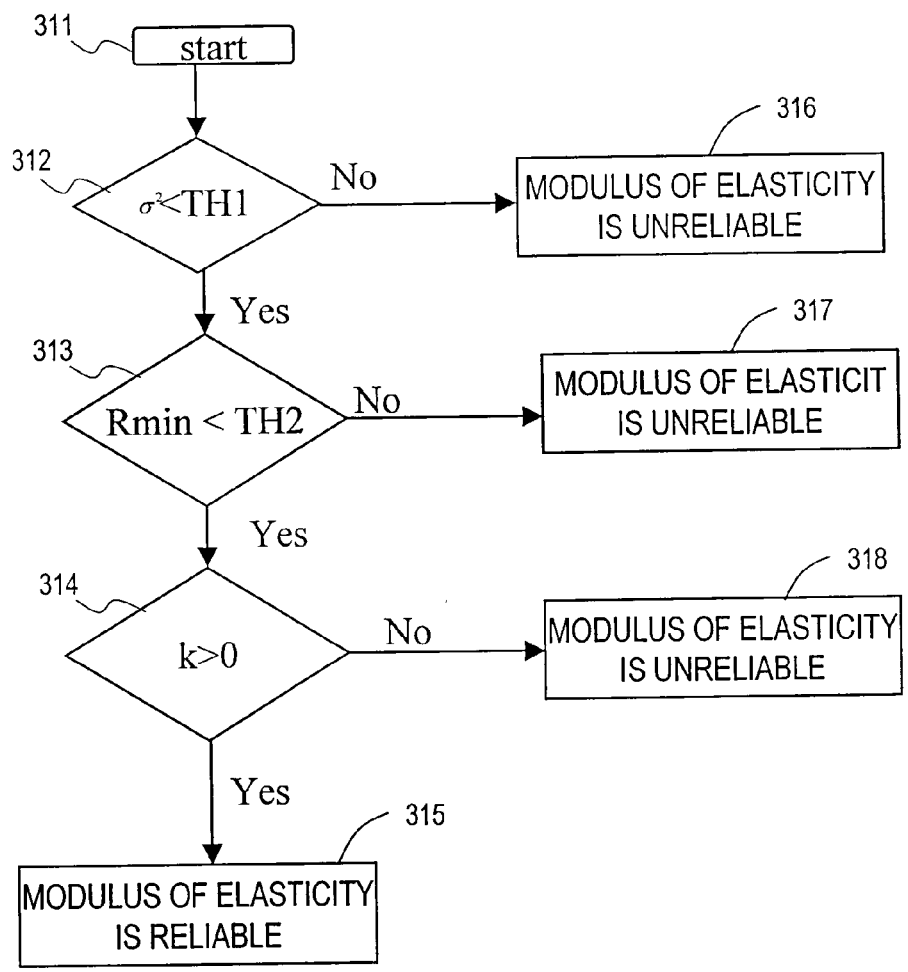

FIG. 21 is a flowchart showing how the reliability determining section of the eighth preferred embodiment operates.

Figure 22:
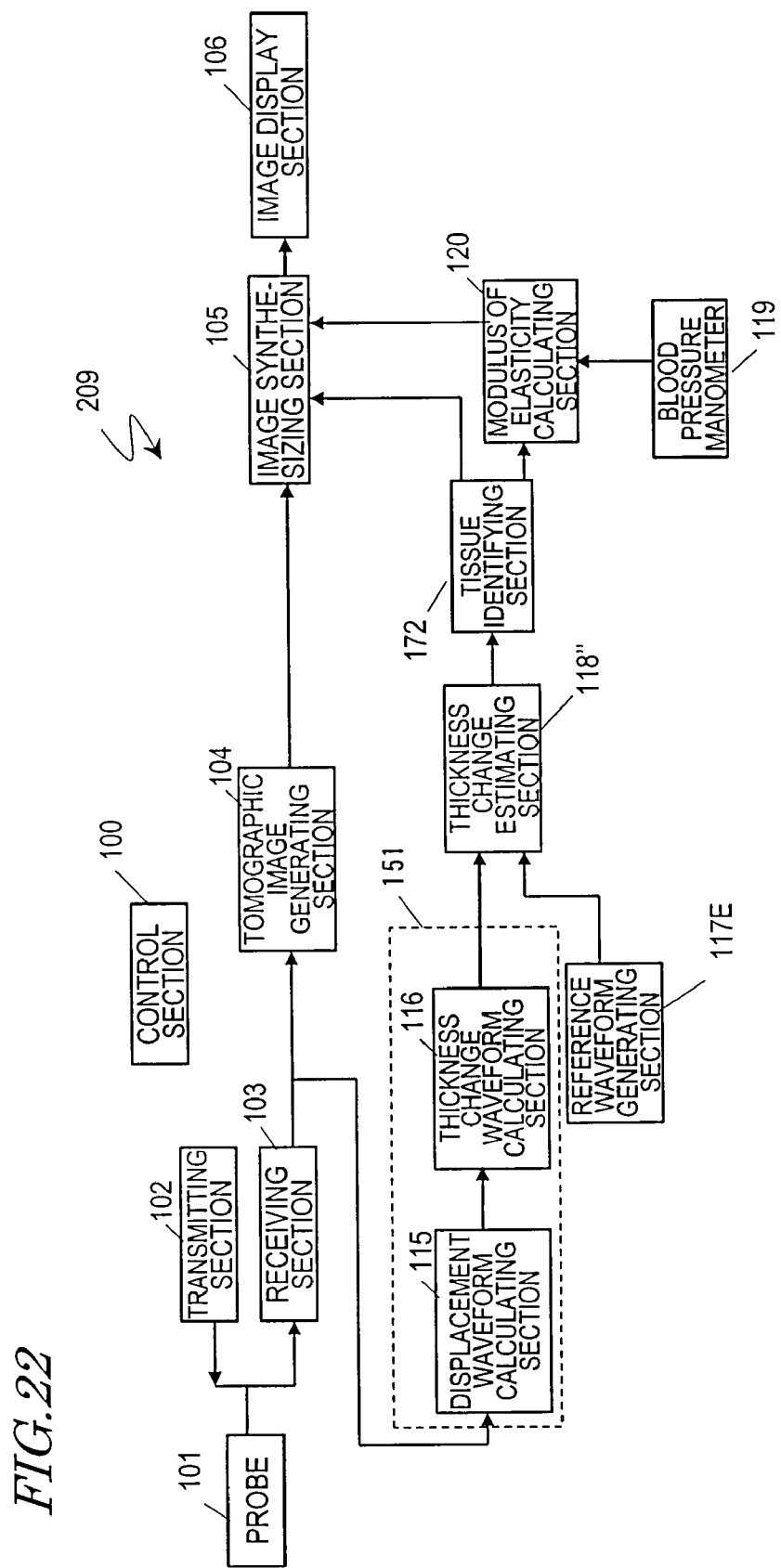

FIG. 22 is a block diagram showing a ninth preferred embodiment of an ultrasonic diagnostic apparatus according to the present invention.

Figure 23:
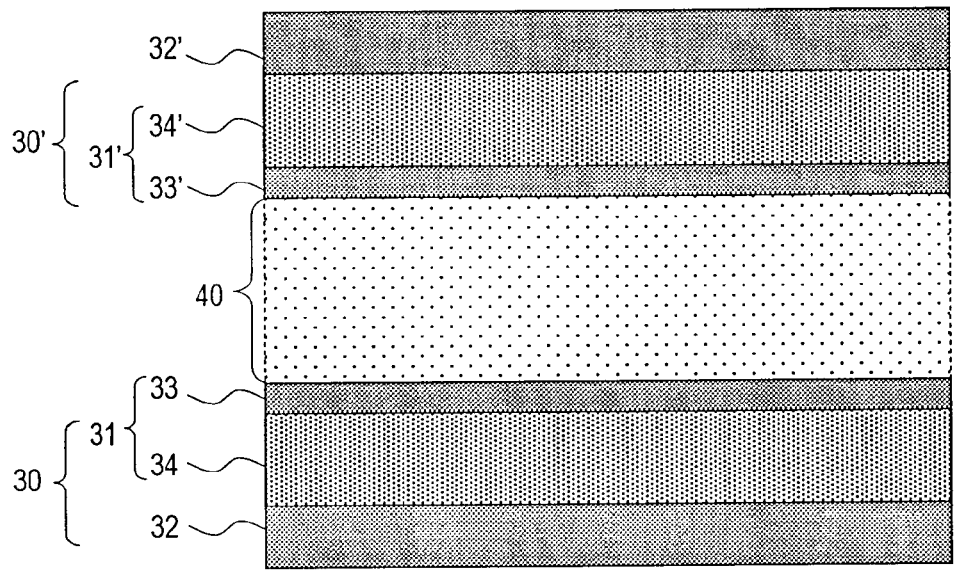

FIG. 23 schematically illustrates a cross-sectional structure of vessel wall as a subject.

Figure 24:
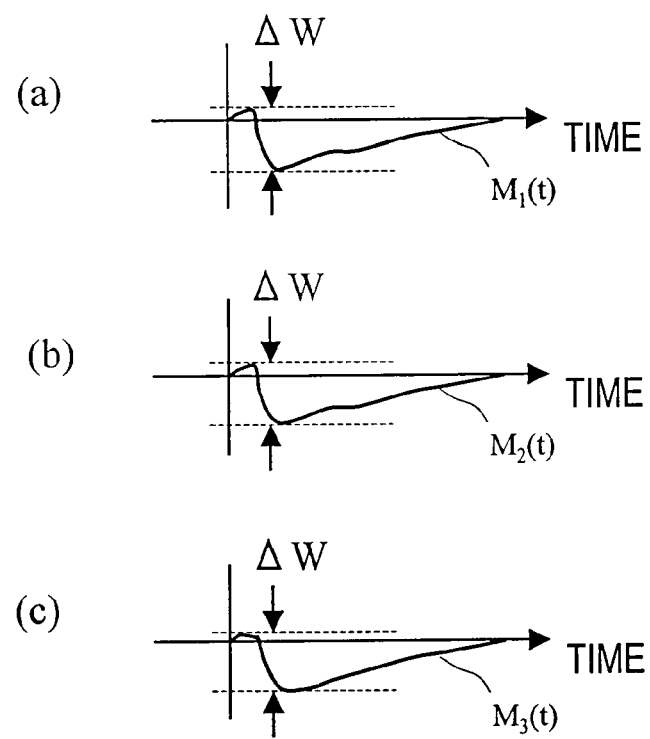

FIGS. 24(a), 24(b) and 24(c) show the respective reference waveforms of an intima, a media and an adventitia of a vessel wall.

Figure 25:
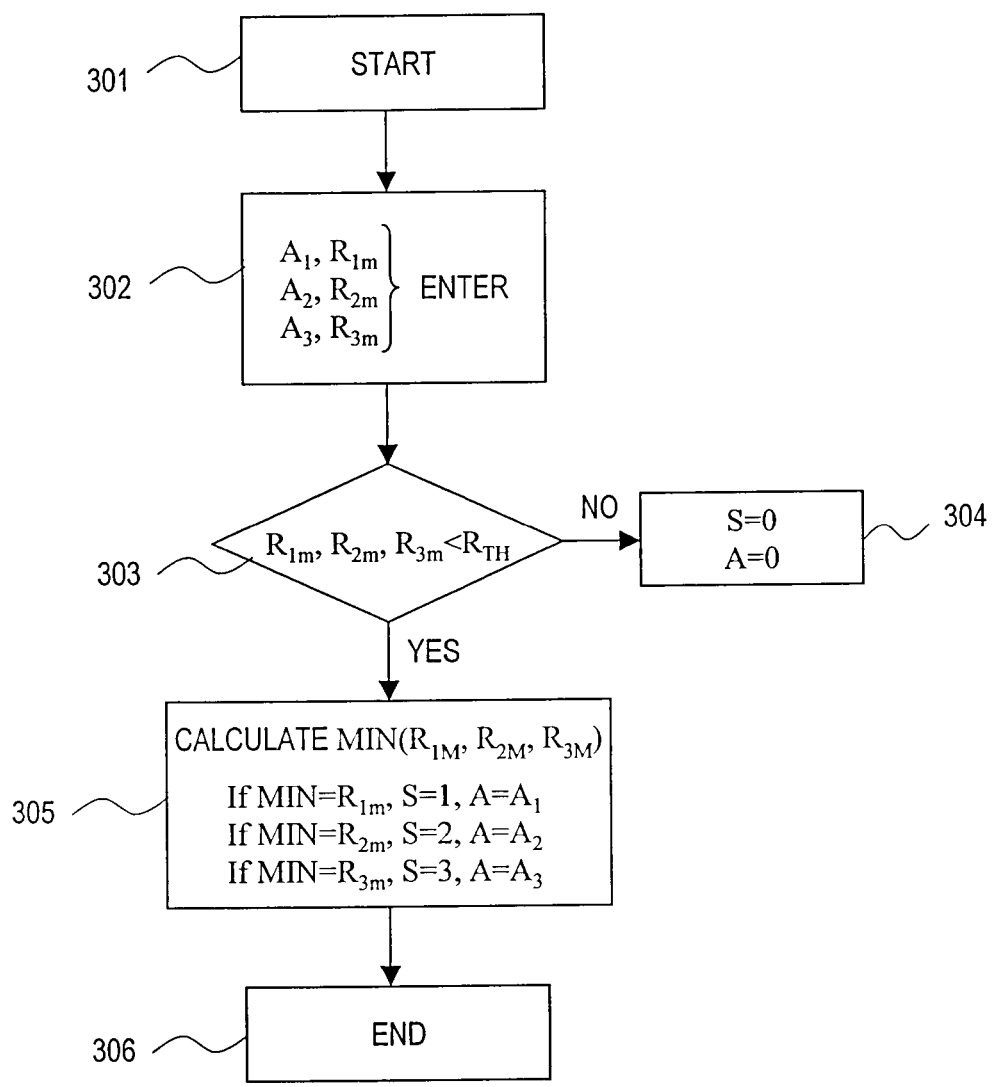

FIG. 25 is a flowchart showing how a tissue identifying section operates.

Figure 26:
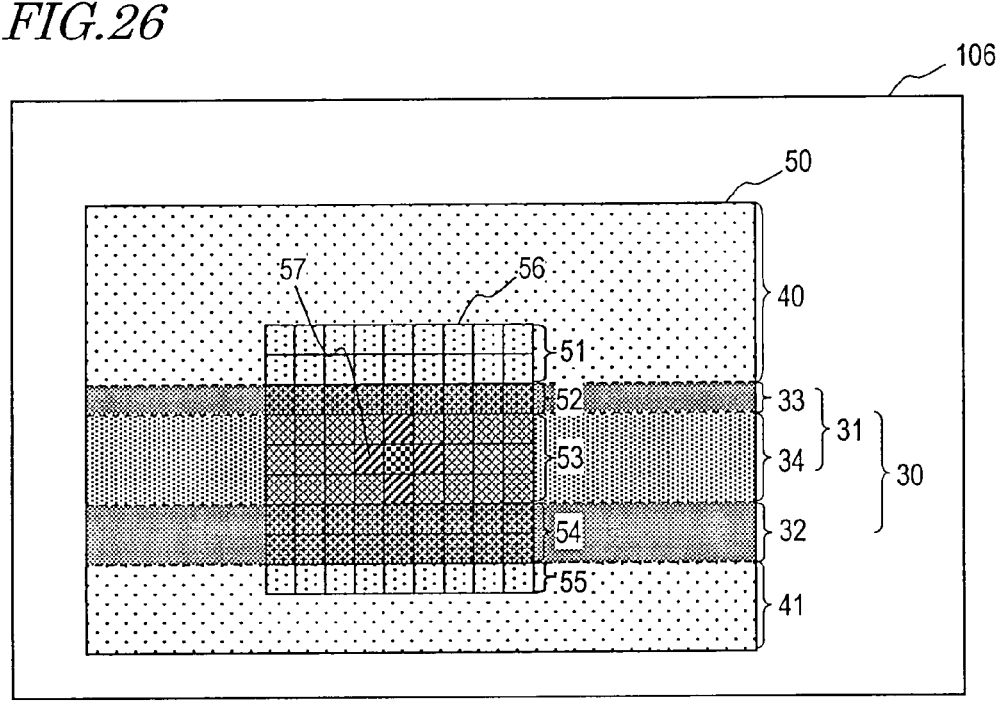

FIG. 26 shows an example of a two-dimensional map image representing moduli of elasticity on an image display section.

Figure 27:
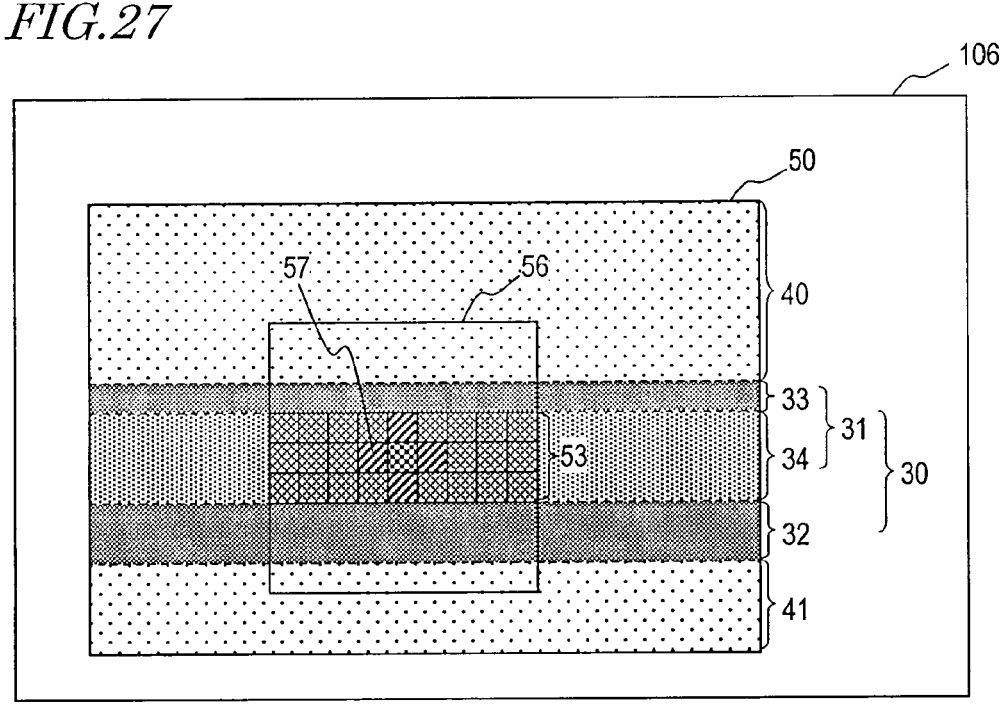

FIG. 27 shows another example of a two-dimensional map image representing moduli of elasticity on the image display section.

Figure 28:
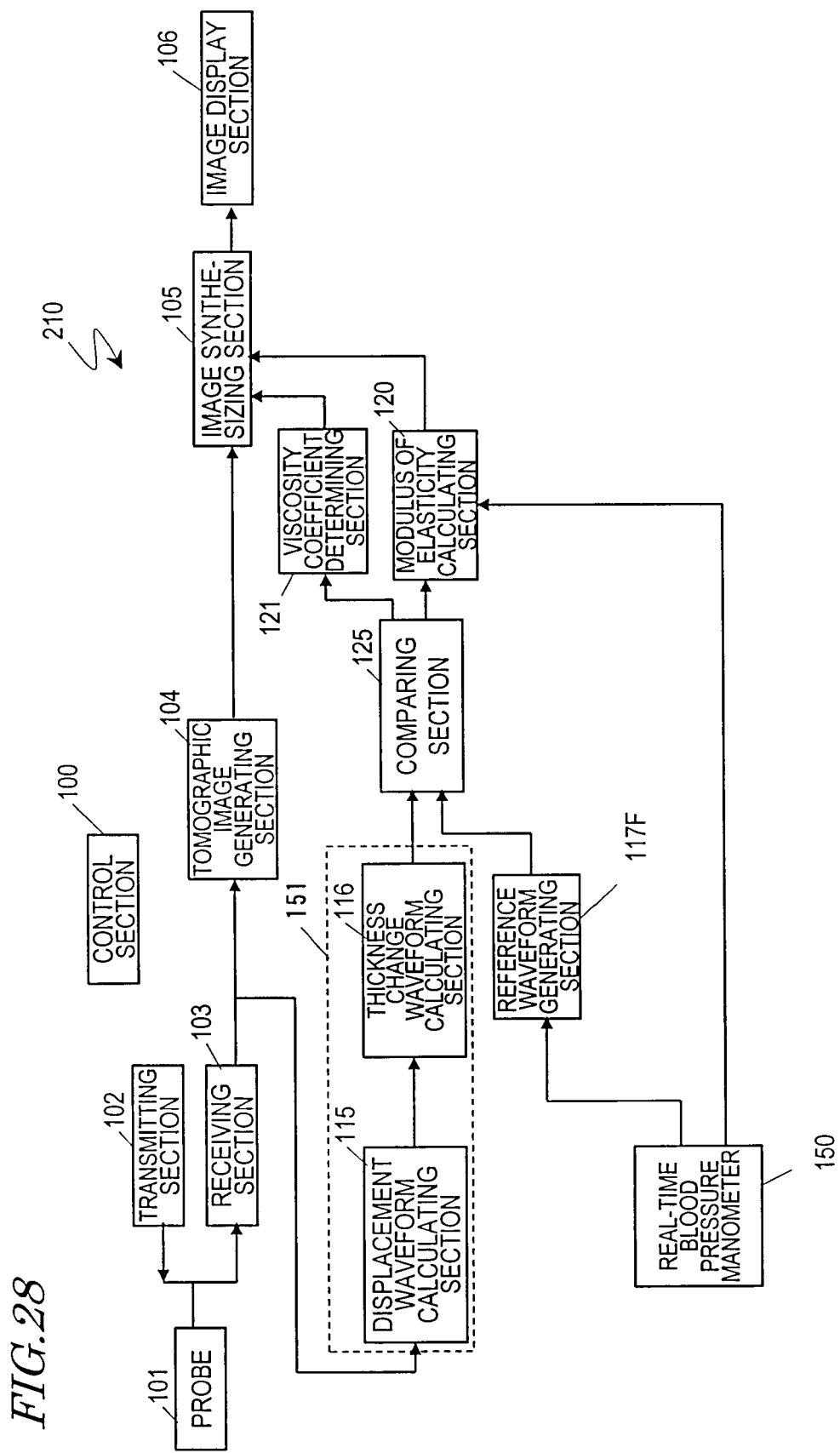

FIG. 28 is a block diagram showing a tenth preferred embodiment of an ultrasonic diagnostic apparatus according to the present invention.

Figure 29:
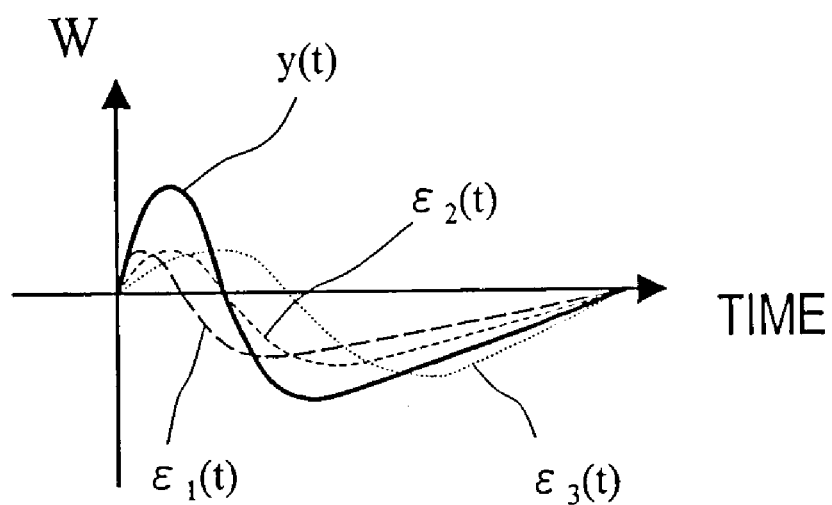

FIG. 29 shows how to calculate a viscosity coefficient.

Figure 30:
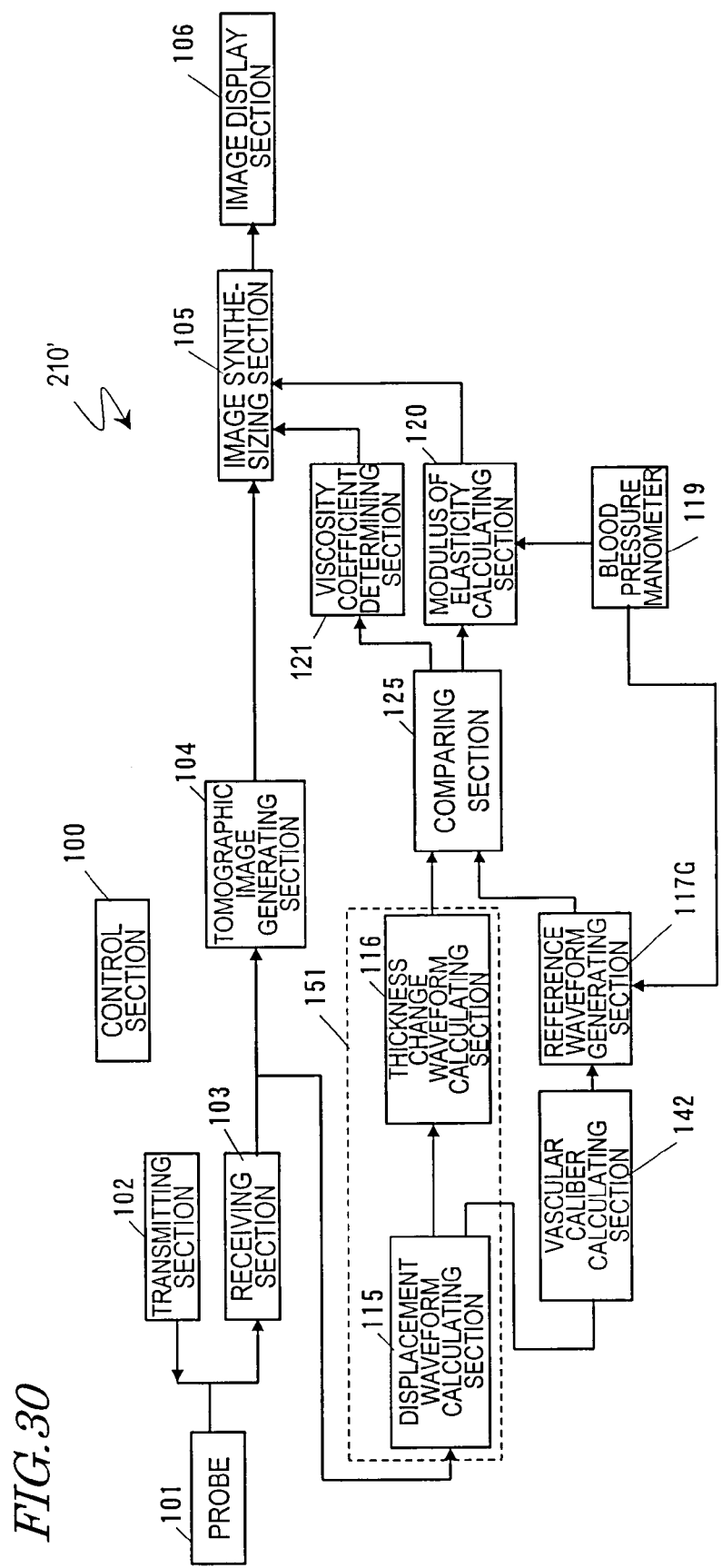

FIG. 30 is a block diagram showing an alternative configuration for the tenth preferred embodiment.

Figure 31:
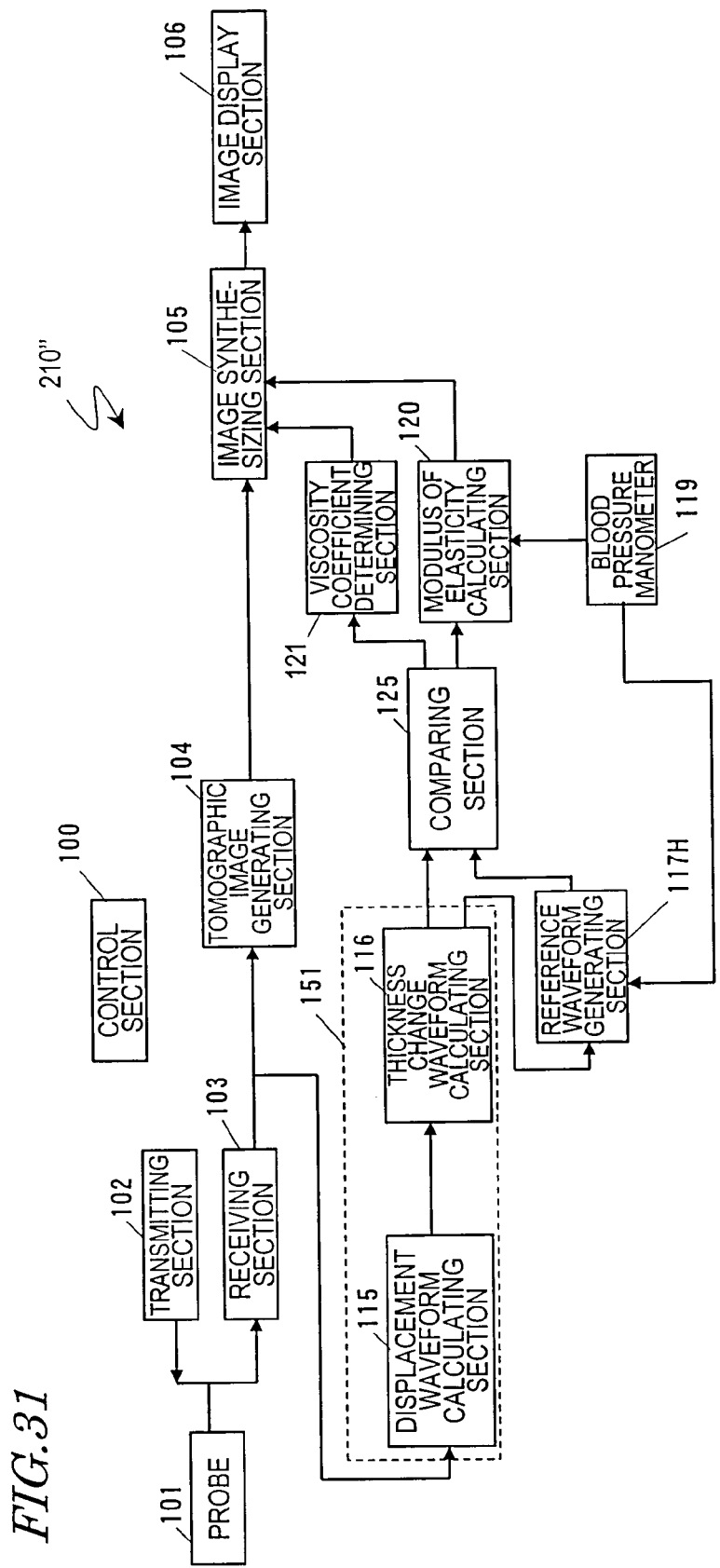

FIG. 31 is a block diagram showing another alternative configuration for the tenth preferred embodiment.

Figure 32:
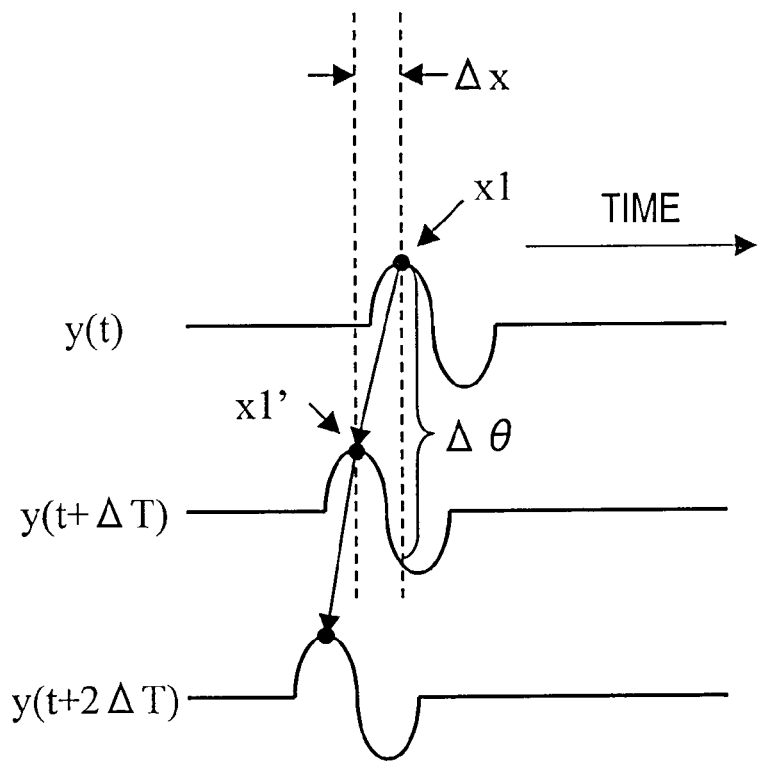

FIG. 32 shows how to track the motions of a tissue based on the phase difference of an ultrasonic echo signal.

Figure 33:
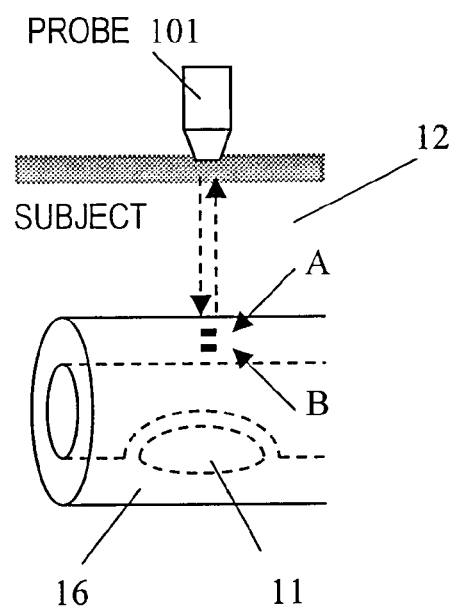

FIG. 33 schematically illustrates a cross section of a subject under measurement with a probe.

Figure 34:
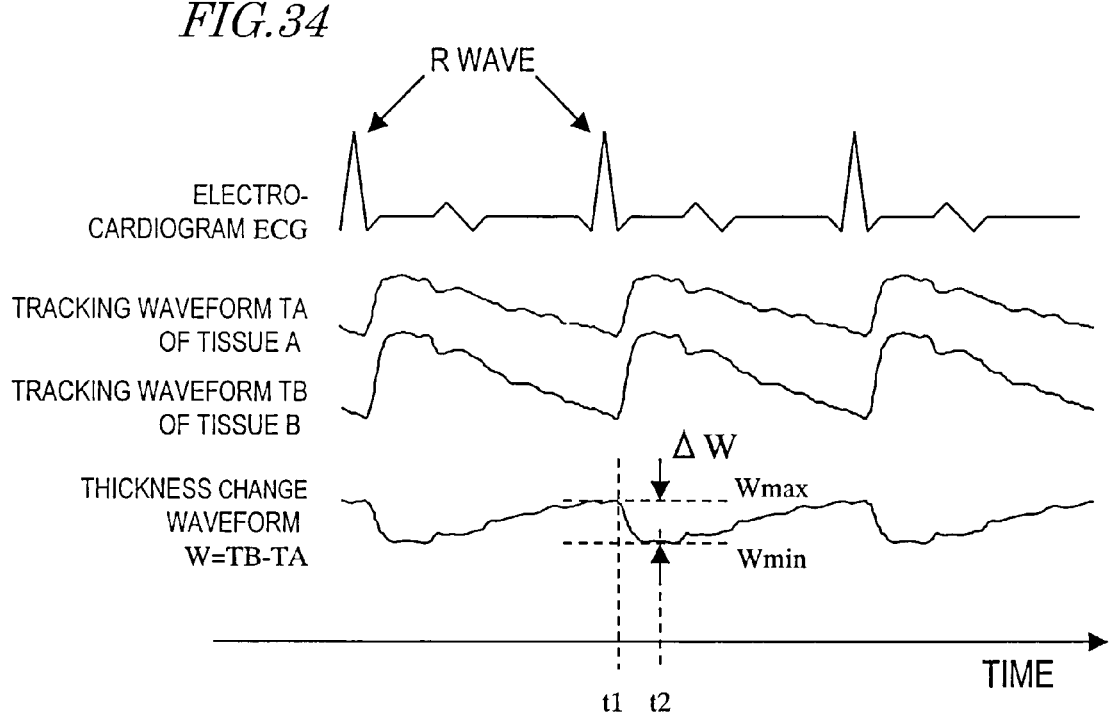

FIG. 34 shows how to calculate the magnitude of strain based on the tracking waveform of a subject tissue.

Figure 35:
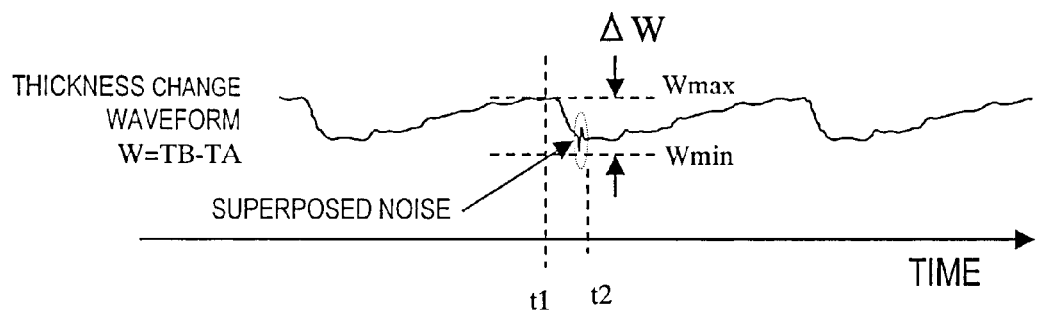

FIG. 35 shows an error that the greatest thickness change may have in a situation where noise is superposed on a thickness change waveform.

DESCRIPTION OF REFERENCE NUMERALS 11 atheroma
12 subject
31 vessel anterior wall
32 vascular lumen
33 vessel posterior wall
100 control section
101 probe 102 transmitting section
103 receiving section
104 tomographic image generating section
105 image synthesizing section
106 image display section
115 displacement waveform calculating section
116 thickness change waveform calculating section
117A through 117H reference waveform generating section
118, 118', 118" thickness change estimating section
119 blood pressure manometer
120 modulus of elasticity calculating section
121 viscosity coefficient determining section
125 comparing section
140 period adjusting section
141 period detecting section
142 vascular diameter calculating section
151 computing section
170 averaging section
171, 171' reliability determining section
172 tissue identifying section
201 through 210, 210', 210" ultrasonic diagnostic apparatus

BEST MODE FOR CARRYING OUT THE INVENTION

Embodiment 1

Figure 1:
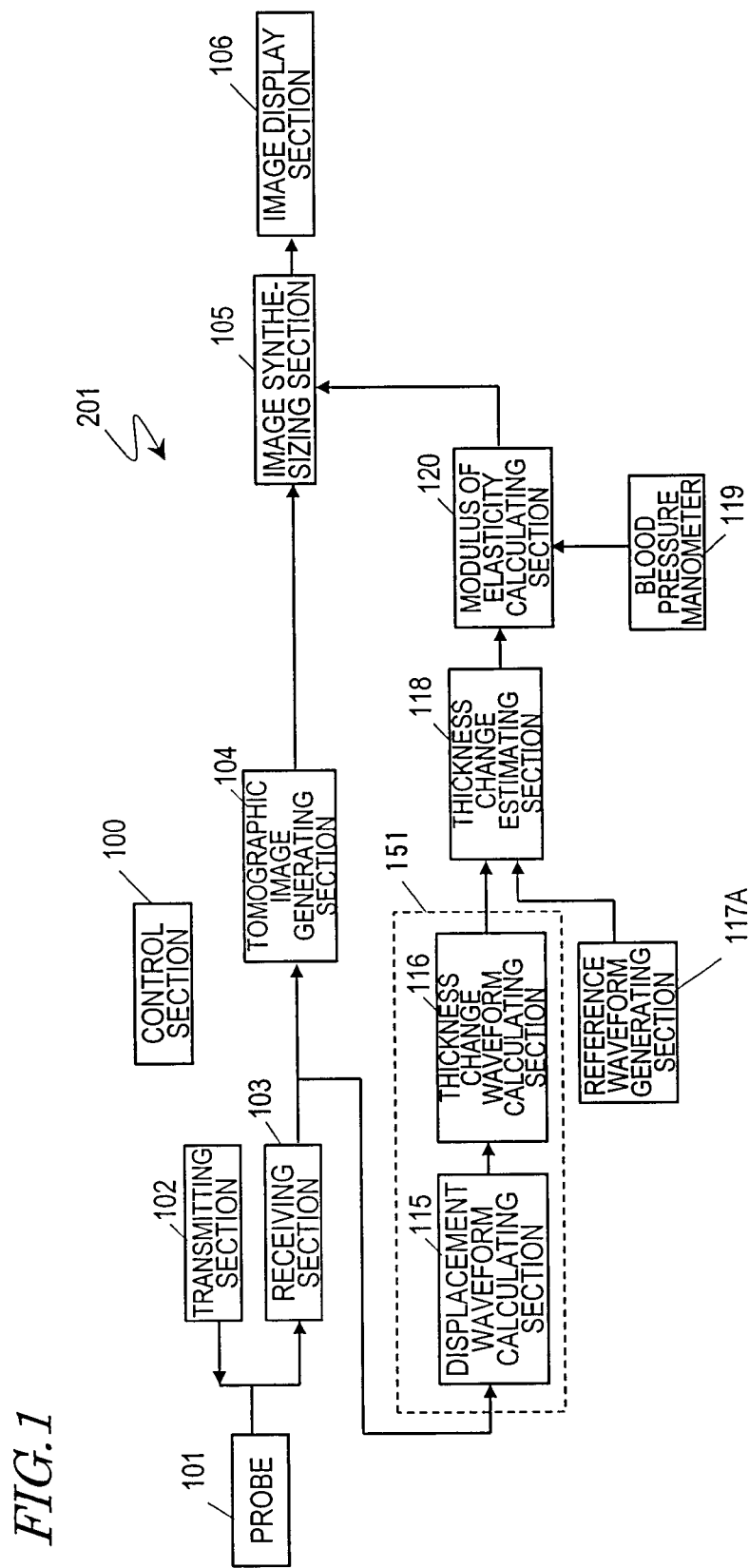
FIG. 1 is a block diagram showing a first preferred embodiment of an ultrasonic diagnostic apparatus according to the present invention.

Hereinafter, a First Preferred Embodiment of an ultrasonic diagnostic apparatus according to the present invention will be described. FIG. 1 is a block diagram showing the configuration of an ultrasonic diagnostic apparatus 201, which includes a transmitting section 102, a receiving section 103, a computing section 151, a reference waveform generating section 117A and a thickness change estimating section 118. The ultrasonic diagnostic apparatus 201 also includes a control section 100 for controlling all of these components of its own.

In accordance with the instruction given by the control section 100, the transmitting section 102 generates a drive signal to drive a probe 101 at a predetermined timing. In response to the drive signal, the probe 101 transmits an ultrasonic wave. The ultrasonic wave thus transmitted soon reaches a subject being deformed periodically under stress and is reflected inside the subject. In this preferred embodiment, the subject includes the vessel wall of an arterial canal and the modulus of elasticity of the vessel wall is calculated as information about the subject's internal tissue. Blood flows through the arterial canal in a period that is synchronized with a cardiac cycle. That is why the vessel wall is deformed periodically under the stress caused by the blood flow.

The receiving section 103 receives an echo, reflected from the subject, at the probe 101, converts the echo into an electrical signal, and then amplifies the electrical signal, thereby generating a received echo signal. The receiving section 103 also converts the received echo signal into a digital signal.

The transmitting section 102 and the receiving section 103 preferably include a time delay control section for controlling the time delay caused in the drive signal or the received echo signal in order to scan the subject with the ultrasonic wave transmitted and detect only the ultrasonic wave that has been reflected from a predetermined location or in a predetermined direction. Also, the probe 101 preferably includes an array of ultrasonic oscillators.

The computing section 151 analyzes the received echo signal to track the motions of the subject on multiple measuring points, and also generates a thickness change waveform representing a variation in distance between two arbitrary measuring points on the subject. For that purpose, the computing section 151 includes a displacement waveform calculating section 115 and a thickness change waveform calculating section 116. The displacement waveform calculating section 115 receives the received echo signal and figures out a displacement waveform, representing the displacements of multiple measuring points xi on the subject, by Equations (1) and (2). The thickness change waveform calculating section 116 figures out a thickness change waveform, representing a variation in distance between two points that have been selected arbitrarily from those measuring points xi, by calculating the difference between the displacement waveforms of the two measuring points.

Multiple measuring points can be set on a single ultrasonic beam according to the resolution that is defined by the frequency of the ultrasonic wave to be transmitted, for example. That is why by scanning the subject with an ultrasonic beam, the displacement waveforms of respective measuring points, which are arranged two-dimensionally, can be obtained.

The reference waveform generating section 117A outputs a reference waveform. As will be described in detail later, this reference waveform is used as a reference for the thickness change waveform to be figured out by the thickness change waveform calculating section 116. In this preferred embodiment, the reference waveform has been figured out in advance by measuring, for example, and the data about the reference waveform is stored in a storage section such as a semiconductor memory for the reference waveform generating section 117A. In this manner, the reference waveform generating section 117 may store the data of the reference waveform itself and output the data in accordance with the instruction given by the control section 100. Alternatively, as will be described later for other preferred embodiments, the reference waveform generating section 117A may generate a reference waveform based on externally provided data and output the waveform. That is to say, the reference waveform generating section herein just needs to output a reference waveform.

As will also be described in detail later, the thickness change estimating section 118 compares the thickness change waveform supplied from the thickness change waveform calculating section 116 to the reference waveform supplied from the reference waveform generating section 117A, thereby getting information about the subject's internal tissue. More specifically, the thickness change estimating section 118 calculates the greatest variation in the thickness change waveform. This calculation is done every period of the thickness change waveform. In this point, the present invention is quite different from the prior art in which the greatest difference is calculated based on the maximum and minimum values of the thickness change waveform.

The ultrasonic diagnostic apparatus 201 preferably further includes a modulus of elasticity calculating section 120 for calculating a modulus of elasticity based on the greatest variation obtained. The modulus of elasticity calculating section 120 receives information about the stress applied to the subject (e.g., the blood pressure difference $\Delta P$ between the highest and lowest blood pressures) from the blood pressure manometer 119, for example. And the modulus of elasticity calculating section 120 calculates the modulus of elasticity $Er$ based on the blood pressure difference $\Delta P$ and the greatest thickness change $\Delta W$ by Equation (6). In this case, the reference thickness Ws is the distance (e.g., 400 μm) between the two measuring points at which the thickness change waveform was figured out, and is determined in advance by the two measuring points that have been set by the thickness change waveform calculating section 116. In this manner, the modulus of elasticity of the subject can be obtained.

The modulus of elasticity thus obtained is preferably displayed along with the tomographic image of the subject because the location of the measuring point can be shown clearly. For that purpose, the ultrasonic diagnostic apparatus 201 preferably further includes a tomographic image generating section 104, an image synthesizing section 105 and an image display section 106. The tomographic image generating section 104 includes a filter and an amplitude detector and analyzes mainly the amplitude of the received echo signal supplied from the receiving section 103, thereby generating an image signal as a tomographic image representing the subject's internal structure.

The image synthesizing section 105 receives the image signal and the data about the modulus of elasticity that has been supplied from the modulus of elasticity calculating section 120, and synthesizes the image signal and modulus of elasticity data together such that the modulus of elasticity obtained is mapped to an appropriate location on the tomographic image. Then, the image display section 106 presents the synthesized image thereon.

Figure 2:
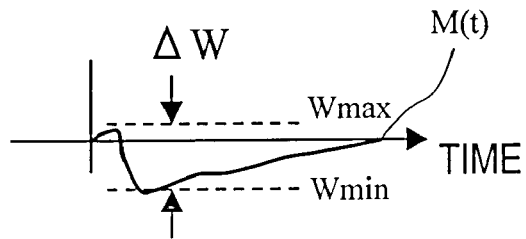
FIG. 2 shows a reference waveform generated by the reference waveform generating section of the ultrasonic diagnostic apparatus shown in FIG. 1.

Hereinafter, it will be described in further detail how the reference waveform generating section 117A and the thickness change estimating section 118, which are the core sections of the present invention, operate. FIG. 2 shows the reference waveform M(t) that is stored in the storage section of the reference waveform generating section 117A. This waveform is obtained by figuring out the thickness change waveforms of a plurality of subjects in advance and calculating the average of those waveforms for one cardiac cycle. The reference waveform M(t) is prepared in advance for an object of measurement by the ultrasonic diagnostic apparatus 201. In this preferred embodiment, to calculate the modulus of elasticity of the vessel wall of the arterial canal, the reference waveform, calculated on the vessel walls of the arterial canals of a plurality of subjects, is used as the reference waveform M(t).

ΔW, which is the amplitude of the reference waveform M(t), has been normalized to be a reference value of 1 μm, for example. Since the data collected from a plurality of subjects is averaged, the influence of noise on even the actually collected data has been reduced.

Figure 3:
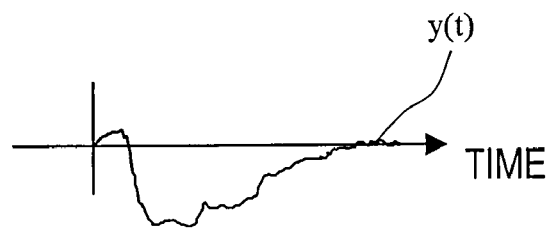
FIG. 3 shows a thickness change waveform output by the thickness change waveform calculating section of the ultrasonic diagnostic apparatus shown in FIG. 1.

FIG. 3 shows the thickness change waveform y(t) obtained by the thickness change waveform calculating section 116. This thickness change waveform is a portion of the waveform obtained by actually inspecting the subject for one cardiac cycle. In this case, t represents the sampling time and is an integer, i.e., t=0, 1, . . . and N−1, where N is the number of sample points.

The thickness change estimating section 118 receives the reference waveform M(t) and the thickness change waveform y(t) and calculates, by the minimum square method, how many times the amplitude of the thickness change waveform y(t) should be multiplied to make the product closest to the reference waveform M(t). If the coefficient to be multiplied by y(t) is k and the square of the difference between M(t) and k·y(t) is R, then R is given by the following Equation (7).

$$R = \sum_{t=0}^{N-1} (M(t) - k \cdot y(t))^2 \tag{7}$$

If Equation (7) is subjected to partial differentiation using the coefficient k as a variable and if the resultant equation becomes equal to zero, then the squared difference R will be minimum:

$$\frac{\partial R}{\partial k} = 2\sum_{t=0}^{N-1} (-M(t)y(t) + k(y(t))^2) = 0 \tag{8}$$

By resolving Equation (8) with respect to k, the following Equation (9) is obtained.

$$k = \frac{\sum_{t=0}^{N-1} M(t)y(t)}{\sum_{t=0}^{N-1} (y(t))^2} \tag{9}$$

The value of the coefficient k obtained by Equation (9) means that if the thickness change waveform y(t) is multiplied by k, then the square of the difference from the reference waveform M(t) with an amplitude of 1 μm will be minimum and the two waveforms will match most closely to each other. That is why the amplitude A of the thickness change waveform y(t) measured can be calculated by the following Equation (10).

$$A = 1/k \text{ (μm)} \tag{10}$$

Alternatively, it may also be calculated by the same method as that described above how many times the amplitude of the reference waveform M(t) should be multiplied to make the product closest to the actual thickness change waveform y(t). In that case, if the coefficient to be multiplied by the reference waveform M(t) is a and if the residual is R', then the residual R' can be calculated by the following Equation (11).

$$R' = \sum_{t=0}^{N-1} (a \cdot M(t) - y(t))^2 \tag{11}$$

If R' is supposed to be zero when subjected to partial differentiation with the coefficient a as in the following Equation (12) and if R' is resolved with respect to a, then the following Equation (13) is obtained.

$$\frac{\partial R'}{\partial a} = 2\sum_{t=0}^{N-1} (a(M(t))^2 - M(t)y(t)) = 0 \tag{12}$$

$$a = \frac{\sum_{t=0}^{N-1} M(t)y(t)}{\sum_{t=0}^{N-1} (M(t))^2} \tag{13}$$

In that case, the coefficient a means that if the reference waveform with an amplitude of 1 μm is multiplied by a, then the square of the difference from the actual thickness change waveform y(t) will be minimum and the two waveforms will match most closely to each other. That is why the amplitude A' of the thickness change waveform y(t) can be calculated by the following Equation (14).

$$A' = a \text{ (μm)} \tag{14}$$

As described above, the thickness change estimating section 118 receives the reference waveform M(t) and the thickness change waveform y(t) and calculates either the coefficient k or the coefficient a that would minimize the matching error between the reference waveform M(t) and the thickness change waveform y(t) by either Equation (9) or Equation (13). Then, based on the coefficient k or a thus calculated, the thickness change estimating section 118 further calculates the greatest thickness change as the amplitude of the thickness change waveform.

Figure 4:
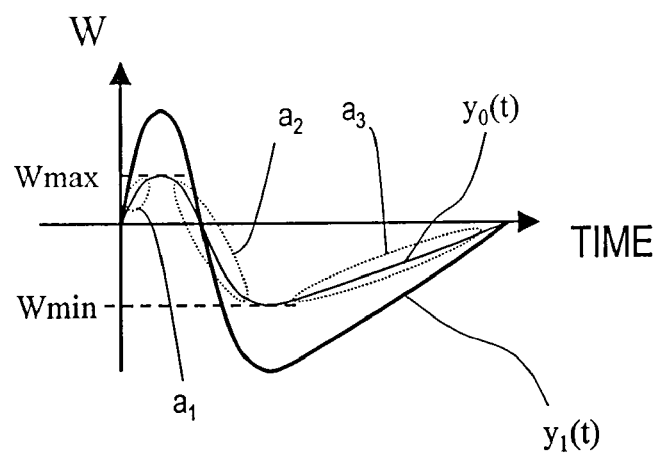
FIG. 4 shows information contained in the thickness change waveform.

FIG. 4 schematically shows portions of thickness change waveforms $y_0(t)$ and $y_1(t)$ that were figured out on blood vessel walls with mutually different moduli of elasticity for one cardiac cycle. As shown in FIG. 4, as the moduli of elasticity are different, their amplitudes are also different from each other. However, these two thickness change waveforms have the same variation pattern along the time axis. This means that the variation in blood pressure or the vibration of the heart, which is a variation in the stress applied to the subject, is ideally substantially constant irrespective of the hardness of the blood vessel.

As shown in FIG. 4, to calculate the greatest thickness difference of the thickness change waveform by a conventional method, the maximum and minimum values Wmax and Wmin of the thickness change waveform need to be found. On the other hand, according to the present invention, the greatest thickness change is estimated by analyzing the degree of matching between the thickness change waveform and the reference waveform. This means that the greatest thickness change is estimated based on the entire thickness change waveform for one cardiac cycle on the supposition that only the amplitude of the thickness change waveform changes due to a difference in modulus of elasticity as described above.

As shown for the thickness change waveform $y_0(t)$ in FIG. 4, each of the maximum and minimum values Wmax and Wmin of the thickness change waveform is defined by a certain point on the thickness change waveform $y_0(t)$. However, the gradients of curved portions a1, a2 and a3 of the thickness change waveform between the maximum and minimum values Wmax and Wmin thereof change with the maximum and minimum values Wmax and Wmin. In other words, the gradients of the curved portions a1, a2 and a3 include information about the maximum and minimum values Wmax and Wmin. That is why even if an accurate maximum or minimum value Wmax or Wmin could not be obtained due to the superposition of noise on the thickness change waveform, the greatest thickness change could still be estimated based on the entire thickness change waveform, including the curved portions a1, a2 and a3, unless the superposed noise deforms the thickness change waveform significantly.

Consequently, according to the present invention, the greatest thickness change or the modulus of elasticity can be calculated highly accurately without being affected by suddenly produced noise such as spike noise.

As is clear from the foregoing description, since the curved portions a1, a2 and a3 contain information about the maximum and minimum values Wmax and Wmin, the greatest thickness change can be estimated without being affected by noise so much as in the conventional method even by using only a portion of one cardiac cycle of the thickness change waveform. Nevertheless, the longer the selected interval, the more accurate the greatest thickness change estimated will be. That is why it is most preferable to calculate the greatest thickness change by comparing one full cardiac cycle of the thickness change waveform to the reference waveform. This can be stated in the following way using Equation (13). Specifically, if the thickness change waveform y(t) is represented as the sum of a thickness change s(t) and noise n(t), Equation (13) may be modified as follows:

$$a = \frac{\sum_{t=0}^{N-1} M(t)s(t) + \sum_{t=0}^{N-1} M(t)n(t)}{\sum_{t=0}^{N-1} (M(t))^2} \quad (13')$$

If the noise n(t) is spike noise or random noise, the longer the addition period, the smaller the second term of the numerator of Equation (13') with respect to the first term thereof. That is why if the thickness change s(t) is similar to the reference waveform (i.e., s(t)=a'·M(t)) and if the addition period is sufficiently long and if the second term of Equation (13') is negligible, then Equation (13') can be modified into the following Equation (13").

$$a = \frac{\sum_{t=0}^{N-1} M(t)s(t)}{\sum_{t=0}^{N-1} (M(t))^2} = \frac{\sum_{t=0}^{N-1} a' \cdot (M(t))^2}{\sum_{t=0}^{N-1} (M(t))^2} = a' \quad (13'')$$

Consequently, the true coefficient a' can be estimated. Stated otherwise, it can be seen that by comparing the entire thickness change waveform to the reference waveform, the thickness change can be estimated with the influence of noise reduced.

According to the present invention, the greatest thickness change and the modulus of elasticity are calculated based on the reference waveform and actually measured values. That is why it is important to define an appropriate reference waveform. If the thickness change waveform changes differently with time according to the specific measuring site on the subject, then the reference waveform is preferably defined on a site-by-site basis. Specifically, if the modulus of elasticity of the vessel wall of the arterial canal should be calculated, reference waveform data may be provided for the intima, media, and adventitia of the vessel wall. By storing sets of reference waveform data in the reference waveform generating section 117A and changing those sets of reference waveform data on a site-by-site basis, the thickness change can be estimated even more precisely.

Optionally, a number of different sets of reference waveform data may also be stored in the storage section of the reference waveform generating section 117A according to the physical condition of the subject, e.g., a reference waveform for healthy persons, a reference waveform for diabetics, and a reference waveform for patients with arterial sclerosis. And one of those reference waveforms may be selected in accordance with the operator's instruction. Then, the thickness change can be estimated even more accurately.

Embodiment 2

Figure 5:
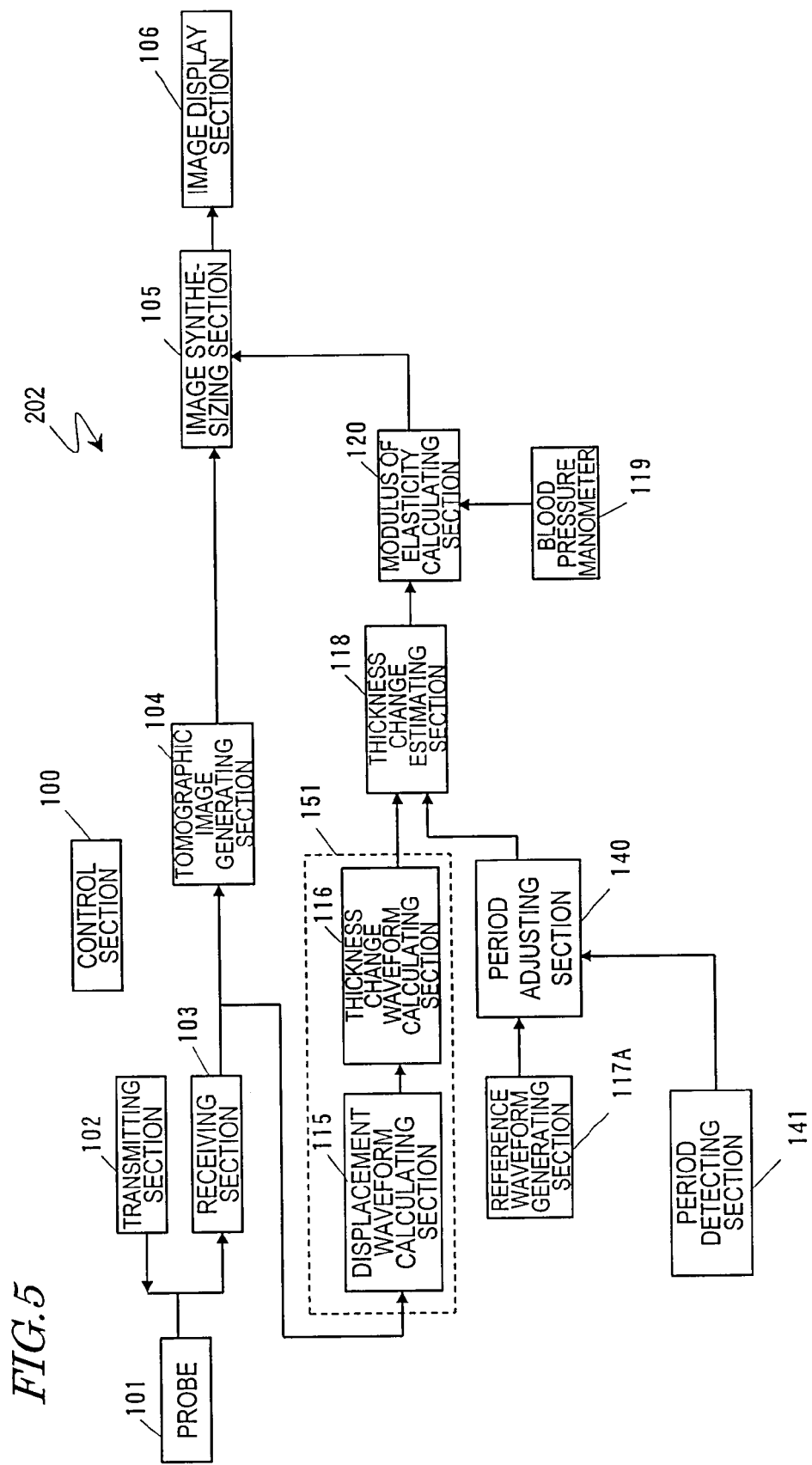
FIG. 5 is a block diagram showing a second preferred embodiment of an ultrasonic diagnostic apparatus according to the present invention.

Hereinafter, a second preferred embodiment of an ultrasonic diagnostic apparatus according to the present invention will be described. FIG. 5 is a block diagram showing the configuration of the ultrasonic diagnostic apparatus 202, which further includes a period adjusting section 140 that is not included in the ultrasonic diagnostic apparatus 201 of the first preferred embodiment described above. The transmitting section 102, receiving section 103, computing section 151 and thickness change estimating section 118 of the ultrasonic diagnostic apparatus 202 have the same functions as the counterparts of the ultrasonic diagnostic apparatus 201 of the first preferred embodiment.

The period adjusting section 140 adjusts the period of the reference waveform such that the period of the reference waveform generated by the reference waveform generating section 117A matches that of the thickness change waveform figured out by the thickness change waveform calculating section 116. For that purpose, the ultrasonic diagnostic apparatus 202 receives information about the period of subject's stress variation from an external period detecting section 141. If the subject is the vessel wall of the arterial canal, then a variation in the blood pressure, electrocardiogram or electrocardiophonogram of the subject may be used. For example, an electrocardiograph for detecting the cardiac cycle of the heart may be used effectively as the period detecting section 141.

Portions (a), (b) and (c) of FIG. 6 show the electrocardiogram provided by the period detecting section 141, the thickness change waveform y(t) figured out by the thickness change waveform calculating section 116, and the reference waveform M(t) figured out by the reference waveform generating section 117A. As shown in portion (a) of FIG. 6, an R wave is observed in the electrocardiogram. Meanwhile, as is clear from portions (a) and (b) of FIG. 6, the period of the electrocardiogram agrees with the period Ty of the thickness change waveform y(t). This is because the variation in the thickness of the vessel wall of the arterial canal is caused by the variation in the blood pressure due to the heartbeat.

On the other hand, as is clear from portions (b) and (c) of FIG. 6, the period Tm of the reference waveform M(t) does not agree with the period Ty of the thickness change waveform y(t).

To resolve the disagreement in period between the reference waveform M(t) and the thickness change waveform y(t), the period adjusting section 140 adjusts the period of the reference waveform M(t) based on the information about the period of the subject's stress variation provided by the period detecting section 141. In this preferred embodiment, the period adjusting section 140 detects the period of the R wave of the electrocardiogram, thereby extending or shrinking the reference waveform M(t) generated by the reference waveform generating section 117A along the time axis. The reference waveform M'(t) that has been extended or shrunk along the time axis may be given by the following Equation (15).

$$M'(t)=M(t\cdot Ty/Tm) \quad (15)$$

In this case, unless t·Ty/Tm becomes an integer, an interpolated value is generated based on the relation between t and M(t). Optionally, the M(t) values may be stored on a sufficiently fine sampling unit and a value in the closest proximity could be used as an alternative value.

If the thickness change estimating section 118 has sensed, as a result of calculations on correlation between M'(t) and y(t), that M'(t) and y(t) are out of phase with each other on the time axis, adjustments can be made by appropriately shifting the timing of reading the reference waveform from the reference waveform generating section 117A, for example.

After the period of the reference waveform M'(t) has been matched to that of the thickness change waveform y(t) in this manner, the thickness change estimating section 118 may calculate the greatest thickness change in the thickness change waveform y(t) as already described for the first preferred embodiment.

As described above, according to this preferred embodiment, the period adjusting section 140 adjusts the period of the reference waveform, generated by the reference waveform generating section 117A, to that of the subject's stress variation, thereby calculating the thickness change and modulus of elasticity more accurately.

In the preferred embodiment described above, the period of the reference waveform is supposed to be adjusted. Alternatively, the period of the thickness change waveform, figured out by the thickness change waveform calculating section 116, may be adjusted so as to agree with the period of the reference waveform. In the modified ultrasonic diagnostic apparatus 202' shown in FIG. 7, the period adjusting section 140 receives the thickness change waveform that has been figured out by the thickness change waveform calculating section 116, and then is provided with information about the stress applied to the subject by the period detecting section 141 to adjust the period of the thickness change waveform. Even if such a configuration is adopted, the same effects as those described above are also achieved.

If the cardiac cycle of the subject changes from one pulse after another due to arrhythmia, for example, to make the period of the thickness change waveform inconstant, the period adjusting section 140 may extract data about respective periods in the shortest one of those inconstant periods of the thickness change waveform to make the periods of the thickness change waveform constant. More specifically, supposing the shortest cardiac cycle is $T_{min}$, the period adjusting section 140 may extract data during that period $T_{min}$ from the respective cardiac cycles of the thickness change waveform using the R wave on the electrocardiogram as a trigger, thereby making the periods of the thickness change waveform constant.

In this case, since the R wave is observed at the beginning of the systolic phase, the diastolic phase of some cardiac cycle may have partially missing data as a result of such data extraction. However, if the same subject has different cardiac cycles between his or her pulses, the length of the systolic phases of the cardiac cycles tends to change hardly but that of the diastolic phases tends to change in most cases. Also, the maximum and minimum values of the thickness change that are needed to evaluate the elastic property are observed during the systolic phase. That is why even if some data were missing during the diastolic phase, the modulus of elasticity measured would not be affected so seriously. After the periods of the thickness change waveform have been made constant, the periods of the reference waveform and the thickness change waveform may be matched to each other if necessary as described above.

Embodiment 3

Hereinafter, a third preferred embodiment of an ultrasonic diagnostic apparatus according to the present invention will be described. FIG. 8 is a block diagram showing the configuration of the ultrasonic diagnostic apparatus 203, which further includes an averaging section 170 that is not included in the ultrasonic diagnostic apparatus 202' of the second preferred embodiment described above. The transmitting section 102, receiving section 103, computing section 151, thickness change estimating section 118 and period adjusting section 140 of the ultrasonic diagnostic apparatus 203 have the same functions as the counterparts of the ultrasonic diagnostic apparatus 202' of the second preferred embodiment.

The averaging section 170 calculates the average of the thickness change waveform, of which the period has been adjusted, over multiple periods. Portion (a) of FIG. 9 shows a waveform representing the information about subject's deformation period that has been provided by the period detecting section 141. As in the second preferred embodiment described above, information about the subject's deformation period may be an electrocardiogram, for example. Portion (b) of FIG. 9 shows two periods y'1(t) and y'2(t) of the thickness change waveform y'(t), of which the period has been adjusted by the period adjusting section 140.

The averaging section 170 calculates the average of the thickness change waveform y'(t) over multiple periods. The averaged thickness change waveform Y(t) may be calculated by the following Equation (16).

$$Y(t) = \frac{1}{L}\sum_{i=0}^{L-1} y'_i(t) \quad (16)$$

Here, $y'_i(t)$ represents the thickness change waveform of the $i^{th}$ cardiac cycle and L represents the number of cardiac cycles to be averaged. The averaged thickness change waveform Y(t) that has been calculated by the averaging section 170 is input to the thickness change estimating section 118, which calculates the greatest thickness change as already described for the first preferred embodiment. Since the thickness change waveform that has had its period adjusted is input to the averaging section 170, the respective periods of the thickness change waveform are constant and the averaging section 170 performs the computation of Equation (16) as a simple addition.

The number of cardiac cycles to be averaged may be arbitrarily selected. The average may be calculated over the entire measuring period. Alternatively, the average may also be calculated over a number of periods with the cardiac cycle to calculate the average in shifted in real time. According to Equation (16), the average is supposed to be calculated by simply adding the thickness change waveforms together. Optionally, the average of weighted sum may also be calculated.

According to this preferred embodiment, the random noise contained in the thickness change waveform can be reduced as a result of the averaging done by the averaging section 170. That is why the thickness change estimating section 118 can estimate the greatest thickness change more accurately and the modulus of elasticity can be calculated even more accurately.

Embodiment 4

Hereinafter, a fourth preferred embodiment of an ultrasonic diagnostic apparatus according to the present invention will be described. FIG. 10 is a block diagram showing the configuration of an ultrasonic diagnostic apparatus 204. The ultrasonic diagnostic apparatus of the preferred embodiments described above is supposed to estimate the greatest thickness change based on the entire thickness change waveform using a reference waveform that has been generated in advance by measuring, for example. On the other hand, the ultrasonic diagnostic apparatus 204 generates a reference waveform based on the displacement waveform of a measuring point to be obtained by subjecting the subject to measurements. For that purpose, the ultrasonic diagnostic apparatus 204 includes a reference waveform generating section 117B for generating a reference waveform based on a displacement waveform supplied from a displacement waveform calculating section 115.

FIG. 11 schematically illustrates a cross section of the subject 12 of measurements by the probe 101. The subject 12 includes an arterial canal and ultrasonic beams 20a, 20b and 20c are transmitted from the probe 101 so as to measure cross sections perpendicularly to the axis of the arterial canal. On the scanning cross sections, the arterial canal includes a vessel anterior wall 31, a vascular lumen 32 and a vessel posterior wall 33.

As the pressure of blood flowing through the vascular lumen 32 varies, the vessel anterior and posterior walls 31 and 33 receive stress from the blood to repeatedly dilate and shrink periodically. In a vascular region 21a in the vessel anterior wall 31 that has a very small width on the ultrasonic beam 20c, the thickness change, which is a variation in distance between two points p1 and p2, should be caused due to the displacement of the intima-side end 22a. That is why the tissue displacement waveform of the intima-side end 22a should be similar to the thickness change waveform between p1 and p2.

FIG. 12(a) shows the displacement waveform n(t) of the intima-side end 22a, for example, which has been figured out by the displacement waveform calculating section 115. On the other hand, FIG. 12(b) shows a reference waveform M(t) generated by the reference waveform generating section 117B based on the displacement waveform n(t). In FIG. 12, t represents the sampling time and is an integer, i.e., t=0, 1, ... and N−1, where N is the number of sample points. In the displacement waveform n(t), if the measuring point moves in the direction in which the vascular caliber increases, then the direction is called a "positive direction". The waveforms shown in FIG. 12 are only portions corresponding to one cardiac cycle. Supposing the maximum and minimum values of the displacement waveform n(t) during one cardiac cycle are identified by Nmax and Nmin, respectively, the reference waveform generating section 117 figures out the reference waveform M(t) based on the displacement waveform n(t) by the following Equation (17).

$$M(t) = \frac{-1}{N_{max} - N_{min}} \cdot n(t) \quad (17)$$

As a result, the reference waveform M(t) becomes a waveform that is proportional to the waveform n(t) of the intima-side end 22a and that has an amplitude of one.

FIG. 13 shows a portion of a thickness change waveform y(t) that was actually measured for one cardiac cycle and output from the thickness change waveform calculating section 116. This thickness change waveform y(t) may be obtained as a difference between the displacement waveforms at the measuring points p1 and p2 shown in FIG. 11, for example.

As shown in FIG. 11, both the reference waveform M(t) and the thickness change waveform y(t) are based on the received echo signal resulting from the ultrasonic beam 20c. However, the thickness change waveform y(t) represents a variation in a very short distance between two points but the reference waveform M(t) is based on the displacement waveform n(t). As shown in FIG. 12(a), the displacement waveform n(t) may have an amplitude D1 on the order of several hundreds of μm, for example. On the other hand, the thickness change waveform y(t) has an amplitude D2 on the order of several tens of μm. That is why the reference waveform M(t) should be affected by noise to much lesser degree than the thickness change waveform y(t).

Therefore, if the thickness change estimating section 118 calculates the greatest thickness change based on the entire thickness change waveform as already described for the first preferred embodiment by using a reference waveform thus generated, the greatest thickness change or the modulus of elasticity can be calculated highly accurately without being affected by suddenly produced noise such as spike noise. Particularly, according to this preferred embodiment, both the reference waveform M(t) and the thickness change waveform y(t) are based on the same received echo signal. That is why even without the period adjusting section, the two waveforms should have matching periods, and therefore, the greatest thickness change can be calculated highly accurately. In addition, since no external signal representing the subject's stress variation period needs to be provided by an electrocardiograph or a blood pressure manometer, for example, the measurements can be done easily.

Embodiment 5

Hereinafter, a fifth preferred embodiment of an ultrasonic diagnostic apparatus according to the present invention will be described. FIG. 14 is a block diagram showing the configuration of the ultrasonic diagnostic apparatus 205, which further includes a vascular diameter calculating section 142 that is not included in the ultrasonic diagnostic apparatus 204 of the fourth preferred embodiment described above.

The vascular diameter calculating section 142 receives a displacement waveform from the displacement waveform calculating section and figures out a waveform representing the inside or outside vascular caliber of the arterial canal of the subject. The reference waveform generating section 117 receives the vascular caliber waveform from the vascular diameter calculating section 142 and generates a reference waveform based on the vascular caliber waveform. More specifically, to define the vascular lumen 32, the intima-side ends 22a and 22b of the blood vessel wall are located as shown in FIG. 11. These points may be either specified on a tomographic image of the arterial canal presented on the image display section 106 by the operator who is watching the image or located automatically by the control section 100 based on the analysis of the received echo signal. Supposing the displacement waveforms of the intima-side ends 22a and 22b are identified by ia(t) and ib(t), respectively, the vascular caliber waveform L(t) is given by the following Equation (18).

$$L(t)=ia(t)+ib(t) \quad (18)$$

Here, the signs of ia(t) and ib(t) are supposed to be positive in the direction in which the vascular caliber increases. Optionally, a waveform representing a variation in the outside vascular caliber may also be figured out as described above.

The reference waveform generating section 117 receives the vascular caliber waveform L(t) and uses the vascular caliber waveform L(t) in place of the displacement waveform n(t) in Equation (17), thereby generating a reference waveform M(t). In this manner, either the greatest thickness change or the modulus of elasticity can be calculated as in the fourth preferred embodiment described above.

In this preferred embodiment, the vascular caliber waveform for use to generate the reference waveform shows a variation in vascular caliber and has close correlation with the pressure of blood flowing through the blood vessel. Also, either the deformation or thickness change of the blood vessel wall has correlation with the blood pressure. That is why the thickness change, representing a variation in distance between two points on the blood vessel wall, has correlation with a variation in vascular caliber, and therefore, the vascular caliber waveform can be used effectively to generate the reference waveform.

Specifically, the intima-side ends 22a and 22b that define the vascular caliber move in opposite directions under the blood pressure, and therefore, the amplitude of the vascular caliber waveform L(t) becomes approximately twice as large as that of the displacement waveform ia(t) or ib(t). That is why the influence of noise on the vascular caliber waveform L(t) has been reduced and the reference waveform generated is also hardly affected by noise. Consequently, the thickness change and modulus of elasticity can be calculated even more accurately.

Embodiment 6

Hereinafter, a sixth preferred embodiment of an ultrasonic diagnostic apparatus according to the present invention will be described. FIG. 15 is a block diagram showing the configuration of an ultrasonic diagnostic apparatus 206. In the fourth preferred embodiment described above, the reference waveform generating section 117B generates a reference waveform based on the displacement waveform. According to this preferred embodiment, the reference waveform generating section 117C receives a blood pressure waveform from an external device and generates a reference waveform based on the blood pressure waveform.

The blood pressure waveform supplied to the reference waveform generating section 117C represents a variation in the blood pressure of the arterial canal of the subject and is provided by the real-time blood pressure manometer 150, for example.

FIG. 16 shows an exemplary blood pressure waveform. The variation in blood pressure substantially agrees with the displacement waveform n(t) shown in FIG. 12(a). The reference waveform generating section 117C receives the blood pressure waveform and generates a reference waveform M(t) by Equation (17). The thickness change, representing a variation in distance between two points on the blood vessel wall, is produced by a variation in blood pressure. That is to say, since the thickness change has correlation with the blood pressure variation, the blood pressure waveform can be used effectively to generate a reference waveform. As a result, by using the reference waveform thus generated, the thickness change and modulus of elasticity can be calculated even more accurately.

Embodiment 7

Hereinafter, a seventh preferred embodiment of an ultrasonic diagnostic apparatus according to the present invention will be described. FIG. 17 is a block diagram showing the configuration of an ultrasonic diagnostic apparatus 207, which includes a transmitting section 102, a receiving section 103, a computing section 151, a reference waveform generating section 117D, a thickness change estimating section 118' and a reliability determining section 171. The ultrasonic diagnostic apparatus 207 also includes a control section 100 for controlling all of these components of its own.

The transmitting section 102 and the receiving section 103 function in the same way as the counterparts 102 and 103 of the first preferred embodiment described above. Specifically, in accordance with the instruction given by the control section 100, the transmitting section 102 generates a drive signal to drive a probe 101 at a predetermined timing. In response to the drive signal, the probe 101 transmits an ultrasonic wave. The ultrasonic wave thus transmitted soon reaches a subject being deformed periodically under stress and is reflected inside the subject. In this preferred embodiment, the subject includes the vessel wall of an arterial canal and the ultrasonic diagnostic apparatus 207 calculates the modulus of elasticity of the vessel wall. Blood flows through the arterial canal in a period that is synchronized with a cardiac cycle. That is why the vessel wall is deformed periodically under the stress caused by the blood flow.

The receiving section 103 receives an echo, reflected from the subject, at the probe 101. Specifically, the probe 101 converts the echo into an electrical signal, and then the receiving section 103 amplifies the electrical signal, thereby generating a received echo signal. Then the receiving section 103 converts the received echo signal into a digital signal.

The transmitting section 102 and the receiving section 103 preferably include a time delay control section for controlling the time delay caused in the drive signal or the received echo signal in order to scan the subject with the ultrasonic wave transmitted and detect only the ultrasonic wave that has been reflected from a predetermined location or in a predetermined direction. Also, the probe 101 preferably includes an array of ultrasonic oscillators.

The computing section 151 also operates in the same way as the counterpart 151 of the first preferred embodiment described above. Specifically, the computing section 151 analyzes the received echo signal to track the motions of the subject on multiple measuring points, and also generates a thickness change waveform representing a variation in distance between two arbitrary measuring points on the subject. For that purpose, the computing section 151 includes a displacement waveform calculating section 115 and a thickness change waveform calculating section 116. The displacement waveform calculating section 115 receives the received echo signal and figures out a displacement waveform, representing the displacements of multiple measuring points on the subject, by Equations (1) and (2). The thickness change waveform calculating section 116 figures out a thickness change waveform, representing a variation in distance between two points that have been selected arbitrarily from those measuring points, by calculating the difference between the displacement waveforms of the two measuring points.

Multiple measuring points can be set on a single ultrasonic beam according to the resolution that is defined by the frequency of the ultrasonic wave to be transmitted, for example. That is why by scanning the subject with an ultrasonic beam, the displacement waveforms of respective measuring points, which are arranged two-dimensionally, can be obtained.

The reference waveform generating section 117D generates a reference waveform. This reference waveform is used as a reference for the thickness change waveform to be figured out by the thickness change waveform calculating section 116. In this preferred embodiment, the reference waveform has been figured out in advance by measuring, for example, and the data about the reference waveform is stored in a storage section such as a semiconductor memory for the reference waveform generating section 117D.

As already described for the first preferred embodiment, the thickness change estimating section 118' compares the thickness change waveform supplied from the thickness change waveform calculating section 116 to the reference waveform supplied from the reference waveform generating section 117D, thereby calculating the greatest thickness change in the thickness change waveform. The thickness change estimating section 118' also calculates an index indicating the degree of matching between these two waveforms. More specifically, the thickness change estimating section 118' calculates a coefficient and a difference to be caused by the use of the coefficient so as to minimize the difference between one of the thickness change and reference waveforms and a waveform obtained by multiplying the other waveform by the coefficient. Then, based on the coefficient and the amplitude of the reference waveform, the thickness change estimating section 118' calculates the greatest thickness change in the thickness change waveform.

The reliability determining section 171 receives the difference that has been calculated by the thickness change estimating section 118' and determines the reliability of either the greatest thickness change or the modulus of elasticity by the value of the difference.

The ultrasonic diagnostic apparatus 207 preferably further includes a modulus of elasticity calculating section 120 for calculating a modulus of elasticity based on the greatest thickness change obtained. The modulus of elasticity calculating section 120 receives information about the stress applied to the subject (e.g., the blood pressure difference ΔP between the highest and lowest blood pressures) from the blood pressure manometer 119, for example. And the modulus of elasticity calculating section 120 calculates the modulus of elasticity Er based on the blood pressure difference ΔP and the greatest thickness change ΔW by Equation (6). In this case, the reference thickness Ws is the distance (e.g., 400 μm) between the two measuring points at which the thickness change waveform was figured out, and is determined in advance by the two measuring points that have been set by the thickness change waveform calculating section 116. In this manner, the modulus of elasticity of the subject can be obtained.

The modulus of elasticity thus obtained is preferably displayed along with the tomographic image of the subject because the location of the measuring point can be shown clearly. For that purpose, the ultrasonic diagnostic apparatus 207 preferably further includes a tomographic image generating section 104, an image synthesizing section 105 and an image display section 106. The tomographic image generating section 104 includes a filter and an amplitude detector and analyzes mainly the amplitude of the received echo signal supplied from the receiving section 103, thereby generating an image signal as a tomographic image representing the subject's internal structure.

The image synthesizing section 105 receives the image signal and the data about the modulus of elasticity that has been supplied from the modulus of elasticity calculating section 120, and synthesizes the image signal and modulus of elasticity data together such that the modulus of elasticity obtained is mapped to an appropriate location on the tomographic image. In this case, the image synthesizing section 105 receives the rate of reliability of the greatest thickness change that has been used to calculate the modulus of elasticity from the reliability determining section 171 and presents the modulus of elasticity according to the rate. For example, if a modulus of elasticity has been calculated based on the greatest thickness change, of which the reliability has been determined to be low, then the modulus of elasticity does not have to be presented. Then, only moduli of elasticity with high reliability are presented on the image display section 106. That is why a high-reliability diagnosis can be made based on the modulus of elasticity presented on the image display section 106.

Hereinafter, it will be described in further detail how the reference waveform generating section 117D, the thickness change estimating section 118' and the reliability determining section 171, which are the core sections of the present invention, operate.

As already described for the first preferred embodiment, the reference waveform generating section 117D stores the data about the reference waveform M(t) shown in FIG. 2. This waveform is obtained by figuring out the thickness change waveforms of a plurality of subjects in advance and calculating the average of those waveforms for one cardiac cycle. The reference waveform M(t) is prepared in advance for an object of measurement by the ultrasonic diagnostic apparatus 207. In this preferred embodiment, to calculate the modulus of elasticity of the vessel wall of the arterial canal, the reference waveform, calculated on the vessel walls of the arterial canals of a plurality of subjects, is used as the reference waveform M(t).

ΔW, which is the amplitude of the reference waveform M(t), has been normalized to be a reference value of 1 μm, for example. Since the data collected from a plurality of subjects is averaged, the influence of noise on even the actually collected data has been reduced.

According to the present invention, the greatest thickness change and the modulus of elasticity are calculated based on the reference waveform and actually measured values. That is why it is important to define an appropriate reference waveform. If the thickness change waveform changes differently with time according to the specific measuring site on the subject, then the reference waveform is preferably defined on a site-by-site basis. Specifically, if the modulus of elasticity of the vessel wall of the arterial canal should be calculated, reference waveform data may be provided for the intima, media, and adventitia of the vessel wall, respectively. By storing sets of reference waveform data in the reference waveform generating section 117D and changing those sets of reference waveform data on a site-by-site basis, the thickness change can be estimated even more precisely.

Optionally, a number of different sets of reference waveform data may also be stored in the storage section of the reference waveform generating section 117D according to the physical condition of the subject, e.g., a reference waveform for healthy persons, a reference waveform for diabetics, and a reference waveform for patients with arterial sclerosis. And one of those reference waveforms may be selected in accordance with the operator's instruction. Then, the thickness change can be estimated even more accurately.

As already described for the first preferred embodiment, FIG. 3 shows the thickness change waveform y(t) obtained by the thickness change waveform calculating section 116. This thickness change waveform is a portion of the waveform obtained by actually inspecting the subject for one cardiac cycle. In this case, t represents the sampling time and is an integer, i.e., t=0, 1, ... and N−1, where N is the number of sample points.

As also described for the first preferred embodiment, the thickness change estimating section 118' receives the reference waveform M(t) and the thickness change waveform y(t) and calculates, by the minimum square method, how many times the amplitude of the thickness change waveform y(t) should be multiplied to make the product closest to the reference waveform M(t). If the coefficient to be multiplied by y(t) is k and the square of the difference between M(t) and k·y(t) is R, then R is given by Equation (7) that has been described for the first preferred embodiment.

If Equation (7) is subjected to partial differentiation using the coefficient k as a variable (Equation (8)) and if the resultant equation becomes equal to zero, then the squared difference R will be minimum. By resolving Equation (8) with respect to k, Equation (9) is obtained.

The value of the coefficient k obtained by Equation (9) means that if the thickness change waveform y(t) calculated is multiplied by k, then the square of the difference from the reference waveform M(t) with an amplitude of 1 μm will be minimum and the two waveforms will match most closely to each other. That is why the amplitude A of the thickness change waveform y(t) measured can be calculated by Equation (10).

The thickness change estimating section 118' further substitutes the k value calculated by Equation (9) into Equation (7) to figure out R. Since k is determined so as to minimize the squared difference R, this R will be referred to herein as $R_{min}$. That is to say, $R_{min}$ is calculated by the following Equation (19).

$$R_{min} = \sum_{t=0}^{N-1} \left( M(t) - \frac{\sum_{t=0}^{N-1} M(t)y(t)}{\sum_{t=0}^{N-1} (y(t))^2} y(t) \right)^2 \quad (19)$$

$R_{min}$ represents a difference between the reference waveform M(t) and the thickness change waveform y(t) multiplied by the coefficient k.

As already described for the first preferred embodiment, the thickness change estimating section 118' may also determine how many times the amplitude of the reference waveform M(t) should be multiplied to make the product closest to the actual thickness change waveform y(t). In that case, if the coefficient to be multiplied by the reference waveform M(t) is a and if the residual is R', then the residual R' can be calculated by Equation (12) that has been described for the first preferred embodiment.

If R' is supposed to be zero when subjected to partial differentiation with the coefficient a as in Equation (13) and if R' is resolved with respect to a, then Equation (14) is obtained. In that case, the coefficient a means that if the reference waveform with an amplitude of 1 μm is multiplied by a, then the square of the difference from the actual thickness change waveform y(t) will be minimum and the two waveforms will match most closely to each other. That is why the amplitude A' of the thickness change waveform y(t) can be calculated by Equation (15).

Also, the difference R'min is calculated by the following Equation (20).

$$R'_{min} = \sum_{t=0}^{N-1} \left( \frac{\sum_{t=0}^{N-1} M(t)y(t)}{\sum_{t=0}^{N-1} (M(t))^2} M(t) - y(t) \right)^2 \quad (20)$$

As described above, the thickness change estimating section 118' receives the reference waveform M(t) and the thickness change waveform y(t) and calculates either the coefficient k or the coefficient a that would minimize the matching error between the reference waveform M(t) and the thickness change waveform y(t) by either Equation (9) or Equation (13). Then, based on the coefficient k or a thus calculated, the thickness change estimating section 118' further calculates the greatest thickness change as the amplitude of the thickness change waveform. Furthermore, the thickness change estimating section 118' also calculates the difference $R_{min}$ or $R'_{min}$ by Equation (19) or (20) and then outputs it to the reliability determining section 171.

The reason why the greatest thickness change can be obtained by comparing the reference waveform M(t) and the thickness change waveform y(t) to each other has already been described for the first preferred embodiment with reference to FIG. 4. Consequently, according to the present invention, the greatest thickness change or the modulus of elasticity can be calculated highly accurately without being affected by suddenly produced noise such as spike noise.

As also described for the first preferred embodiment, the greatest thickness change can be estimated without being affected by noise so much as in the conventional method even by using only a portion of one cardiac cycle of the thickness change waveform. Nevertheless, the longer the selected interval, the more accurate the greatest thickness change estimated will be. That is why it is most preferable to calculate the greatest thickness change by comparing one full cardiac cycle of the thickness change waveform to the reference waveform.

The reliability determining section 171 receives the difference $R_{min}$ or $R'_{min}$ and determines, by the value of the difference $R_{min}$ or $R'_{min}$, whether the greatest thickness change calculated by the thickness change estimating section 118' or the modulus of elasticity calculated by the modulus of elasticity calculating section 120 is reliable or not. FIG. 18 is a flowchart showing how the reliability determining section 171 operates on receiving the difference $R_{min}$. As shown in FIG. 18, the reliability determining section 171 receives the difference $R_{min}$ to start a reliability determining operation in Step 301. First, the reliability determining section 171 compares the difference $R_{min}$ to a predetermined threshold value TH2 in Step 302. If the difference $R_{min}$ received is not smaller than the predetermined threshold value TH2, then it means that the reference waveform M(t) does not match the thickness change waveform y(t) multiplied by the coefficient k. That is why the greatest thickness change thus obtained and the modulus of elasticity calculated based on the greatest thickness change are not likely to be correct values and the reliability is determined to be low in Step 305.

On the other hand, if the difference $R_{min}$ received is smaller than the predetermined threshold value TH2, then it means that the reference waveform M(t) agrees well with the thickness change waveform y(t) multiplied by the coefficient k. In that case, however, the difference $R_{min}$ could be smaller than the predetermined threshold value TH2 because the coefficient k is negative. That is to say, the reference waveform M(t) and the thickness change waveform y(t) might have opposite signs. To eliminate such possibility, the reliability determining section 171 preferably receives the coefficient kc from the thickness change estimating section 118' and determines in Step 303 whether the coefficient k has the positive sign or the negative sign. If the coefficient k is not positive, then the reference waveform M(t) and the thickness change waveform y(t) have opposite signs. That is why the greatest thickness change and the modulus of elasticity calculated based on the greatest thickness change are not likely to be correct values and the reliability is determined to be low in Step 306. On the other hand, if the coefficient k is positive, the greatest thickness change and the modulus of elasticity should be correct values and the reliability is determined to be high in Step 304.

The reliability determining section 171 outputs these decision results to the image synthesizing section 105. In accordance with these decisions, the image synthesizing section 105 displays the modulus of elasticity as described above. If the modulus of elasticity is calculated two-dimensionally, the thickness change waveform y(t) is figured out at each location and then subjected to the computation by the thickness change estimating section 118' and the decision by the reliability determining section 171, thereby determining the reliability of the modulus of elasticity at each location to be displayed two-dimensionally.

The method of displaying the modulus of elasticity may be selected arbitrarily. For example, the modulus of elasticity may be displayed in a grayscale tone or color shade associated with its value, and a modulus of elasticity, of which the reliability has been determined to be low, may be displayed in a contrasting color shade that is clearly different from any of these grayscale tones or color shades. Alternatively, if there is a region with a modulus of elasticity, of which the reliability has been determined to be low, then the modulus of elasticity may be interpolated with a modulus of elasticity in a surrounding region, of which the reliability has been determined to be high, and the interpolated value may be displayed as the modulus of elasticity of the former region. Also, if such regions with low-reliability moduli of elasticity account for a predetermined percentage or more of the entire subject, then the presentation of the image representing the moduli of elasticity of that cardiac cycle may be omitted completely.

The ultrasonic diagnostic apparatus 207 estimates the greatest thickness change by comparing the reference waveform and the thickness change waveform to each other. For that reason, even if suddenly produced noise is superposed on the thickness change waveform, the greatest thickness change and the modulus of elasticity can be calculated even more accurately. In addition, since the reliability of the modulus of elasticity thus calculated is determined by the difference between the reference waveform M(t) and the thickness change waveform y(t), the operator can determine whether or not the measurements have been done properly. Consequently, the modulus of elasticity can be measured with high reliability and accuracy by using the ultrasonic diagnostic apparatus 207. Among other things, even if the diseased site in question is hard to identify on a tomographic image but has a different modulus of elasticity from its surrounding regions, that diseased site can be identified with high likelihood.

Embodiment 8

Hereinafter, an eighth preferred embodiment of an ultrasonic diagnostic apparatus according to the present invention will be described. FIG. 19 is a block diagram showing the configuration of the ultrasonic diagnostic apparatus 208, which further includes a period adjusting section 140 and an averaging section 170 that are not included in the ultrasonic diagnostic apparatus 207 of the seventh preferred embodiment described above. The transmitting section 102, receiving section 103, computing section 151 and thickness change estimating section 118' of the ultrasonic diagnostic apparatus 202 have the same functions as the counterparts of the ultrasonic diagnostic apparatus 207 of the seventh preferred embodiment.

As already described for the second preferred embodiment, the period adjusting section 140 adjusts the period of the thickness change waveform such that the period of the thickness change waveform figured out by the thickness change waveform calculating section 116 matches that of the reference waveform generated by the reference waveform calculating section 117D. For that purpose, the ultrasonic diagnostic apparatus 208 receives information about the period of subject's stress variation from an external period detecting section 141. If the subject is the vessel wall of the arterial canal, then a variation in the blood pressure, electrocardiogram or electrocardiophonogram of the subject may be used. For example, an electrocardiograph for detecting the cardiac cycle of the heart may be used effectively as the period detecting section 141.

Portions (a), (b) and (c) of FIG. 7 show the electrocardiogram provided by the period detecting section 141, the thickness change waveform y(t) figured out by the thickness change waveform calculating section 116, and the reference waveform M(t) generated by the reference waveform generating section 117D. As shown in portion (a) of FIG. 7, an R wave is observed in the electrocardiogram. Meanwhile, as is clear from portions (a) and (b) of FIG. 7, the period of the electrocardiogram agrees with the period Ty of the thickness change waveform y(t). This is because the variation in the thickness of the vessel wall of the arterial canal is caused by the variation in the blood pressure due to the heartbeat. On the other hand, as is clear from portions (b) and (c) of FIG. 7, the period Tm of the reference waveform M(t) does not agree with the period Ty of the thickness change waveform y(t).

To resolve the disagreement in period between the reference waveform M(t) and the thickness change waveform y(t), the period adjusting section 140 adjusts the period of the thickness change waveform y(t) based on the information about the period of the subject's stress variation provided by the period detecting section 141. In this preferred embodiment, the period adjusting section 140 detects the period of the R wave of the electrocardiogram, thereby extending or shrinking the thickness change waveform y(t) figured out by the thickness change waveform calculating section 116 along the time axis. The thickness change waveform y'(t), which has been extended or shrunk along the time axis and of which the period has been adjusted, may be given by the following Equation (21).

$$y'(t) = M(t \cdot Tm/Ty) \quad (21)$$

In this case, unless t×Tm/Ty becomes an integer, an interpolated value is generated based on the relation between t and y(t). Optionally, the y(t) values may be stored on a sufficiently fine sampling unit and a value in the closest proximity could be used as an alternative value.

Figure 20:
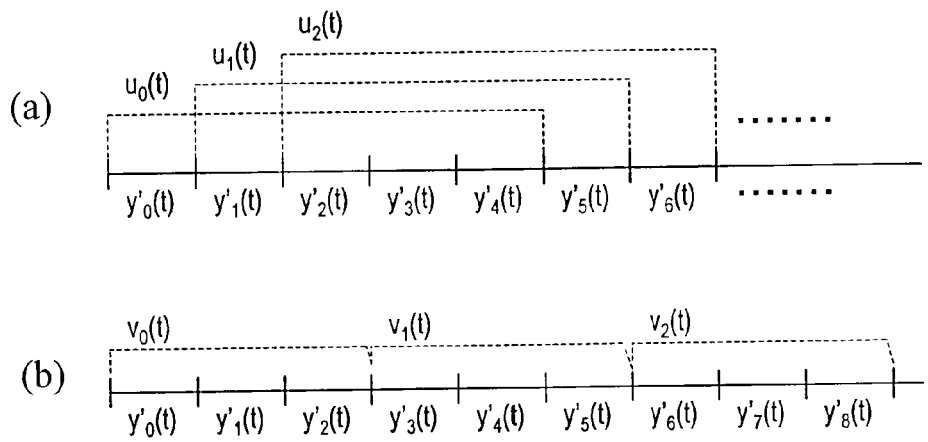

The averaging section 170 calculates the average of the thickness change waveform y'(t), of which the period has been adjusted, over multiple periods. The average may be calculated by any of various methods. For example, if the method of moving averages, in which multiple periods to calculate the average in are sequentially shifted, is adopted as shown in FIG. 20(*a*), the averaged thickness change waveform $u_m(t)$ can be calculated by the following Equation (22).

$$u_m(t) = \frac{1}{L} \sum_{i=m}^{L+m-1} y'_i(t) \quad (22)$$

Here, $y'_i(t)$ represents a thickness change waveform, of which the $i^{th}$ period has been adjusted, and L represents the number of cardiac cycles to be averaged. Equation (22) indicates that the thickness change waveform of the $m^{th}$ period is obtained. On the other hand, if the average is calculated every $L^{th}$ period as shown in FIG. 20(*b*), then the averaged thickness change waveform vm(t) can be calculated by the following Equation (23).

$$v_m(t) = \frac{1}{L} \sum_{i=m \times L}^{(m+1) \times L - 1} y'_i(t) \quad (23)$$

The number L of cardiac cycles to be averaged may be arbitrarily selected. According to Equations (22) and (23), the average is supposed to be calculated by simply adding the thickness change waveforms together. Optionally, the average of weighted sum may also be calculated. If the average is calculated by Equation (22), the averaged thickness change waveform u(t) has the same number of periods as the thickness change waveform y'(t). On the other hand, if the average is calculated by Equation (23), the number of periods of the averaged thickness change waveform v(t) is 1/L of that of the thickness change waveform y'(t).

The averaging section 170 further calculates the variance $\sigma_m^2$ of the signal over the multiple periods, in which the average has been calculated, by one of the following Equations (24) and (25).

$$\sigma_m^2 = \sum_{j=0}^{N-1} \left( \frac{1}{L} \sum_{i=m}^{L+m-1} (y'_i(j) - u_m(j))^2 \right) \quad (24)$$

$$\sigma_m^2 = \sum_{j=0}^{N-1} \left( \frac{1}{L} \sum_{i=m \times L}^{(m+1) \times L - 1} (y'_i(j) - v_m(j))^2 \right) \quad (25)$$

The variance $\sigma_m^2$ is a value representing the degree of variation in signal level over the periods in which the average has been calculated, and is calculated every period of the averaged thickness change waveform. This variance $\sigma_m^2$ is input to the reliability determining section 171'.

The averaged thickness change waveform u(t) (or v(t)) obtained by the averaging section 170 is supplied to the thickness change estimating section 118', which calculates the greatest thickness change and the difference $R_{min}$ as already described for the first preferred embodiment by using u(t) (or v(t)) instead of y(t).

The reliability determining section 171' rates the reliabilities of the greatest thickness change and the modulus of elasticity based on not only the difference $R_{min}$ that has been described for the first preferred embodiment but also the variance a $\sigma_m^2$. FIG. 21 is a flowchart showing how the reliability determining section 171' operates on receiving the difference $R_{min}$ and the variance $\sigma_m^2$. As shown in FIG. 21, the reliability determining section 171' receives the difference $R_{min}$ and the variance $\sigma_m^2$ to start a reliability determining operation in Step 311. First, the reliability determining section 171' compares the variance $\sigma_m^2$ to a predetermined threshold value TH1 in Step 312. If the variance $\sigma_m^2$ is not smaller than the predetermined threshold value TH1, then it means that variation in data between pulses was significant in the averaged thickness change waveform u(t) on which the modulus of elasticity was calculated. That is why the reliability of the modulus of elasticity obtained is determined to be low in Step 316.

On the other hand, if the variance $\sigma_m^2$ is smaller than the predetermined threshold value TH1, then the difference $R_{min}$ is compared to a predetermined threshold value TH2 in Step 313. If the difference $R_{min}$ is not smaller than the predetermined threshold value TH2, then it means that the reference waveform M(t) does not match the thickness change waveform y(t) multiplied by the coefficient k. That is why the greatest thickness change thus obtained and the modulus of elasticity calculated based on the greatest thickness change are not likely to be correct values and the reliability is determined to be low in Step 317.

However, if the difference $R_{min}$ is smaller than the predetermined threshold value TH2, it means that the reference waveform M(t) agrees well with the thickness change waveform y(t) multiplied by the coefficient k. Nevertheless, as described for the first preferred embodiment, the difference $R_{min}$ could be smaller than the predetermined threshold value TH2 because the coefficient k is negative. In view of this possibility, the reliability determining section 171 receives the coefficient k from the thickness change estimating section 118' and determines in Step 314 whether the coefficient k has the positive sign or the negative sign. If the coefficient k is not positive, then the reference waveform M(t) and the thickness change waveform y(t) multiplied by the coefficient k have opposite signs. That is why the greatest thickness change and the modulus of elasticity calculated based on the greatest thickness change are not likely to be correct values and the reliability is determined to be low in Step 318. On the other hand, if the coefficient k is positive, the greatest thickness change and the modulus of elasticity should be correct values and the reliability is determined to be high in Step 315.

The reliability determining section 171' outputs these decision results to the image synthesizing section 105. In accordance with these decisions, the image synthesizing section 105 displays the modulus of elasticity as already described for the first preferred embodiment.

The ultrasonic diagnostic apparatus 208 rates the reliabilities of the greatest thickness change and the modulus of elasticity by not only the difference between the reference waveform and the thickness change waveform but also the variance of the thickness change waveform. That is why the reliabilities of the greatest thickness change and the modulus of elasticity can be determined more accurately.

In this preferred embodiment, the reliabilities of the greatest thickness change and the modulus of elasticity are determined by the difference between the reference waveform and the thickness change waveform and by the variance of the thickness change waveform. Alternatively, the reliabilities of the greatest thickness change and the modulus of elasticity may also be determined only by the variance of the thickness change waveform. This is because if the variance of the thickness change waveform is equal to or smaller than a predetermined threshold value, then it is highly probable that there is a hardly varied continuous thickness change waveform that agrees well with the reference waveform but it is much less likely that there is hardly varied, continuous but inappropriate thickness change waveform that disagrees with the reference waveform. Also, in that case, there is no need to calculate the difference.

In the preferred embodiments described above, the modulus of elasticity is supposed to be displayed. However, the greatest thickness change or the magnitude of strain may also be displayed according to the result of the decision made by the reliability determining section.

Embodiment 9

Hereinafter, a ninth preferred embodiment of an ultrasonic diagnostic apparatus according to the present invention will be described. FIG. 22 is a block diagram showing the configuration of an ultrasonic diagnostic apparatus 209, which includes a transmitting section 102, a receiving section 103, a computing section 151, a reference waveform generating section 117E, a thickness change estimating section 118" and a tissue identifying section 172. The ultrasonic diagnostic apparatus 209 also includes a control section 100 for controlling all of these components of its own.

The transmitting section 102, the receiving section 103 and the computing section 151 of the ultrasonic diagnostic apparatus 209 function in the same way as the counterparts of the first or seventh preferred embodiment described above. Specifically, in accordance with the instruction given by the control section 100, the transmitting section 102 generates a drive signal to drive a probe 101 at a predetermined timing. In response to the drive signal, the probe 101 transmits an ultrasonic wave. The ultrasonic wave thus transmitted soon reaches a subject being deformed periodically under stress and is reflected inside the subject. In this preferred embodiment, the subject includes the vessel wall of an arterial canal and the ultrasonic diagnostic apparatus 209 calculates the modulus of elasticity of the vessel wall. Blood flows through the arterial canal in a period that is synchronized with a cardiac cycle. That is why the vessel wall is deformed periodically under the stress caused by the blood flow.

The receiving section 103 receives an echo, reflected from the subject, at the probe 101. Specifically, the probe 101 converts the echo into an electrical signal, and then the receiving section 103 amplifies the electrical signal, thereby generating a received echo signal. Then the receiving section 103 converts the received echo signal into a digital signal.

The transmitting section 102 and the receiving section 103 preferably include a time delay control section for controlling the time delay caused in the drive signal or the received echo signal in order to scan the subject with the ultrasonic wave transmitted and detect only the ultrasonic wave that has been reflected from a predetermined location or in a predetermined direction. Also, the probe 101 preferably includes an array of ultrasonic oscillators.

The computing section 151 analyzes the received echo signal to track the motions of the subject on multiple measuring points, and also generates a thickness change waveform representing a variation in distance between two arbitrary measuring points on the subject. For that purpose, the computing section 151 includes a displacement waveform calculating section 115 and a thickness change waveform calculating section 116. The displacement waveform calculating section 115 receives the received echo signal and figures out a displacement waveform, representing the displacements of multiple measuring points on the subject, by Equations (1) and (2). The thickness change waveform calculating section 116 figures out a thickness change waveform, representing a variation in distance between two points that have been selected arbitrarily from those measuring points, by calculating the difference between the displacement waveforms of the two measuring points.

Multiple measuring points can be set on a single ultrasonic beam according to the resolution that is defined by the frequency of the ultrasonic wave to be transmitted, for example. That is why by scanning the subject with an ultrasonic beam, the displacement waveforms of respective measuring points, which are arranged two-dimensionally, can be obtained.

The reference waveform generating section 117E generates a reference waveform. This reference waveform is used as a reference for the thickness change waveform to be figured out by the thickness change waveform calculating section 116. In this preferred embodiment, the reference waveform has been figured out in advance by measuring, for example, and the data about the reference waveform is stored in a storage section such as a semiconductor memory for the reference waveform generating section 117E.

As already described for the first and seventh preferred embodiments, the thickness change estimating section 118" compares the thickness change waveform supplied from the thickness change waveform calculating section 116 to the reference waveform supplied from the reference waveform generating section 117E, thereby calculating the greatest thickness change in the thickness change waveform. The thickness change estimating section 118" also calculates an index indicating the degree of matching between these two waveforms. More specifically, the thickness change estimating section 118" calculates a coefficient and a difference to be caused by the use of the coefficient so as to minimize the difference between one of the thickness change and reference waveforms and a waveform obtained by multiplying the other waveform by the coefficient. Then, based on the coefficient and the amplitude of the reference waveform, the thickness change estimating section 118" calculates the greatest thickness change in the thickness change waveform. The greatest thickness change and the difference for each of those reference waveforms are output to the tissue identifying section 172.

Based on the difference that has been calculated on the respective reference waveforms as an index indicating the degree of matching between the thickness change waveform and each reference waveform, the tissue identifying section 172 determines to which of the multiple tissues the tissue that has been located between the two measuring points and produced the thickness change waveform corresponds. More particularly, the tissue identifying section 172 identifies a tissue associated with one of the reference waveforms that has caused the smallest difference as the tissue that has produced the thickness change waveform between the two measuring points and outputs the greatest thickness change that has been calculated based on the reference waveform.

The ultrasonic diagnostic apparatus 209 preferably further includes a modulus of elasticity calculating section 120 for calculating a modulus of elasticity based on the greatest thickness change provided by the tissue identifying section 172. The modulus of elasticity calculating section 120 receives information about the stress applied to the subject (e.g., the blood pressure difference ΔP between the highest and lowest blood pressures) from the blood pressure manometer 119, for example. And the modulus of elasticity calculating section 120 calculates the modulus of elasticity Er based on the blood pressure difference ΔP and the greatest thickness change ΔW by Equation (6). In this case, the reference thickness Ws is the distance (e.g., 400 μm) between the two measuring points at which the thickness change waveform was figured out, and is determined in advance by the two measuring points that have been set by the thickness change waveform calculating section 116. In this manner, the modulus of elasticity of the subject can be obtained.

The modulus of elasticity thus obtained is preferably displayed along with the tomographic image of the subject because the location of the measuring point can be shown clearly. For that purpose, the ultrasonic diagnostic apparatus 209 preferably further includes a tomographic image generating section 104, an image processing section 105 and an image display section 106. The tomographic image generating section 104 includes a filter and an amplitude detector and analyzes mainly the amplitude of the received echo signal supplied from the receiving section 103, thereby generating an image signal as a tomographic image representing the subject's internal structure.

The image processing section 105 receives the image signal and the data about the modulus of elasticity that has been supplied from the modulus of elasticity calculating section 120, and synthesizes the image signal and modulus of elasticity data together such that the modulus of elasticity obtained is mapped to an appropriate location on the tomographic image. In this case, the image processing section 105 is notified by the tissue identifying section 172 of the tissue in which the measuring spot is now located and displays the modulus of elasticity according to the result of identification. For example, the modulus of elasticity may be displayed in one of multiple different colors that is associated with the identified tissue and in a gray scale tone (luminance) that is associated with the value of the modulus of elasticity. In this manner, the modulus of elasticity can be calculated accurately and the region displayed in a predetermined color so as to identify the tissue with the modulus of elasticity can be easily located in the subject. Consequently, high reliability diagnosis can be made based on the modulus of elasticity displayed on the image display section 106.

Hereinafter, it will be described in further detail how the reference waveform generating section 117E, the thickness change estimating section 118", the tissue identifying section 172 and the image processing section 105, which are the core sections of the present invention, operate. First, the subject as the object of measurement of this preferred embodiment will be described. FIG. 23 schematically illustrates a cross section of the arterial canal of the subject. As shown in FIG. 23, the cross section of the arterial canal, as viewed on a plane that includes the axis of the arterial canal, has vessel walls 30' and 30 that interpose a vascular lumen 40 between them. When these vessel walls 30' and 30 need to be distinguished from each other, the vessel wall 30' that is located closer to the subject's surface will be referred to herein as a "vessel anterior wall", while the other wall a "vessel posterior wall" 30. Each of these vessel walls 30' and 30 has a three-layer structure in which three different tissues are stacked one upon the other concentrically, and includes an intima 33, 33' adjacent to the vascular lumen 40, an adventitia 32, 32' located in the outermost region, and a media 34, 34' interposed between them. The intima 33 and the media 34 will be collectively referred to herein as an intima-media complex 31, while the intima 33' and the media 34' will be collectively referred to herein as an intima-media complex 31'. In this preferred embodiment, to measure the moduli of elasticity of the vessel walls 30' and 30, reference waveforms are provided for the intima 33, 33', media 34, 34' and adventitia 32, 32', respectively.

FIGS. 24(a), 24(b) and 24(c) respectively show the reference waveforms $M_1(t)$ to $M_3(t)$ that are stored in the storage section of the reference waveform generating section 117E. These waveforms are obtained by figuring out the thickness change waveforms of the intima 33, 33', media 34, 34' and adventitia 32, 32' of multiple subjects in advance and calculating the averages thereof for one cardiac cycle. Under the pressure of blood flowing through the vascular lumen 40, the intima 33, 33', media 34, 34' and adventitia 32, 32' of the vessel walls 30' and 30 are subjected to stress and deformed periodically. However, since the respective tissues of the intima 33, 33', media 34, 34' and adventitia 32, 32' have mutually different viscosity properties and elastic properties, their thickness change waveforms are also different from each other as shown in FIGS. 24(a) through 24(c).

ΔW, which is the amplitude of the reference waveforms $M_1(t)$ through $M_3(t)$, has been normalized to be a reference value of 1 μm, for example. Since the data collected from a plurality of subjects is averaged, the influence of noise on even the actually collected data has been reduced.

In this preferred embodiment, to calculate the moduli of elasticity of the vessel walls as described above, the thickness change waveforms of the intima 33, 33', media 34, 34' and adventitia 32, 32' that form each vessel wall are selected as reference waveforms. However, the number of reference waveforms to provide may change depending on the object of measurement. Optionally, a number of different sets of reference waveform data may also be stored in the storage section of the reference waveform generating section 117E according to the physical condition of the subject, e.g., a set of reference waveforms for healthy persons, a set of reference waveforms for diabetics, and a set of reference waveforms for patients with arterial sclerosis. And one of those sets of reference waveforms may be selected in accordance with the operator's instruction. Then, the thickness change can be estimated even more accurately.

As already described for the first and other preferred embodiments, FIG. 3 shows the thickness change waveform y(t) obtained by the thickness change waveform calculating section 116 between two measuring points in a measuring target area. This thickness change waveform is a portion of the waveform obtained by actually inspecting the subject for one cardiac cycle. In this case, t represents the sampling time and is an integer, i.e., t=0, 1, ... and N−1, where N is the number of sample points.

The thickness change estimating section 118" receives the reference waveforms $M_1(t)$ through $M_3(t)$ and the thickness change waveform y(t) and calculates, by the minimum square method, how many times the amplitude of the thickness change waveform y(t) should be multiplied to make the product closest to the reference waveforms $M_1(t)$ through $M_3(t)$. If the coefficients to be multiplied by y(t) are $k_1$ through $k_3$ and the square of the difference between $M_1(t)$ and $k_1 \cdot y(t)$ is $R_1$, then $R_1$ is given by the following Equation (26).

$$R_1 = \sum_{t=0}^{N-1} (M_1(t) - k_1 \cdot y(t))^2 \tag{26}$$

If Equation (26) is subjected to partial differentiation using the coefficient $k_1$ as a variable and if the resultant equation becomes equal to zero as in the following Equation (27), then the squared difference $R_1$ will be minimum.

$$\frac{\partial R_1}{\partial k_1} = 2\sum_{t=0}^{N-1} (-M_1(t)y(t) + k_1(y(t))^2) = 0 \tag{27}$$

By resolving Equation (27) with respect to $k_1$, the following Equation (28) is obtained.

$$k_1 = \frac{\sum_{t=0}^{N-1} M_1(t)y(t)}{\sum_{t=0}^{N-1} (y(t))^2} \tag{28}$$

The value of the coefficient $k_1$ obtained by Equation (9) means that if the thickness change waveform y(t) calculated is multiplied by $k_1$, then the square of the difference from the reference waveform $M_1(t)$ with an amplitude of 1 μm will be minimum and the two waveforms will match most closely to each other. That is why the amplitude $A_1$ of the thickness change waveform y(t) measured can be calculated by the following Equation (29).

$$A_1 = 1/k_1 \text{ (μm)} \tag{29}$$

The thickness change estimating section 118" further substitutes the $k_1$ value calculated by Equation (28) into Equation (26) to figure out $R_1$. Since $k_1$ is determined so as to minimize the squared difference $R_1$, this $R_1$ will be referred to herein as $R_{1m}$. That is to say, $R_{1m}$ is calculated by the following Equation (30).

$$R_{1m} = \sum_{t=0}^{N-1} \left( M_1(t) - \frac{\sum_{t=0}^{N-1} M_1(t)y(t)}{\sum_{t=0}^{N-1} (y(t))^2} y(t) \right)^2 \tag{30}$$

$R_{1m}$ represents a difference between the reference waveform $M_1(t)$ and the thickness change waveform y(t) multiplied by the coefficient $k_1$.

As in the calculation described above, the thickness change estimating section 118" may also determine how many times the amplitude of the reference waveform $M_1(t)$ should be multiplied to make the product closest to the actual thickness change waveform y(t). In that case, if the coefficient to be multiplied by the reference waveform $M_1(t)$ is $k'_1$ and if the residual is $R'_1$, then the residual $R'_1$ can be calculated by the following Equation (31).

$$R'_1 = \sum_{t=0}^{N-1} (k'_1 \cdot M_1(t) - y(t))^2 \tag{31}$$

If $R'_1$ is supposed to be zero when subjected to partial differentiation with $k'_1$ as in the following Equation (32) and if $R'_1$ is resolved with respect to $k'_1$, then the following Equation (33) is obtained.

$$\frac{\partial R'_1}{\partial k'_1} = 2\sum_{t=0}^{N-1} (k'_1(M_1(t))^2 - M_1(t)y(t)) = 0 \tag{32}$$

$$k'_1 = \frac{\sum_{t=0}^{N-1} M_1(t)y(t)}{\sum_{t=0}^{N-1} (M_1(t))^2} \tag{33}$$

In that case, the coefficient $k'_1$ means that if the reference waveform with an amplitude of 1 μm is multiplied by $k'_1$, then the square of the difference from the actual thickness change waveform y(t) will be minimum and the two waveforms will match most closely to each other. That is why the amplitude A' of the thickness change waveform y(t) can be calculated by the following Equation (34).

$$A'_1 = k'_1 \text{ (μm)} \tag{34}$$

Also, the difference $R'_{1m}$ is calculated by the following Equation (35).

$$R'_{1m} = \sum_{t=0}^{N-1} \left( \frac{\sum_{t=0}^{N-1} M_1(t)y(t)}{\sum_{t=0}^{N-1} (M_1(t))^2} M_1(t) - y(t) \right)^2 \tag{35}$$

As for the other reference waveforms $M_2(t)$ and $M_3(t)$, the coefficients $k_2$, $k_3$, the amplitudes $A_2$, $A_3$, and the differences $R_{2m}$, $R_{3m}$ are calculated in the same way by Equations (28) to (30), respectively. The coefficients $k'_2$, $k'_3$, the amplitudes $A'_2$, $A'_3$, and the differences $R'_{2m}$, $R'_{3m}$ may be calculated as described above.

As described above, the thickness change estimating section 118" receives the reference waveforms $M_1(t)$ to $M_3(t)$ and the thickness change waveform y(t) and calculates the amplitudes $A_1$ to $A_3$ and the differences $R_{1m}$ to $R_{3m}$ that would minimize the differences between the reference waveforms $M_1(t)$ to $M_3(t)$ and the thickness change waveform y(t) by Equations (28) and (29). Then, the thickness change estimating section 118″ outputs them to the tissue identifying section 172.

The reason why the greatest thickness change can be obtained by comparing the reference waveforms $M_1(t)$ to $M_3(t)$ and the thickness change waveform y(t) to each other has already been described for the first preferred embodiment with reference to FIG. 4. Consequently, according to the present invention, the greatest thickness change or the modulus of elasticity can be calculated highly accurately without being affected by suddenly produced noise such as spike noise.

As also described for the first preferred embodiment, the greatest thickness change can be estimated without being affected by noise so much as in the conventional method even by using only a portion of one cardiac cycle of the thickness change waveform. Nevertheless, the longer the selected interval, the more accurate the greatest thickness change estimated will be. That is why it is most preferable to calculate the greatest thickness change by comparing one full cardiac cycle of the thickness change waveform to the reference waveform.

As described above, the variation pattern of a thickness change waveform along the time axis changes from one tissue to another. That is why if the difference is calculated by the computation method described above using the reference waveforms provided for the respective tissues, the tissue associated with a reference waveform that results in the smallest difference is the tissue, of which the thickness change waveform has been obtained. The tissue identifying section 172 makes this decision.

FIG. 25 is a flowchart showing how the tissue identifying section 172 operates. After having started its tissue identifying operation in Step 301, the tissue identifying section 172 receives amplitudes $A_1$, $A_2$ and $A_3$ and differences $R_{1m}$, $R_{2m}$ and $R_{3m}$ in Step 302. Alternatively, the tissue identifying section 172 may have received the amplitudes $A_1$, $A_2$ and $A_3$ and differences $R_{1m}$, $R_{2m}$ and $R_{3m}$ in advance and may start its identifying operation in accordance with the instruction given by the control section 100. First, the tissue identifying section 172 compares the differences $R_{1m}$, $R_{2m}$ and $R_{3m}$ to a predetermined threshold value $R_{TH}$ in Step 303. If all of these differences $R_{1m}$, $R_{2m}$ and $R_{3m}$ are greater than the threshold value $R_{TH}$, then it means that the thickness change waveform y(t) is not similar to any of the reference waveforms $M_1(t)$ to $M_3(t)$ and a portion of the tissue where the thickness change waveform y(t) was obtained is not associated with any of the reference waveforms $M_1(t)$ through $M_3(t)$. In that case, the tissue identifying section 172 substitutes zero for the decision result S and for the amplitude A in Step 304.

On the other hand, if at least one of the differences $R_{1m}$, $R_{2m}$ and $R_{3m}$ is smaller than the threshold value $R_{TH}$, the smallest one of the differences $R_{1m}$, $R_{2m}$ and $R_{3m}$ needs to be found. If the difference $R_{1m}$ is the smallest, then it means that the thickness change waveform y(t) is most similar to the reference waveform $M_1(t)$ and that a portion of the tissue where the thickness change waveform y(t) was obtained is associated with the reference waveform $M_1(t)$. That is why one is substituted for the decision result S and $A_1$ is substituted for the amplitude A.

In the same way, if the difference $R_{2m}$ is the smallest, then it means that the thickness change waveform y(t) is most similar to the reference waveform $M_2(t)$ and that a portion of the tissue where the thickness change waveform y(t) was obtained is associated with the reference waveform $M_2(t)$. That is why two is substituted for the decision result S and $A_2$ is substituted for the amplitude A. And if the difference $R_{3m}$ is the smallest, then it means that the thickness change waveform y(t) is most similar to the reference waveform $M_3(t)$ and that a portion of the tissue where the thickness change waveform y(t) was obtained is associated with the reference waveform $M_3(t)$. That is why three is substituted for the decision result S and $A_3$ is substituted for the amplitude A. In this manner, the tissue identifying section 172 completes its identifying operation in Step 306. If the modulus of elasticity needs to be measured two-dimensionally, then the identifying operation is carried out on each point of the two-dimensional matrix.

The tissue identifying section 172 outputs these decision results to the modulus of elasticity calculating section 120 and the image processing section 105. Specifically, the tissue identifying section 172 outputs the amplitude A, for which $A_1$, $A_2$, $A_3$ or zero has been substituted, to the modulus of elasticity calculating section 120 and the decision result S, for which zero, one, two or three has been substituted, to the image processing section 105.

In this preferred embodiment, after the differences $R_{1m}$, $R_{2m}$ and $R_{3m}$ have been compared to the predetermined threshold value $R_{TH}$, the smallest one of the differences $R_{1m}$, $R_{2m}$ and $R_{3m}$ is found. Alternatively, the smallest difference $R_{1m}$, $R_{2m}$ or $R_{3m}$ may be found first, and then compared to the threshold value $R_{TH}$.

The modulus of elasticity calculating section 120 calculates a modulus of elasticity using the received amplitude A as the greatest thickness change $\Delta W$ as described above. If the amplitude A has a value of zero, it means that a correct greatest thickness change has not been obtained and the modulus of elasticity is not calculated. Optionally, a numerical value that can be easily distinguished from a modulus of elasticity calculated properly (e.g., zero) may be substituted for the modulus of elasticity, too.

The image processing section 105 receives the modulus of elasticity from the modulus of elasticity calculating section 120 and generates image data, which should be superposed on the tomographic image, generated by the tomographic image generating section 104, to display the modulus of elasticity, based on the decision result S received from the tissue identifying section 172. The measuring region in which the modulus of elasticity has been calculated is associated with the decision result S showing what tissue that region is associated with. That is why in displaying the moduli of elasticity as a two-dimensional map, the information about the tissue identification and the information about the modulus of elasticity are preferably displayed.

FIG. 26 shows an example of image data that has been generated by the image processing section 105, and displayed on the image display section 106, so as to present respective tissues in different colors and display the modulus of elasticity with a luminance associated with its value. On the image display section 106, presented is a tomographic image 50 that has been generated by the tomographic image generating section 104. The tomographic image 50 represents a vascular lumen 40, an intima 33, a media 34, an adventitia 32 and an extravascular tissue 41. In FIG. 26, the boundaries between the respective tissues are shown clearly. On an actual tomographic image 50, however, these boundaries are often not so definite. Also, although the intima 33 and the media 34 are shown as definitely different ones in FIG. 26, the intima 33 and the media 34 could be shown with similar luminances and could not be distinguished from each other so easily.

On the tomographic image 50, superposed is a two-dimensional map image 56 of moduli of elasticity. Each area of the two-dimensional map image 56 is presented in a color associated with its tissue and in a grayscale associated with its modulus of elasticity. Specifically, based on the thickness change waveform that was used to calculate the modulus of elasticity of the area 52, the tissue identifying section 172 substitutes one for the decision result S of the area 52, i.e., identifies the area 52 as the intima associated with the reference waveform $M_1(t)$. In the same way, the areas 53 and 54 are identified as the media and the adventitia, respectively. On the other hand, the thickness change waveforms obtained from the areas 51 and 55 are not similar to any of the reference waveforms $M_1(t)$ to $M_3(t)$, and therefore, zero is substituted for the decision result S. That is to say, the areas 51 and 55 are identified as none of the intima, media and adventitia. Thus, to show the difference in tissue, the areas 52, 53 and 54 may be presented in yellow, red and brown, respectively, and may display the moduli of elasticity with respective luminances associated with the moduli of elasticity. As shown in FIG. 26, there is a region 57 with a high modulus of elasticity in the area 53 that has been identified as the media. The areas 51 and 55 are none of the intima, media and adventitia, and therefore, may be presented in gray, for example. In the areas 51 and 55, no modulus of elasticity has been calculated.

Optionally, based on the result of the decision made by the tissue identifying section 172, only the modulus of elasticity of an area that has been identified as a particular tissue may be displayed. For example, on the two-dimensional map image 56 that is superposed on the tomographic image 50 to represent moduli of elasticity, only the area 53 that has a decision result S of two and that has been identified as the media is presented with a luminance associated with its modulus of elasticity as shown in FIG. 27.

As shown in FIG. 26, the moduli of elasticity of respective tissues are displayed in different colors, and therefore, it can be seen easily that the region 57 with a high modulus of elasticity is located within the media. Consequently, even if the boundaries between the tissues are not definite on the tomographic image 50, the diseased site can be easily spotted correctly. Among other things, if only the modulus of elasticity of a particular tissue is displayed as shown in FIG. 27, the diseased site can be spotted more easily by the modulus of elasticity. Besides, the boundary between the intima and media of a vessel wall and the boundary between the media and adventitia thereof that have been difficult to distinguish with a conventional tomographic image can also be located.

As described above, according to the present invention, the greatest thickness change is estimated by comparing the reference waveform and the thickness change waveform to each other. That is why even if suddenly produced noise is superposed on the thickness change waveform, the greatest thickness change and the modulus of elasticity can be calculated more accurately. In addition, since it is determined, as a piece of information about the subject's internal tissue, from what tissue of the subject the modulus of elasticity calculated has been derived, it can be seen easily what tissue of the subject a portion with a unique modulus of elasticity belongs to. Among other things, even if a tissue is difficult to locate on a B-mode image, it can be determined what tissue of the subject has such a portion with a unique modulus of elasticity.

Embodiment 10

Hereinafter, a tenth preferred embodiment of an ultrasonic diagnostic apparatus according to the present invention will be described. FIG. 28 is a block diagram showing the configuration of an ultrasonic diagnostic apparatus 210, which not only calculates the modulus of elasticity of the given subject using an ultrasonic wave but also estimates the viscosity coefficient of the subject as his or her internal tissue information. By calculating the viscosity coefficient as additional information, even a plurality of tissues, which would be difficult to tell only by their moduli of elasticity, can be distinguished from each other. For that purpose, the ultrasonic diagnostic apparatus includes a transmitting section 102, a receiving section 103, a computing section 151, a reference waveform generating section 117F, a comparing section 125, and a viscosity coefficient determining section 121. The ultrasonic diagnostic apparatus 210 also includes a control section 100 for controlling all of these components of its own.

The transmitting section 102, the receiving section 103 and the computing section 151 of the ultrasonic diagnostic apparatus 210 function in the same way as the counterparts of the first preferred embodiment described above.

Specifically, in accordance with the instruction given by the control section 100, the transmitting section 102 generates a drive signal to drive a probe 101 at a predetermined timing. In response to the drive signal, the probe 101 transmits an ultrasonic wave. The ultrasonic wave thus transmitted soon reaches a subject being deformed periodically under stress and is reflected inside the subject. In this preferred embodiment, the subject includes the vessel wall of an arterial canal and the ultrasonic diagnostic apparatus 210 calculates the modulus of elasticity of the vessel wall. Blood flows through the arterial canal in a period that is synchronized with a cardiac cycle. That is why the vessel wall is deformed periodically under the stress caused by the blood flow.

The receiving section 103 receives an echo, reflected from the subject, at the probe 101, converts the echo into an electrical signal, and then amplifies the electrical signal, thereby generating a received echo signal. The receiving section 103 also converts the received echo signal into a digital signal.

The transmitting section 102 and the receiving section 103 preferably include a time delay control section for controlling the time delay caused in the drive signal or the received echo signal in order to scan the subject with the ultrasonic wave transmitted and detect only the ultrasonic wave that has been reflected from a predetermined location or in a predetermined direction. Also, the probe 101 preferably includes an array of ultrasonic oscillators.

The computing section 151 analyzes the received echo signal to track the motions of the subject on multiple measuring points, and also generates a thickness change waveform representing a variation in distance between two arbitrary measuring points on the subject. For that purpose, the computing section 151 includes a displacement waveform calculating section 115 and a thickness change waveform calculating section 116. The displacement waveform calculating section 115 receives the received echo signal and figures out a displacement waveform, representing the displacements of multiple measuring points on the subject, by Equations (1) and (2). The thickness change waveform calculating section 116 figures out a thickness change waveform, representing a variation in distance between two points that have been selected arbitrarily from those measuring points, by calculating the difference between the displacement waveforms of the two measuring points.

Multiple measuring points can be set on a single ultrasonic beam according to the resolution that is defined by the frequency of the ultrasonic wave to be transmitted, for example. That is why by scanning the subject with an ultrasonic beam, the displacement waveforms of respective measuring points, which are arranged two-dimensionally, can be obtained.

The reference waveform generating section 117F generates an elastic property reference waveform and a plurality of viscosity property reference waveforms. As will be described in detail later, these reference waveforms are used as a reference for the thickness change waveform to be figured out by the comparing section 125. In this preferred embodiment, the elastic property reference waveform is generated by getting a blood pressure waveform, representing a variation in the blood pressure in the arterial canal of the subject, from a real-time blood pressure manometer 150 and adjusting its amplitude. A number of viscosity property reference waveforms are also generated based on the blood pressure waveform. Each of those viscosity property reference waveforms is a waveform representing the subject's strain to be obtained based on the blood pressure waveform when the viscosity is supposed to have a predetermined value.

The comparing section 125 has two functions, one of which relates to calculating a modulus of elasticity and the other of which relates to estimating a viscosity coefficient. More specifically, to calculate the modulus of elasticity, the comparing section 125 compares the thickness change waveform supplied from the thickness change waveform calculating section 116 to the elastic property reference waveform supplied from the reference waveform generating section 117F, thereby calculating the greatest thickness change in the thickness change waveform. More specifically, the comparing section 125 determines the coefficient so as to minimize the difference between a waveform obtained by multiplying one of the thickness change and elastic property reference waveforms by the coefficient and the other waveform. Then, based on the coefficient and the amplitude of the elastic property reference waveform thus determined, the comparing section 125 calculates the greatest thickness change. This function is the same as that of the thickness change estimating section 118 of the first and other preferred embodiments described above.

The comparing section 125 of this preferred embodiment not only performs the function of the thickness change estimating section 118 described above but also compares each of multiple viscosity property reference waveforms to the thickness change waveform and calculates a viscosity property index indicating the degree of matching between each viscosity property reference waveform and the thickness change waveform to estimate the viscosity coefficient. More specifically, the comparing section 125 calculates differences in a situation where the coefficient is determined so as to minimize the difference between a waveform obtained by multiplying one of the thickness change and the viscosity property reference waveforms by the coefficient and the other waveform, and outputs those differences as viscosity property indices. The comparing section 125 calculates the modulus of elasticity and estimates the viscosity coefficient every period of the thickness change waveform.

The viscosity coefficient determining section 121 estimates the viscosity coefficient based on the viscosity property indices. More specifically, the viscosity coefficient determining section 121 compares the differences that have been calculated based on the respective viscosity property reference waveforms to each other, thereby determining a viscosity property reference waveform that would minimize the difference. Since those viscosity property reference waveforms have been calculated on the supposition that the viscosity coefficient has a predetermined value, that value of the viscosity coefficient that the viscosity property reference waveform determined is supposed to have becomes the viscosity coefficient at a site of the subject where the estimated thickness change waveform was obtained.

The ultrasonic diagnostic apparatus 210 preferably further includes a modulus of elasticity calculating section 120 for calculating a modulus of elasticity based on the greatest thickness change thus obtained. The modulus of elasticity calculating section 120 receives information about the stress applied to the subject (e.g., the blood pressure difference $\Delta P$ between the highest and lowest blood pressures) from the real-time blood pressure manometer 150, for example. And the modulus of elasticity calculating section 120 calculates the modulus of elasticity Er based on the blood pressure difference $\Delta P$ and the greatest thickness change $\Delta W$ by Equation (6). In this case, the reference thickness Ws is the distance (e.g., 400 μm) between the two measuring points at which the thickness change waveform was figured out, and is determined in advance by the two measuring points that have been set by the thickness change waveform calculating section 116. In this manner, the modulus of elasticity of the subject can be obtained.

The modulus of elasticity and viscosity coefficient thus obtained are preferably displayed along with the tomographic image of the subject because the location of the measuring point can be shown clearly. For that purpose, the ultrasonic diagnostic apparatus 210 preferably further includes a tomographic image generating section 104, an image synthesizing section 105 and an image display section 106. The tomographic image generating section 104 includes a filter and an amplitude detector and analyzes mainly the amplitude of the received echo signal supplied from the receiving section 103, thereby generating an image signal as a tomographic image representing the subject's internal structure.

The image synthesizing section 105 receives the image signal, the data about the modulus of elasticity supplied from the modulus of elasticity calculating section 120 and the data about the viscosity coefficient supplied from the viscosity coefficient determining section 121, and synthesizes the image signal and modulus of elasticity data together such that the viscosity coefficient and modulus of elasticity obtained are mapped to appropriate locations on the tomographic image. The image display section 106 presents the synthesized image thereon. To show the viscosity coefficient and the modulus of elasticity at the same time, two tomographic images representing the viscosity coefficient and the modulus of elasticity, respectively, may be presented on two image display sections 106. Alternatively, a single tomographic image may be presented on the image display section 106 and the viscosity coefficient and the modulus of elasticity may be selectively shown in accordance with the operator's instruction.

Hereinafter, it will be described in further detail how to calculate the modulus of elasticity and how to estimate the viscosity coefficient. First, it will be described in detail how to calculate the modulus of elasticity.

One period of the elastic property reference waveform M(t) output by the reference waveform generating section 117F has a waveform such as that shown in FIG. 2. This waveform represents a variation in the blood pressure in the arterial canal of the subject and is acquired by the real-time blood pressure manometer 150, for example. $\Delta W$, which is the amplitude of the elastic property reference waveform M(t), has been normalized to be a reference value of 1 μm, for example.

Also, the thickness change waveform y(t) obtained by the thickness change waveform calculating section 116 may have the waveform shown in FIG. 3, for example. This thickness change waveform is a portion of the waveform obtained by actually inspecting the subject for one cardiac cycle. In this case, t represents the sampling time and is an integer, i.e., t=0, 1, ... and N−1, where N is the number of sample points.

Just like the thickness change estimating section 118 that has been described for the first preferred embodiment, the comparing section 125 receives the elastic property reference waveform M(t) and the thickness change waveform y(t) and calculates, by the minimum square method, how many times the amplitude of the thickness change waveform y(t) should be multiplied to make the product closest to the elastic property reference waveform M(t). If the coefficient to be multiplied by y(t) is k and the square of the difference between M(t) and k·y(t) is R, then R is given by Equation (7) that has been described for the first preferred embodiment.

If Equation (7) is subjected to partial differentiation using the coefficient k as a variable (Equation (8)) and if the resultant equation becomes equal to zero, then the squared difference R will be minimum. Therefore, by resolving Equation (8) with respect to k, Equation (9) is obtained. The value of the coefficient k obtained by Equation (9) means that if the thickness change waveform y(t) calculated is multiplied by k, then the square of the difference from the elastic property reference waveform M(t) with an amplitude of 1 µm will be minimum and the two waveforms will match most closely to each other. That is why the amplitude A of the thickness change waveform y(t) measured can be calculated by Equation (10).

As already described for the first preferred embodiment, the comparing section 125 may also determine how many times the amplitude of the elastic property reference waveform M(t) should be multiplied to make the product closest to the actual thickness change waveform y(t). In that case, if the coefficient to be multiplied by the elastic property reference waveform M(t) is a, the residual R' is obtained by Equation (11). If R' is supposed to be zero when subjected to partial differentiation with the coefficient a as in Equation (12) and if R' is resolved with respect to a, then Equation (13) is obtained.

In that case, the coefficient a means that if the elastic property reference waveform with an amplitude of 1 µm is multiplied by a, then the square of the difference from the actual thickness change waveform y(t) will be minimum and the two waveforms will match most closely to each other. That is why the amplitude A' of the thickness change waveform y(t) can be calculated by Equation (14).

As described above, the comparing section 125 receives the elastic property reference waveform M(t) and the thickness change waveform y(t) and calculates either the coefficient k or the coefficient a that would minimize the difference between the elastic property reference waveform M(t) and the thickness change waveform y(t) by either Equation (9) or Equation (13). Then, based on the coefficient k or a thus calculated, the comparing section 125 further calculates the greatest thickness change as the amplitude of the thickness change waveform.

The reason why the greatest thickness change can be obtained by comparing the elastic property reference waveform M(t) and the thickness change waveform y(t) to each other has already been described for the first preferred embodiment with reference to FIG. 4. Consequently, according to the present invention, the greatest thickness change or the modulus of elasticity can be calculated highly accurately without being affected by suddenly produced noise such as spike noise.

As also described for the first preferred embodiment, the greatest thickness change can be estimated without being affected by noise so much as in the conventional method even by using only a portion of one cardiac cycle of the thickness change waveform. Nevertheless, the longer the selected interval, the more accurate the greatest thickness change estimated will be. That is why it is most preferable to calculate the greatest thickness change by comparing one full cardiac cycle of the thickness change waveform to the reference waveform.

According to this preferred embodiment, the greatest thickness change and the modulus of elasticity are calculated based on the elastic property reference waveform and the measured value, and therefore, it is important to provide an appropriate elastic property reference waveform. Also, according to this preferred embodiment, since the elastic property reference waveform has been generated based on the subject's blood pressure waveform, the period of the elastic property reference waveform agrees well with that of the thickness change waveform, and these two waveforms can be compared properly to each other. Furthermore, since the variation in the blood pressure of the subject is relatively large and is measured by some established technique, noise superposed on the blood pressure waveform is small. That is why it is effective to use the elastic property reference waveform, generated based on the blood pressure waveform, as a reference for the thickness change waveform to be affected by noise. What is more, as the elastic property reference waveform is generated based on the subject's blood pressure waveform, the individual difference of the subject can be reflected on the elastic property reference waveform.

Next, a method of estimating the viscosity coefficient will be described in detail. A subject's strain waveform is determined by the variation in the stress applied to the subject and the viscosity and elastic property of the subject. Therefore, if a blood pressure waveform p(t) has been obtained, the strain waveform $\epsilon i(t)$, generated on various moduli of elasticity Ei and viscosity coefficients $\eta i$ assumed, should agree with the strain waveform $\epsilon(t)=y(t)/Ws$, obtained based on the thickness change waveform y(t) measured, and the residual between $\epsilon(t)$ and $\epsilon i(t)$ should be zero, provided that the modulus of elasticity Ei and viscosity coefficient $\eta i$ assumed agree with the real modulus of elasticity and real viscosity coefficient of the subject. That is why the viscosity coefficient of the subject is estimated by calculating the residual between $\epsilon(t)$ and $\epsilon i(t)$ and determining the modulus of elasticity Ei and viscosity coefficient $\eta i$ that would minimize the residual.

In this preferred embodiment, a waveform representing the strain of the vessel wall is selected as the reference waveform. Supposing the viscosity coefficients at measuring sites are identified by $\eta 1$, $\eta 2$ and $\eta 3$ and vessel wall strain waveform is generated based on the blood pressure waveform, waveforms such as those identified by $\epsilon 1(t)$, $\epsilon 2(t)$ and $\epsilon 3(t)$ in FIG. 29 are obtained. Having different viscosity coefficients, these waveforms vary differently along the time axis. Comparing the thickness change waveform y(t) to these strain waveforms, the thickness change waveform y(t) and $\epsilon 2(t)$ match most closely to each other although their amplitudes are different. That is why the viscosity coefficient assumed with $\epsilon 2(t)$ is estimated to be the viscosity coefficient at the measuring site.

Hereinafter, the measuring method will be described specifically. First, suppose the subject's blood pressure waveform is identified by p(t) and the vessel wall strain waveform is identified by $\epsilon(t)$. Supposing the Laplace transforms of p(t) and $\epsilon(t)$ are identified by $p(\omega)$ and $\epsilon(\omega)$, respectively, and the transfer function of the vessel wall is identified by $B(\omega)$, the blood pressure waveform $p(\omega)$ is given by the following Equation (36).

$$p(\omega)=B(\omega)\epsilon(\omega) \quad (36)$$

Using Voigt model that is generally used as a model of viscosity or elastic property, the transfer function $B(\omega)$ may be calculated by the following Equation (37).

$$B(\omega)=E'+j\omega\eta' \quad (37)$$

Here, E' is the static modulus of elasticity and $\eta'$ is the viscosity coefficient. The modulus of elasticity E0 calculated based on the elastic property reference waveform satisfies the following Equation (38).

$$E0=|B(\omega)|=E0\sqrt{(E_2+(\omega\eta)^2} \quad (38)$$

where $E'=E0 \cdot E$ and $\omega\eta'=E0 \cdot \omega\eta$. That is why the viscosity coefficient is estimated on the supposition that $E=E'/E0=1$. Specifically, $\eta$ values $\eta 1, \eta 2, \eta 3, \eta, \ldots \eta i, \ldots \eta N$, which increase from zero regularly so as to include all values that are assumed to be the viscosity coefficients of the subject, are set and are substituted for E and $\eta$ of Equation (37), thereby calculating transfer functions $B1(\omega), B2(\omega), B3(\omega), \ldots Bi(\omega), \ldots BN(\omega)$ when the viscosity coefficients are supposed to be respective values. Furthermore, the transfer function $Bi(\omega)$ that has been obtained with the assumed viscosity coefficient $\eta i$ is substituted into the following Equation (39).

$$\epsilon i(\omega)=p(\omega))/Bi(\omega) \quad (39)$$

In this manner, $\epsilon i(\omega)$, $i=1, 2, \ldots N$ are calculated. By subjecting these values to inverse Fourier transform, strain waveforms $\epsilon i(t)$, $i=1, 2, \ldots N$ are calculated. The reference waveform generating section 117F generates these strain waveforms $\epsilon i(t)$, $i=1, 2, \ldots N$ as viscosity property reference waveforms. As described above, in the viscosity property reference waveforms $\epsilon i(t)$, the respective viscosity coefficients are assumed to be $\eta 1, \eta 2, \eta 3, \eta, \ldots \eta i, \ldots \eta N$.

Optionally, on the supposition that the relation between the vessel wall strain waveform $\epsilon(t)$ and the blood pressure waveform $p(t)$ is nonlinear, Equation (36) may be replaced with the following Equation (40).

$$\log(p(\omega))=B(\omega)\epsilon(\omega) \quad (40)$$

Even so, the transfer function $Bi(\omega)$ when the $\eta$ values are also supposed to be $\eta 1, \eta 2, \eta 3, \eta, \ldots \eta i, \ldots \eta N$ is calculated by Equation (37) to obtain the following Equation (41).

$$\epsilon i(\omega)=\log(p(\omega))/Bi(\omega) \quad (41)$$

By subjecting Equation (41) to inverse Fourier transform, strain waveforms $\epsilon i(t)$, $i=1, 2, \ldots N$ are also calculated. Optionally, the impulse response $bi(t)$ may be calculated by subjecting $1/Bi(\omega)$ to inverse Fourier transform and $\epsilon i(t)$ may be obtained by performing a convolutional integration on either $p(t)$ or $\log(p(t))$ and $bi(t)$.

The comparing section 125 calculates the difference in a situation where the coefficient is determined so as to minimize the difference between either each of the viscosity property reference waveforms $\epsilon i(t)$, $i=1, 2, \ldots N$ or the thickness change waveform $y(t)$ that has been multiplied by the coefficient and the other waveform. More specifically, in Equations (7) and (9), the viscosity property reference waveforms $\epsilon i(t)$, $i=1, 2, \ldots N$ are substituted for the elastic property reference waveforms $M(t)$ and the k value calculated by Equation (9) is substituted into Equation (7) to calculate R. Since k is defined so as to minimize the squared difference R, the R value in this case is supposed to be $R_{im}$. That is to say, the difference $R_{im}$ (where $i=1, 2, \ldots N$) is calculated by the following Equation (42).

$$R_{im} = \sum_{t=0}^{N-1}\left(\epsilon_i(t) - \frac{\sum_{t=0}^{N-1}\epsilon_i(t)y(t)}{\sum_{t=0}^{N-1}(y(t))^2}y(t)\right)^2 \quad (42)$$

The viscosity coefficient determining section 121 receives the differences $R_{1m}, R_{2m}, \ldots R_{Nm}$ from the comparing section 125 to determine the viscosity coefficient $\eta i$ that is supposed for the viscosity property reference waveform resulting in the smallest difference, and then outputs the viscosity coefficient determined. The viscosity coefficient determined has not been calculated directly but is estimated to be a correct viscosity coefficient at the measuring site where the thickness change waveform was obtained for the reasons described above.

In this manner, the ultrasonic diagnostic apparatus 210 can calculate the modulus of elasticity and the viscosity coefficient. That is why even if it is difficult to determine, only by the modulus of elasticity, whether there is fat depot or inflammation due to angitis in the intima-media complex, such a decision can be made easily based on the value of the viscosity coefficient. As a result, according to the present invention, even a difference in the given tissue that has been difficult to identify only with a tomographic image or modulus of elasticity generated or calculated by a conventional ultrasonic diagnostic apparatus can be recognized by calculating the modulus of elasticity and viscosity coefficient, and diagnosis can be made more accurately.

In the preferred embodiment described above, the elastic property reference waveform and the viscosity property reference waveform are generated based on the blood pressure waveform. Alternatively, various other sorts of information about a variation in the stress applied to the subject or a variation in shape due to the stress variation may also be used to generate the elastic property reference waveform and the viscosity property reference waveform.

For example, the ultrasonic diagnostic apparatus 210' shown in FIG. 30 includes a vascular diameter calculating section 142 and generates an elastic property reference waveform and a viscosity property reference waveform based on a vascular caliber variation waveform. Specifically, the vascular diameter calculating section 142 receives either a waveform representing the displacement of two points in the proximity of the vascular foremen of the intima of the blood vessel or a waveform representing the displacement of two points in the proximity of the extravascular tissue outside of the adventitia of the blood vessel from the displacement waveform calculating section 115 and figures out a waveform representing a variation in the vascular caliber with respect to these two points. The reference waveform generating section 117G receives the vascular caliber variation waveform, and normalizes the waveform such that its amplitude becomes 1 μm, for example, thereby generating an elastic property reference waveform. Also, the reference waveform generating section 117G corrects the vascular caliber variation waveform with the highest and lowest blood pressure values received from the blood pressure manometer 119, thereby generating a blood pressure waveform p'(t). Furthermore, based on the blood pressure waveform p'(t), the reference waveform generating section 117G also generates viscosity property reference waveforms $\epsilon i(t)$, $i=1, 2, \ldots N$ as described above. In this case, to avoid being affected by the viscosity of the vessel wall, a waveform representing a variation in the inside caliber of the blood vessel is preferably used as the viscosity property reference waveform.

On the other hand, in the ultrasonic diagnostic apparatus 210" shown in FIG. 31, the reference waveform generating section 117F receives a waveform representing a variation in the thickness between two points in the proximity of the vascular lumen of the intima of the blood vessel from the thickness change waveform calculating section 116, and normalizes the waveform such that its amplitude becomes 1 μm, for example, thereby generating an elastic property reference waveform. Also, the reference waveform generating section 117F corrects a waveform representing a variation in the thickness between two points in the proximity of the vascular lumen with the highest and lowest blood pressure values received from the blood pressure manometer 119, thereby generating a blood pressure waveform p'(t). Furthermore, based on the blood pressure waveform p'(t), the reference waveform generating section 117F also generates viscosity property reference waveforms $\epsilon i(t)$, $i=1, 2, \ldots N$ as described above.

The vascular caliber variation waveform and the waveform representing a variation in the thickness between two points in proximity of the vascular lumen of the intima of the blood vessel are quite similar to a waveform representing a variation in blood pressure, which is a stress applied to the subject. That is why even if elastic property reference waveforms and viscosity property reference waveforms are generated based on these waveforms, the modulus of elasticity and the viscosity coefficient can also be calculated just as described above.

Furthermore, the same effects are also achieved even by figuring out a waveform representing a difference in velocity between either the two points at which the vascular caliber variation waveform has been obtained or the two points that are in proximity of the vascular lumen of the intima of the blood vessel. In that case, such a velocity difference waveform may be figured out in advance between two measuring points. Or the velocity difference waveform may also be figured out by differentiating the vascular caliber variation waveform with respect to time. As another alternative, the velocity difference waveform may also be figured out by differentiating the blood pressure waveform with respect to time.

In the preferred embodiment described above, the ultrasonic diagnostic apparatus calculates both the modulus of elasticity and the viscosity coefficient. However, to recognize a difference between tissues, it is not always necessary to calculate the modulus of elasticity.

Also, in the preferred embodiments described above, a waveform representing a variation in distance (or thickness) between two arbitrary measuring points on a subject is supposed to be used as a reference waveform. However, the same effects are achievable even if a waveform representing a difference in velocity between two arbitrary measuring points on a subject is used as a reference waveform. In that case, such a velocity difference waveform may be figured out in advance between two measuring points on multiple subjects. Or the velocity difference waveform may also be figured out by differentiating the vascular caliber variation waveform with respect to time. As another alternative, the velocity difference waveform may also be figured out by differentiating the blood pressure waveform with respect to time.

INDUSTRIAL APPLICABILITY

The ultrasonic diagnostic apparatus of the present invention can be used effectively to estimate an attribute property of a subject's tissue such as a thickness change, magnitude of strain and elastic property.

The invention claimed is:

1. An ultrasonic diagnostic apparatus comprising:
   a transmitting section that generates a drive signal to drive a probe in order to transmit an ultrasonic wave toward a subject to be deformed periodically under stress;
   a receiving section for receiving an echo, produced when the ultrasonic wave is reflected from the subject, at the probe to generate a received echo signal;
   a computing section for figuring out a thickness change waveform, representing a variation in distance between two arbitrary measuring points on the subject, based on the received echo signal;
   a reference waveform generating section for outputting a reference waveform; and
   a thickness change estimating section for calculating a coefficient to be multiplied by either the thickness change waveform or the reference waveform so as to minimize a matching error between the thickness change waveform and the reference waveform and for calculating the greatest variation in the thickness change waveform based on the coefficient and the amplitude of the reference waveform,
   wherein the reference waveform is generated by calculating the average of thickness change waveforms that have been collected in advance from a plurality of subjects, or is generated based on either a displacement waveform representing a displacement of a measuring point on the subject, a waveform representing a variation in the vascular caliber of the subject, or a waveform representing a variation in the blood pressure of the subject.

2. The ultrasonic diagnostic apparatus of claim 1, wherein the reference waveform generating section includes a storage section that stores data about the reference waveform generated by calculating the average of thickness change waveforms that have been collected in advance from a plurality of subjects.

3. The ultrasonic diagnostic apparatus of claim 2, further comprising a period adjusting section for adjusting the period of the reference waveform to one deformation period of the subject,
   wherein the thickness change estimating section calculates the greatest variation in the thickness change waveform based on the reference waveform, of which a period has been adjusted, and the thickness change waveform.

4. The ultrasonic diagnostic apparatus of claim 2, further comprising a period adjusting section for adjusting the period of the thickness change waveform to a period of the reference waveform,
   wherein the thickness change estimating section calculates the greatest variation in the thickness change waveform based on the thickness change waveform, of which a period has been adjusted, and the reference waveform.

5. The ultrasonic diagnostic apparatus of claim 4, further comprising an averaging section for averaging the thickness change waveform, of which the period has been adjusted, over multiple periods, and providing an averaged thickness change waveform,
   wherein the greatest variation in the thickness change waveform is calculated based on the averaged thickness change waveform and the reference waveform.

6. An ultrasonic diagnostic apparatus of claim 4 further comprising:
   an averaging section for calculating the average and the variance of the thickness change waveform, of which the period has been adjusted, over multiple periods, and providing an averaged thickness change waveform;

wherein the thickness change estimating section calculates the greatest thickness change by comparing the reference waveform and the averaged thickness change waveform to each other; and a reliability determining section for determining the reliability of the greatest thickness change based on the variance.

7. The ultrasonic diagnostic apparatus of claim 6, wherein the thickness change estimating section calculates the coefficient so as to minimize a difference between one of the averaged thickness change and reference waveforms and a waveform obtained by multiplying the other waveform by the coefficient, and wherein the thickness change estimating section also calculates the greatest thickness change in the thickness change waveform based on the coefficient and the amplitude of the reference waveform.

8. The ultrasonic diagnostic apparatus of claim 7, wherein the reliability determining section rates the reliability of the greatest thickness change based on the variance and the coefficient.

9. The ultrasonic diagnostic apparatus of claim 6, further comprising:

a modulus of elasticity calculating section for getting information about a difference in the stress that has been caused during a deformation period of the subject and for calculating a modulus of elasticity based on the greatest thickness change; and a display section for displaying the modulus of elasticity according to the degree of reliability that has been determined by the reliability determining section.

10. The ultrasonic diagnostic apparatus of claim 1, further comprising a period adjusting section, wherein if the thickness change waveform has inconstant periods, the period adjusting section extracts data about respective periods at an interval that corresponds to a shortest one of the periods of the thickness change waveform and provides the thickness change estimating section with the extracted data as the thickness change waveform.

11. The ultrasonic diagnostic apparatus of claim 1, wherein the computing section includes a displacement waveform calculating section for figuring out a displacement waveform representing displacements of a plurality of measuring points on the subject based on the received echo signal, wherein the two arbitrary measuring points are selected from the plurality of measuring points, and a thickness change waveform calculating section for figuring out the thickness change waveform between the two arbitrary measuring points based on the displacement waveform.

12. The ultrasonic diagnostic apparatus of claim 11, wherein the reference waveform generating section generates the reference waveform based on the displacement waveform.

13. The ultrasonic diagnostic apparatus of claim 11, further comprising a vascular diameter calculating section for figuring out a vascular caliber variation waveform representing a variation in the vascular caliber of the subject based on the displacement waveform, wherein the reference waveform generating section generates the reference waveform based on the vascular caliber variation waveform.

14. The ultrasonic diagnostic apparatus of claim 1, wherein the reference waveform generating section generates the reference waveform based on a waveform representing a variation in a blood pressure of the subject.

15. The ultrasonic diagnostic apparatus of claim 1, further comprising a modulus of elasticity calculating section for getting information about a difference in a stress that has been caused during a deformation period of the subject and for calculating a modulus of elasticity based on the greatest variation.

* * * * *

UNITED STATES PATENT AND TRADEMARK OFFICE
CERTIFICATE OF CORRECTION

PATENT NO. : 8,298,143 B2
APPLICATION NO. : 11/915884
DATED : October 30, 2012
INVENTOR(S) : Hiroshi Kanai et al.

It is certified that error appears in the above-identified patent and that said Letters Patent is hereby corrected as shown below:

On the Title Page, item (73), before "Panasonic Corporation, Osaka (JP)" should read
-- Tohoku University, Miyagi (JP) --.

Signed and Sealed this
Eleventh Day of June, 2013

Teresa Stanek Rea
*Acting Director of the United States Patent and Trademark Office*